US010365288B2

(12) United States Patent
Van Eyk et al.

(10) Patent No.: US 10,365,288 B2
(45) Date of Patent: *Jul. 30, 2019

(54) CITRULLINATED BRAIN AND NEUROLOGICAL PROTEINS AS BIOMARKERS OF BRAIN INJURY OR NEURODEGENERATION

(71) Applicant: THE JOHNS HOPKINS UNIVERSITY, Baltimore, MD (US)

(72) Inventors: Jennifer E. Van Eyk, Baltimore, MD (US); Allen Dale Everett, Baltimore, MD (US); Zhicheng Jin, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/636,076

(22) Filed: Jun. 28, 2017

(65) Prior Publication Data

US 2017/0370943 A1    Dec. 28, 2017

Related U.S. Application Data

(63) Continuation of application No. 14/384,848, filed as application No. PCT/US2013/031012 on Mar. 13, 2013, now Pat. No. 9,709,573.

(60) Provisional application No. 61/610,034, filed on Mar. 13, 2012.

(51) Int. Cl.
  *C12Q 1/00* (2006.01)
  *G01N 33/53* (2006.01)
  *G01N 33/542* (2006.01)
  *G01N 33/68* (2006.01)
  *H01J 49/00* (2006.01)

(52) U.S. Cl.
  CPC ..... *G01N 33/6848* (2013.01); *G01N 33/5306* (2013.01); *G01N 33/6842* (2013.01); *H01J 49/0027* (2013.01); *H01J 49/0077* (2013.01); *G01N 2440/18* (2013.01); *G01N 2800/28* (2013.01)

(58) Field of Classification Search
  None
  See application file for complete search history.

(56) References Cited

U.S. PATENT DOCUMENTS

| | | |
|---|---|---|
| 6,235,489 B1 | 5/2001 | Jackowski |
| 6,780,606 B1 | 8/2004 | Jackowski |
| 6,884,591 B2 | 4/2005 | Janigro et al. |
| 7,144,708 B2 | 12/2006 | Janigro et al. |
| 7,396,654 B2 | 7/2008 | Hayes et al. |
| 7,427,490 B2 | 9/2008 | Valkins |
| 7,456,027 B2 | 11/2008 | Wang et al. |
| 8,460,888 B2 | 6/2013 | Lafaye et al. |
| 8,492,107 B2 | 7/2013 | Wang et al. |
| 8,557,526 B2 | 10/2013 | Ottens et al. |
| 8,663,911 B2 | 3/2014 | Vojdani |
| 8,778,343 B2 | 7/2014 | Kayed |
| 9,194,867 B2 | 11/2015 | Vojdani |
| 9,709,573 B2 * | 7/2017 | Van Eyk ............ G01N 33/6842 |
| 2003/0040660 A1 | 2/2003 | Jackowski et al. |
| 2003/0077590 A1 | 4/2003 | Pederson et al. |
| 2003/0224460 A1 | 12/2003 | Pederson et al. |
| 2006/0257942 A1 | 11/2006 | Dambinova |
| 2007/0098728 A1 | 5/2007 | Pedersen et al. |
| 2008/0026485 A1 | 1/2008 | Hueber et al. |
| 2008/0131881 A1 | 6/2008 | Ladenson et al. |
| 2008/0220013 A1 | 9/2008 | Hochstrasser et al. |
| 2009/0068691 A1 | 3/2009 | Dave et al. |
| 2011/0082203 A1 | 4/2011 | Wang et al. |
| 2011/0177974 A1 | 7/2011 | Wang et al. |
| 2011/0207126 A1 | 8/2011 | Popko et al. |
| 2013/0252834 A1 | 9/2013 | Dayon et al. |
| 2014/0045713 A1 | 2/2014 | Everett et al. |
| 2014/0303041 A1 | 10/2014 | Hayes et al. |
| 2014/0342381 A1 | 11/2014 | Hayes |
| 2015/0004169 A1 | 1/2015 | Kayed |
| 2015/0118218 A1 | 4/2015 | Travis et al. |
| 2015/0119273 A1 | 4/2015 | Goldstein et al. |

(Continued)

FOREIGN PATENT DOCUMENTS

| | | |
|---|---|---|
| JP | 2008157905 | 10/2008 |
| JP | 2009-155226 A | 7/2009 |

(Continued)

OTHER PUBLICATIONS

Summons to Attend Oral Proceedings and Preliminary Opinion of the Examining Division in corresponding European Application No. 13760865.9, dated Mar. 15, 2018 (8 pages).

Ishigami et al., "Abnormal accumulation of citrullinated proteins catalyzed by peptidylarginine deiminase in hippocampal extracts from patients with Alzheimer's disease," Journal of Neuroscience Research. vol. 80, Issue 1, pp. 120-128 (Apr. 1, 2005).

Oguz et al., "Assessment of citrullinated myelin by 1H-MR spectroscopy in early-onset multiple sclerosis," American Journal of Neuroradiology, vol. 30, No. 4, pp. 716-721 (Jan. 15, 2009).

(Continued)

*Primary Examiner* — Olga N Chernyshev
(74) *Attorney, Agent, or Firm* — Melissa Hunter-Ensor; Leslie Serunian; Greenberg Traurig, LLP

(57) ABSTRACT

The present invention relates to the field of biomarkers. More specifically, the present invention relates to biomarkers useful in diagnosing brain injury or neurodegeneration. In one embodiment, a method for diagnosing brain injury in a patient comprises the steps of (a) obtaining a sample from the patient; (b) determining the ratio of citrullinated to unmodified arginine residues at one or more arginine residues of one or more brain injury biomarker proteins; and (c) correlating the ratio to a patient having brain injury or to a patient not having brain injury, thereby providing the diagnosis.

16 Claims, 23 Drawing Sheets

Specification includes a Sequence Listing.

(56) References Cited

U.S. PATENT DOCUMENTS

| | | |
|---|---|---|
| 2015/0141528 A1 | 5/2015 | Larner |
| 2015/0247867 A1 | 9/2015 | Curdt et al. |
| 2015/0268252 A1 | 9/2015 | Svetlov et al. |
| 2017/0146555 A1 | 5/2017 | Wang et al. |

FOREIGN PATENT DOCUMENTS

| | | |
|---|---|---|
| WO | 2004078098 A2 | 9/2004 |
| WO | 2006012351 A2 | 2/2006 |
| WO | 2008046509 A1 | 4/2008 |
| WO | 2009143519 A2 | 11/2009 |
| WO | 2010019553 A2 | 2/2010 |
| WO | 2010048388 A1 | 4/2010 |
| WO | 2010148391 A2 | 12/2010 |
| WO | 2011-032155 A2 | 3/2011 |
| WO | 2011032155 A2 | 3/2011 |
| WO | 2012051519 A2 | 4/2012 |
| WO | 2012155134 A2 | 11/2012 |
| WO | 2015009907 A1 | 1/2015 |
| WO | 2015066211 A1 | 5/2015 |
| WO | 2015157390 A1 | 10/2015 |
| WO | 2016055148 A2 | 4/2016 |
| WO | 2016087611 A1 | 6/2016 |
| WO | 2017008894 A1 | 1/2017 |

OTHER PUBLICATIONS

Zhicheng, Jin et al., "Identification and characterization of citrulline-modified brain proteins by combining HCD and CID fragmentation," Proteomics, vol. 13, No. 17, Aug. 7, 2013, pp. 2682-2691.

Nicholas, A., "Increased citrullinated glial fibrillary acidic protein in secondary progressive multiple sclerosis," Journal of Comparative Neurology, vol. 473, No. 1, May 17, 2004, pp. 128-136.

Byungki, J., "Citrullinated Proteins by Up-Regulated Peptidylarginine Deiminase 2 in Brains for Scrapie-Infected Mice a Possible Role in Pathogenesis," The American Journal of Pathology, vol. 173, No. 4, Oct. 4, 2008, pp. 1129-1142.

Nicholas, A. et al., "Expression of Citrullinated Proteins in Murine Experimental Autoimmune Encephalomyelitis," The Journal of Comparative Neurology, vol. 486, Jun. 8, 2005, pp. 254-266.

Communication and Supplemental European Search Report, cited in corresponding European Patent Application No. 13760865.9, dated Feb. 16, 2016, 29 pages.

Williams, L. et al. "Proteomic-based Approach for Biomarker Discovery to Predict Silent Cerebral Infart in Patients with Sickle Cell Disease," Paper Presented at the 51st Annual Meeting of the American Society of Hematology, New Orleans, LA, Dec. 6, 2009, pp. 1-2, obtained from https://ash.conference/ash/2009/webprogram/Paper20016.html on Jan. 28, 2016.

Hoshi, T. et al., "Relations of Serum High-Sensitivity C-Reactive Protein and Interleukin-6 Levels With Silent Brain Infarction," Stroke, vol. 36, No. 4., pp. 768-772, (2005).

Wang, et al., "MRI abnormalties of the brain in one-year-old children with sickle cell anemia," Pediatr Blood Cancer, Nov. 2008: 51(5): 643-6, doi: 10.1001/pbc.21612, (2008).

Pegelow et al. (2008) "Silient infarcts in children with sickle cell anemia and abnormal cerebral artery velocity," Arch. Neurol. Dec. 2001: 58(12) 2017-21.

Vendt et al. (2009) "Silent Cerebral Infarct Transfusion (SIT) trial imaging core: application of novel imaging information technology for rapid and central review of MRI of the brain," J. Digit Imaging, Jun. 2009; 22(3): 326-43. doi: 10.1007/s10278-008-9114-3. Epub Apr. 9, 2008.

Ottens et al. (2006) "Neuroproteomics in neurotrauma," Mass Spectrom Rev. May-Jun. 2006; 25(3): 380-408.

Berger et al.. (2006) "The Use of Biomarkers After Inflicted Traumatic Brain Injury: Insight into Eitology, Pathophysiology, and Biochemistry," Clin Ped Emer Med 7(3): 186-193.

Haqqani et al. (2007) "Biomarkers and diagnosis: protein biomarkers in serum of pediatric patients with sever traumatic brain injury identified by ICAT-LC-MS/MS," J. Neurotrauma, Jan. 2007; 24(1):54-74.

Hiergenroeder et al. (2008) "Biomarkers in the clinical diagnosis and management of traumatic brain injury," Mol. Diagn Ther. 2008; 12(6):345-58. doi: 10.2165/12504-44-200812060-00002.

Zetterberg, H. et al. "Neurochemical aftermath of amateur boxing," Arch Neurol. (2006). vol. 63, pp. 1277-1280.

Laterza, O., et al. "Biomarkers of tissue injury," Biomarkers Med. (2008) vol. 2, No. 1, pp. 81-92.

Extended European Search Report dated Feb. 10, 2014 for EP application 11833480.

Savage, W., et al., "Glial fibrillary acidic protein as a plasma biomarker of brain injury in children with sickle cell disease," American Journal of Hematology (2011) vol. 86, No. 5.

Thorsell, A., et al.., "Neurogranin in cerebrosphinal fluid as a marker of synaptic degeneration in Alzheimber's disease," Brain Research (2010) vol. 1362, pp. 13-22.

Pak, J. et al., "Involvment of neurogranin in the modulation of calcium/calmodulin-dependent protein kinase II, synapatic plasticity, and spatial learning: a study with kockout mice," Proc. Natl. Acad. Sci. USA, Oct. 10, 2000, vol. 97, No. 21, pp. 11232-11238.

Tok, J., et al., "Single microbead SELEX for efficient ssDNA aptamer generation against botulinum neurotoxin," Chem. Commun., Mar. 18, 2008, pp. 1883-1885.

Watson, J., et al., "Localization of RC3 (neurogranin) in rat brain subcellular fractions," Molecular Brain Research, Dec. 1, 1994, vol. 27, No. 2, pp. 323-328.

Clayton, D. et al., "Conservation and expression of IQ-domain-containing calpacitin gene products (neuromodulin/GAP-43, neurogranin/RC3) in the adult and developing oscine song control system," Development Neurobiology, Feb. 1, 2009, vol. 69, No. 2-3, pp. 124-140.

Laterza, O., et al., "Identification of novel brain biomarkers," Clinical Chemistry, American Association for Clinical Chemistry, Washington, DC, Sep. 1, 2006, vol. 52, No. 9, pp. 1713-1721.

Hoehna, Y., et al., "Matrix metalloproteinase 9 regulates cell dealth following pilocarpine-induced seizures in the developing brain," Neurobiology of Disease (2012), vol. 48, pp. 339-347.

Koumura, A. et al., "Metallothionein-3 deficient mice exhibit abnormalties of psychological behaviors," Neuroscience Letters, vol. 467, pp. 11-14 (2009).

European Search Report dated Oct. 9, 2015 for EP application 13760865.

Oliveira, C., et al., "Outcome biomarkers following severe traumatic brain injury," Revs. Bras. Ter Intensiva (2008) vol. 20, No. 4, pp. 411-421.

Radka, S. et al. "Presence of brain-derived neurotrophic factor in brain and human and rat but not mouse serum detected by a sensitive and specific immunoassay," Brain Research, vol. 709, pp. 122-130 (1996).

Zhang, H. et al., "Methods for peptide and protein quantification by liquid chromalography-multiple reaction monitoring mass spectrometry," Molecular & Cellular Proteomics, pp. 1-62 (2011).

European Search Report dated Jul. 13, 2015 for EP application 12782967.

Wu, L. et al., "Characterization using compartive proteomics, of differentially expressed proteins in the hippocampus of the mesial temporal lobe of epileptic rats following treatment with valproate," Amino Acids, vol. 40, pp. 221-238 (2011).

Iliuk, A., "Aptamer in Bioanalytical applications," Analytical Chemistry, vol. 823, pp. 4440-4452 (2011).

Tang, L. et al., "Attenuation of opioid tolerance by antisense oligodeoxynucleotides targeting neurogranin," European Journal of Pharmacology, vol. 542, pp. 106-107 (2006).

Tang, L. et al., "Disruption of acute opioid dependence by antisense oligodeoxynucleotides targeting neurogranin," Brain Research vol. 1143, pp. 78-82 (2007).

English machine-translation of Japanese Patent Publication JP 2009-155226, published Jul. 16, 2009, Applicants: Tokyo Metropolitian Foundation for Social Welfare & Public Health and Fujirebio Inc., (submitted in May 16, 2016 IDS), 53 pages.

(56) References Cited

OTHER PUBLICATIONS

Babcock, L. et al., "Ability of S100B to predict severity and cranial CT results in children with TBI," Brain Injury, vol. 26, No. 11, pp. 1372-1380 (2012).

Berger, R. et al., "Multiplex Assessment of Serum Biomarker Concentrations in Well-Appearing Children With Inflicted Traumatic Brain Injury," Pediatric Research, vol. 65, No. 1, pp. 97-102 (2009).

Biberthaler, P. et al., "Serum S-100B Concentration Provides Additional Information for the Indication of Computed Tomography in Patients After Minor Injury," Shock, vol. 25, No. 5, pp. 446-453 (2006).

Ingebrigtsen, T. et al., "The clinical value of serum S-100 protein measurements in minor head injury: a Scandinavian multicentre study," Brain Injury, vol. 14, No. 12, pp. 1047-1055 (2000).

Jeter, C. et al., "Biomarkers for the Diagnosis and Prognosis of Mild Traumatic Brain Injury/Concussion," Journal of Neurotrauma, vol. 30, pp. 657-670 (2013).

Mondello, S. et al., "Glial Neuronal Ratio: A Novel Index for Differentiating Injury Type in Patients with Severe Traumatic Brain Injury," Journal of Neurotrauma, vol. 29, pp. 1096-1104 (2012).

Papa, L. et al., "[Elevated] Levels of Serum Glial Fibrillary Acidic Protein Breakdown Products in Mild and Moderate Traumatic Brain Injury are Associated With Intracranial Lesions and Neurosurgical Intervention," Ann. Emerg. Med., vol. 59, No. 6, pp. 1-24 (2012).

Papa, L. et al., Serum levels of ubiquitin C-terminal hydrolase distinguish mild traumatic brain injury from trauma controls and are elevated in mild and moderate traumatic brain injury patients with intracranial lesions and neurosurgical intervention, J. Trauma, vol. 72, No. 5, pp. 1335-1344 (2012).

Rostami, E. et al., "Alteration in BDNF and its receptors, full-length and truncated TrkB and p75NTR following penetrating traumatic brain injury," Brain Research, vol. 1542, pp. 195-205 (2014).

Griesbach, G. et al., "Alterations in BDNF and Synapsin I within the Occipital Cortex and Hippocampus after Mild Traumatic Brain Injury in the Developing Rat: Reflections of Injury-Induced Neuroplasticity," Journal of Neurotrauma, vol. 19, No. 7, pp. 803-814 (2002).

Rodrigues, E. et al., "Increased serum brain derived neurotrophic factor (BDNF) following isolated severe traumatic brain injury in humans," Abstract No. 0196, Brain Injury, 22 (Supplement 1), p. 165 (2008).

Rostami, E. et al., "Proteomic-based identification of injury-specific patterns of biomarkers following different types of TBI," Presentation Abstract, Program 467.14/Poster AA14, Presentation date: Nov. 15, 2010, 40th Neuroscience Conference, San Diego, California, USA, Society for Neuroscience, 2010; Chalmers University of Technology, Gothenburg, Sweden, 2 pages.

Feala et al., "Systems Biology Approaches for Discovering Biomarkers for Traumatic Brain Injury", Journal of Neurotrauma, vol. 30, No. 13, pp. 1101-1116 (2013).

Zhang et al., "Human traumatic Brain Injury Induces Autoantibody Response Against Glial Fibrillary Acidic Protein and Its Breakdown Products", PLoS One, vol. 9, Issue 3, e92698, pp. 1-16, (2014).

\* cited by examiner

```
Bovine:  MDCCTESACS KPDDDILDIP LDDPGANAAA AKIQASFRGH MARKKIKSGE RGRKGPGPGG
60
         ------ --- ---------- ---------- ---------- ---------- ----------
Human:   MDCCTENACS KPDDDILDIP LDDPGANAAA AKIQASFRGH MARKKIKSGE RGRKGPGPGG
60

Bovine:  PGGAGGARGG AGGGPSGD 78 (SEQ ID NO:6)
         ----- --- --------
Human:   PGGAGAARGG AGGGPSGD 78 (SEQ ID NO:1)
```

FIG. 4

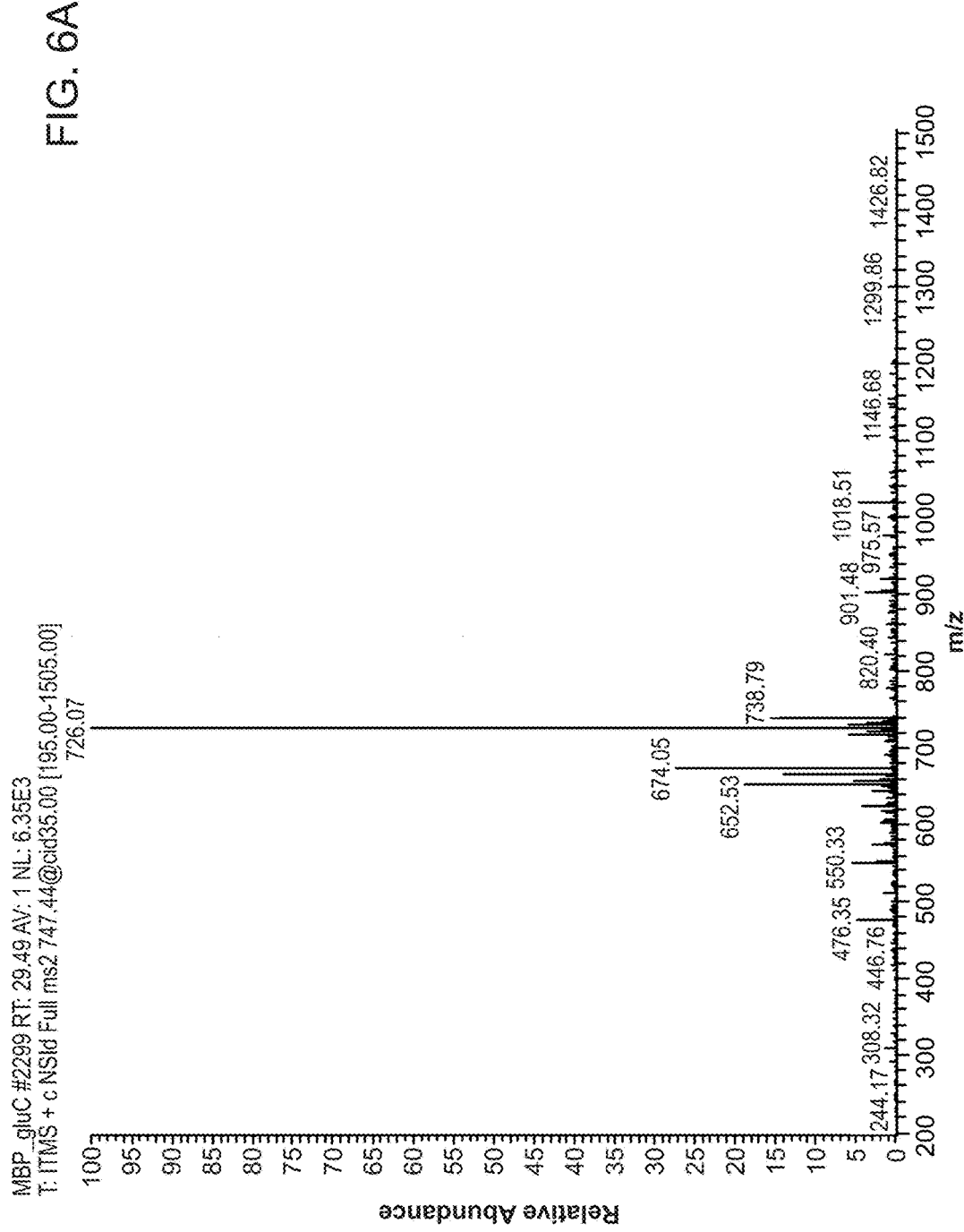

```
          1         10                    30                        50
MHHHHHENLYFQGATAMDCCTENACS KPDDDILDIPLDDPGANAAAA AKIQASFRGHMARKKIKSGE
              60                    78
RGRKGPGPGG PGGAGVARGGAGGGPSGDTR
```

FIG. 8

```
Human   MERRRITSAARRSYVSSGEMMVGGLAPGRR LGPGTRLSLARMPPPLPTRVDFSLAGALNA 60
        -----*---*--------*--*--...--- ------------------*-----------*
Bovine  MERRRVTSATRRSYVSSSEMVVG    GRR LGPGTRLSLARMPPPLPARVDFSLAGALNS 56

Human   GFKETRASERAEMMELNDRFASYIEKVRFL EQQNKALAAELNQLRAKEPTKLADVYQAEL 120
        ------------------------------ ------------------------------
Bovine  GFKETRASERAEMMELNDRFASYIEKVRFL EQQNKALAAELNQLRAKEPTKLADVYQAEL 116

Human   RELRLRLDQLTANSARLEVERDNLAQDLAT VRQKLQDETNLRLEAENNLAAYRQEADEAT 180
        ---------------------------*-- *---------*--------------------
Bovine  RELRLRLDQLTANSARLEVERDNLAQDLGT LRQKLQDETNQRLEAENNLAAYRQEADEAT 176

Human   LARLDLERKIESLEEEIRFLRKIHEEEVRE LQEQLARQQVHVELDVAKPDLTAALKEIRT 240
        ------------------------------ ------*------*-----------*----
Bovine  LARLDLERKIESLEEEIRFLRKIHEEEVRE LQEQLAQQQVHVEMDVAKPDLTAALREIRT 236

↓
Human   QYEAMASSNMHEAEEWYRSKFADLTDAAAR NAELLRQAKHEANDYRRQLQSLTCDLESLR 300
        ----*------------------*------ ---------------*--------------
Bovine  QYEAVASSNMHEAEEWYRSKFADLNDAAAR NAELLRQAKHEANDYRRQLQALTCDLESLR 296

Human   GTNESLERQMREQEERHVREAASYQEALAR LEEEGQSLKDEMARHLQEYQDLLNVKLALD 360
        -----------------*------------ ------------------------------
Bovine  GTNESLERQMREQEERHAREAASYQEALAR LEEEGQSLKDEMARHLQEYQDLLNVKLALD 356
                                                                    ↓
Human   IEIATYRKLLEGEENRITIPVQTFSNLQIR ETSLDTKSVSEGHLKRNIVVKTVEMRDGEV 420
        ------------------------------ ------------------------------
Bovine  IEIATYRKLLEGEENRITIPVQTFSNLQIR ETSLDTKSVSEGHLKRNIVVKTVEMRDGEV 416

Human   IKESKQEHKD VM 432  (SEQ ID NO:3)
        ---------- --
Bovine  IKESKQEHKD VM 428  (SEQ ID NO:7)
```

FIG. 10

```
              20                    40                       60
Human:  ASQKRPSQRHGSKYLATAST  MDHARHGFLPRHRDTGILDS  IGRFFGGDRGAPKRGSGKDS
        -*-------..-----*---  --------------------  -----*-------------*
Bovine: AAQKRPSQR   SKYLASAST  MDHARHGFLPRHRDTGILDS  LGRFFGSDRGAPKRGSGKDG
            18                    38                       58

90                      120
Human:  HHPARTAHYGSLPQK  SHGRTQDENPVVHFF  KNIVTPRTPPPSQGKGRGLSLSRFSWGAEG
        --*---*--------  .***-*---------  ------------------------------
Bovine: HHAARTTHYGSLPQKAQGHRPQDENPVVHFF  KNIVTPRTPPPSQGKGRGLSLSRFSWGAEG
                               89                      119

150
Human:  QRPGFGYGGRASDYKSAHKGFKGVDAQGTL  SKIFKLGGRDSRSGSPMARR 170 (SEQ ID NO:162)
        -*------------------*---------  ----------  ----------
Bovine: QKPGFGYGGRASDYKSAHKGLKGHDAQGTL  SKIFKLGGRDSRSGSPMARR 169 (SEQ ID NO:5)
                            149
```

FIG. 11

CITRULLINATED BRAIN AND NEUROLOGICAL PROTEINS AS BIOMARKERS OF BRAIN INJURY OR NEURODEGENERATION

CROSS-REFERENCE TO RELATED APPLICATIONS

This application is a continuation of patent application U.S. Ser. No. 14/384,848, filed on Sep. 12, 2014, now allowed, which is a U.S. National Stage Application under 35 U.S.C. § 371 of International PCT Application No. PCT/US2013/031012, having an international filing date of Mar. 13, 2013, which claims the benefit of U.S. Provisional Application No. 61/610,034, filed Mar. 13, 2012, the contents of all of which are incorporated herein by reference in their entireties.

STATEMENT OF GOVERNMENTAL INTEREST

This invention was made with U.S. government support under grant nos. 1R01HL091759-02, 5U54HL090515-02, and NHLBI-HV-10-05(2). The U.S. government has certain rights in the invention.

FIELD OF THE INVENTION

The present invention relates to the field of biomarkers. More specifically, the present invention relates to biomarkers useful in diagnosing brain injury or neurodegeneration.

INCORPORATION-BY-REFERENCE OF MATERIAL SUBMITTED ELECTRONICALLY

This application contains a sequence listing. It has been submitted electronically via EFS-Web as an ASCII text file entitled "167689_011706_US_SL.txt." The sequence listing is 72,281 bytes in size, and was created on Oct. 15, 2018. It is hereby incorporated by reference in its entirety.

BACKGROUND OF THE INVENTION

Clinical tools such as physical exam, and CNS imaging (CT Scan or MRI) are subjective, not widely available, not sensitive or specific enough and too costly to identify the infant, child or adult with CNS injury. This can include individuals on life support or cardiopulmonary bypass, trauma, loss of oxygen, etc, regardless of the initial injury or disease. There is a great clinical need to identify patients with CNS or brain injury and especially subclinical injury because these infants, children and adults are at significant risk of progressing to overt stroke and development of cognitive and motor loss, dementia and poor mental performance. In addition, accurate and sensitive identification of CNS injury by circulating biomarkers will provide an objective gold standard to test and compare new therapeutic modalities for efficacy.

SUMMARY OF THE INVENTION

The present invention is based, at least in part, on the discovery of unique post-translational modifications (e.g., citrullination) of CNS proteins neurogranin (NRGN), myelin basic protein (MBP), glial fibrillary acid protein (GFAP), tubulin beta-4B chain, tubulin alpha-1B chain, CNPase, PPIA, Septin-7, Elongation factor1-alpha2, TPPP, TPPP3, Ermin Isoform 2, and NDRG2 Isoform 2. Other proteins include astrotactin 1 (ASTN1); brain angiogenesis inhibitor 3 (BAI3); carnosine dipeptidase 1 (CNDP1); ERMIN; glutamate receptor metabotropic 3 (GRM3); kelch-like protein 32 (KLH32); melanoma antigen family E,2 (MAGE2); myelin basic protein (MBP); neuregulin 3 (NRG3); oligodendrocyte myelin glycoprotein (OMG); solute carrier family 39 (zinc transporter); reticulon 1 (RTN1); and peptidylarginine deiminase (types 1-4 and 6) (PAD) (including PAD-2), are found circulating in patients with brain injury. Thus, the present invention provides methods for the detection and quantification of one or more modified protein or specific amino acid residues on one or more brain injury biomarker proteins. As described further herein, the present invention also provides methods for the detection and quantification of autoantibodies to the unmodified and/or modified brain injury biomarker proteins listed above.

Accordingly, the identification and development of assays for post-translation modifications and unmodified forms of brain specific circulating proteins such as NRGN, MBP and GFAP provide a new specific diagnostic of brain injury providing the exquisite brain specificity for an accurate and fast diagnosis. In addition, modified forms of NRGN, MBP and GFAP provide information on the biology of injury that can be useful for defining the phase of injury or recovery that can be used for targeting specific therapies to personalize and improve outcome. Ratios of citrullinated to non-citrullinated proteins could be used to determine the risk or progression of CNS injury, stroke, reduced mental capacity, and neurodegenerative diseases.

As described in certain embodiments, unmodified and citrullinated NRGN, MBP and/or GFAP represent a new diagnostic assay for brain injury. The present invention provides kits using antibodies, aptamers, and mass spectrometry based methods for detection of citrullinated proteins and or modified amino acid residues. The present invention can be used to detect and/or quantify brain injury biomarkers in various body fluids (including plasma, serum, cerebral spinal fluid) and tissue and cells.

In specific embodiments, the citrullination at residues at NRGN: R38, R43, R51, R53, R68; MBP: R31, R43, R49, R65, R107, R113, R162, R169; and GFAP: R88, R105, R124, R126, R136, R173, R217, R258, R270, R286, R287, R367, R406, and combinations of any of the foregoing can be used to diagnosis brain injury in a patient. In more specific embodiments, the detection and quantification can be directed at the ratio of modified to unmodified proteins or specific amino acid residues.

The present invention is applicable to the prediction of the susceptibility or presence of both subclinical and overt brain injury. The present invention further provides protein diagnostic(s)/prognostic(s) useful for identifying infants, children and adults with subclinical brain injury, in which routine clinical assessments are normal, to prevent progression to overt stroke. More specifically, protein diagnostic(s)/prognostic(s) of the present invention can be used to assess and monitor efficacy of therapies in infants, children and adults. In fact, the protein diagnostic(s)/prognostic(s) described herein can be used to identify brain injury in ill infants, children and adults at risk for brain injury and to predict outcomes.

In other embodiments, protein diagnostic(s)/prognostic(s) can be used to (1) identify brain injury in children and adults on life support or cardiopulmonary bypass including during surgery (regardless of initialing injury or disease) to assess potential neurological injury; (2) identify the permeability of the blood brain barrier; and/or (3) identify degenerative brain disease.

Furthermore, as citrullination of proteins has been proposed to increase immunogenicity of some proteins, the identification of citrullinated brain proteins may be very important for diagnosis of chronic neurodegenerative diseases such as chronic traumatic encephalopathy, Alzheimer's disease, multiple sclerosis and Parkinson's disease. It is possible that auto-antibodies against the various citrullinated forms of these proteins could act as auto-antigens following brain injury exacerbating brain injury. Thus, detection (or blocking) of these auto-antibodies could be used for improved prognosis, risk stratification, or therapy.

Accordingly, the present invention provides methods for diagnosing brain injury in a patient. In one embodiment, a method for diagnosing brain injury in a patient comprises the steps of (a) obtaining a sample from the patient; (b) determining the ratio of citrullinated to unmodified arginine residues at one or more arginine residues of one or more brain injury biomarker proteins; and (c) correlating the ratio to a patient having brain injury or to a patient not having brain injury, thereby providing the diagnosis.

The sample can be selected from the group consisting of blood, peripheral blood, serum, plasma, cerebrospinal fluid, urine, saliva, stool and synovial fluid. In a specific embodiment, the sample is blood, plasma serum, cerebrospinal fluid (CSF), or urine. In a more specific embodiment, the sample is CSF. In another specific embodiment, the sample is blood. In an alternative embodiment, the sample is serum.

In certain embodiments, the determining step is accomplished using mass spectrometry. In a specific embodiment, the determining step is accomplished using multiple reaction monitoring mass spectrometry (MRM-MS). In other embodiments, the determining step is accomplished using an immunoassay. In further embodiments, aptamers, peptoids, or other capture/detection systems are used.

In a specific embodiment, the one or more brain injury biomarker proteins is neurogranin (NRGN), myelin basic protein (MBP), glial fibrillary acid protein (GFAP), peptidylarginine deiminase (PAD), isoforms thereof, post-translationally modified forms thereof, or combinations of any of the foregoing. In a more specific embodiment, the brain injury biomarker protein is NRGN, isoforms thereof, or post-translationally modified forms thereof. In another specific embodiment, the brain injury biomarker protein is MBP, isoforms thereof, or post-translationally modified forms thereof. In yet another embodiment, the brain injury biomarker protein is GFAP, isoforms thereof, or post-translationally modified forms thereof. In a further embodiment, in the brain injury biomarker protein is PAD-2, isoforms thereof, or post-translationally modified forms thereof.

In yet another embodiment, the brain injury biomarker protein is one or more proteins selected from the group consisting of tubulin beta-4B chain; tubulin alpha-1B chain; CNPase; PPIA; Septin-7; Elongation factor1-alpha2; TPPP; TPPP3; Ermin Isoform 2; NDRG2 Isoform 2, astrotactin 1 (ASTN1), brain angiogenesis inhibitor 3 (BAI3); carnosine dipeptidase 1 (CNDP1); ERMIN; glial fibrillary acidic protein (GFAP); glutamate receptor metabotropic 3 (GRM3); kelch-like protein 32 (KLH32); melanoma antigen family E,2 (MAGE2); myelin basic protein (MBP); neuregulin 3 (NRG3); neurogranin (NRGN); oligodendrocyte myelin glycoprotein (OMG); solute carrier family 39 (zinc transporter); reticulon 1 (RTN1); and peptidylarginine deiminase (types 1-4 and 6) (PAD); isoforms thereof; post-translationally modified forms thereof; or combinations of any of the foregoing.

The present invention also provides a method for diagnosing brain injury in a patient comprising the steps of (a) determining the ratio of one or more citrullinated peptides to the corresponding unmodified peptides in a sample collected from the patient using mass spectrometry; and (b) correlating the ratio to a patient having brain injury or to a patient not having brain injury, thereby providing the diagnosis. In an alternative embodiment, a method for diagnosing brain injury in a patient comprises the steps of (a) determining the ratio of one or more citrullinated peptides to the corresponding unmodified peptides in a sample collected from the patient using mass spectrometry; and (b) comparing the ratio with predefined ratios of the same peptides that correlate to a patient having brain injury and predefined ratios of the same peptides that correlate to a patient not having brain injury, wherein a correlation to one of the predefined ratios provides the diagnosis.

In such embodiments, the one or more peptides is selected from the group consisting of tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GFAP, GRM3, KLH32, MAGE2, MBP, NRG3, NRGN, OMG, SLC39A12, RTN1, MT3, PAD (including PAD-2), isoforms thereof, post-translationally modified forms thereof, or combinations of any of the foregoing. Alternatively, the one or more peptide is NRGN, MBP, GFAP, PAD or a combination thereof. In other embodiments, the one or more peptide is NRGN, MBP, GFAP, isoforms thereof, post-translationally modified forms thereof, or combinations of any of the foregoing.

In a specific embodiment, the present invention provides a method for diagnosing brain injury in a patient comprising the steps of (a) determining the ratio of one or more post-translationally modified peptides to the corresponding unmodified peptides in a sample collected from the patient using MRM-MS; and (b) correlating the ratio to a patient having brain injury or to a patient not having brain injury, thereby providing the diagnosis. In another specific embodiment, a method for diagnosing brain injury in a patient comprises the steps of (a) determining the ratio of one or more post-translationally modified peptides to the corresponding unmodified peptides in a sample collected from the patient using MRM-MS; and (b) comparing the one or more ratios with predefined ratios of the same post-translationally modified/unmodified peptides that correlate to a patient having brain injury and predefined ratios of the same post-translationally modified/unmodified peptides that correlate to a patient not having brain injury, wherein a correlation to one of the predefined ratios provides the diagnosis.

In such embodiments, the post-translational modification is citrullination, oxidation, methylation, phosphorylation, cysteinylation s-nitrosation, s-glutathyolation, or a combination thereof. Moreover, the one or more peptides can be selected from the group consisting of tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GFAP, GRM3, KLH32, MAGE2, MBP, NRG3, NRGN, OMG, SLC39A12, RTN1, PAD, isoforms thereof, post-translationally modified forms thereof, or combinations of any of the foregoing. In a specific embodiment, the one or more peptide is NRGN, MBP, GFAP, PAD, isoforms thereof, post-translationally modified forms thereof, or combinations of any of the foregoing.

In another embodiment, a method for diagnosing brain injury in a patient comprises the steps of (a) determining the ratio of one or more citrullinated peptides to the corresponding unmodified peptides in a sample collected from the patient using mass spectrometry; (b) determining the ratio of one or more post-translationally modified peptides to the corresponding unmodified peptides in the same sample collected from the patient using MRM-MS; (c) comparing the one or more citrullinated:unmodified peptide ratios to one or more post-translationally modified:unmodified peptide ratios; and (d) correlating the compared ratios to a patient having brain injury or to a patient not having brain injury, thereby providing the diagnosis.

In another embodiment, a method for diagnosing brain injury in a patient comprises the steps of (a) determining the degree of citrullination of one or more arginine sites of one or more of NRGN, PAD, MBP GFAP, isoforms thereof, post-translationally modified forms thereof, or combinations of any of the foregoing; and (b) correlating the degree of citrullination to a patient having brain injury or to a patient not having brain injury, thereby providing the diagnosis.

In particular embodiments, the peptides are one or more peptides as shown in Tables 5-9, 11-12, and 14-17. In other embodiments, the peptides comprise an amino acid sequence of about 8 to about 45 amino acid residues of NRGN, MBP, GFAP, and PAD, isoforms thereof, post-translationally modified forms thereof, or combinations of any of the foregoing. In further embodiments, the peptides comprise an amino acid sequence of about 8 to about 45 amino acid residues of tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GFAP, GRM3, KLH32, MAGE2, MBP, NRG3, NRGN, OMG, SLC39A12, RTN1, PAD, isoforms thereof, post-translationally modified forms thereof, or combinations of any of the foregoing.

In another aspect, the present invention provides methods for determining the concentration or levels of citrullinated brain injury biomarker proteins/peptides. In one embodiment, a method for diagnosing brain injury in a patient comprises the steps of (a) measuring the level of one or more citrullinated brain injury biomarker proteins in a sample collected from the patient; and (b) comparing the level of the one or more biomarkers with predefined levels of the same biomarkers that correlate to a patient having brain injury and predefined levels of the same biomarkers that correlate to a patient not having brain injury, wherein a correlation to one of the predefined levels provides the diagnosis.

In particular embodiments, the one or more brain injury biomarker proteins is tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GFAP, GRM3, KLH32, MAGE2, MBP, NRG3, NRGN, OMG, SLC39A12, RTN1, MT3, PAD, isoforms thereof, post-translationally modified forms thereof, or combinations of any of the foregoing. Alternatively, the one or more brain injury biomarker proteins is NRGN, MBP, GFAP, PAD, isoforms thereof, post-translationally modified forms thereof, or combinations of any of the foregoing. In a specific embodiment, the brain injury biomarker protein is NRGN, isoforms thereof, or post-translationally modified forms thereof. In another embodiment, the brain injury biomarker protein is MBP, isoforms thereof, or post-translationally modified forms thereof. In yet another embodiment, the brain injury biomarker protein is GFAP, isoforms thereof, or post-translationally modified forms thereof. In a further embodiment, the brain injury biomarker protein is PAD, isoforms thereof, or post-translationally modified forms thereof.

In such embodiments, the sample can be selected from the group consisting of blood, peripheral blood, serum, plasma, cerebrospinal fluid, urine, saliva, stool and synovial fluid. In a specific embodiment, the sample is blood, plasma serum, cerebrospinal fluid (CSF), or urine. In a more specific embodiment, the sample is CSF. In another specific embodiment, the sample is blood. In yet another embodiment, the sample is serum.

In certain embodiments, the determining step is accomplished using mass spectrometry. In a specific embodiment, the determining step is accomplished using multiple reaction monitoring mass spectrometry (MRM-MS). In other embodiments, the determining step is accomplished using an immunoassay. In further embodiments, aptamers, peptoids, or other capture/detection systems are used.

The present invention also provides a method for diagnosing brain injury in a patient comprising the steps of (a) collecting a sample from the patient; (b) measuring the levels of a panel of citrullinated brain injury biomarker proteins in the sample collected from the patient using mass spectrometry, wherein the panel of biomarkers comprises NRGN, MBP, GFAP, PAD, isoforms thereof, post-translationally modified forms thereof, or combinations of any of the foregoing; and (c) comparing the levels of the panel of biomarkers with predefined levels of the same panel of biomarkers that correlate to a patient having brain injury and predefined levels of the same panel of biomarkers that correlate to a patient not having brain injury, wherein a correlation to one of the predefined levels provides the diagnosis.

The panel of biomarkers can further comprise one or more citrullinated brain injury biomarker proteins selected from the group consisting of tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GRM3, KLH32, MAGE2, NRG3, OMG, SLC39A12, RTN1, MT3, isoforms thereof, post-translationally modified forms thereof, or combinations of any of the foregoing.

In another embodiment, a method for determining brain injury status in a patient comprises the steps of (a) collecting a sample from the patient; (b) measuring the levels of a panel of citrullinated brain injury biomarker proteins in the sample collected from the patient using SRM-MS, wherein the panel of biomarkers comprises NRGN, MBP, GFAP, PAD, isoforms thereof, post-translationally modified forms thereof, or combinations of any of the foregoing; and (c) comparing the levels of the panel of biomarkers with predefined levels of the same panel of biomarkers that correlate to one or more brain injury statuses selected from the group consisting of having brain injury, not having brain injury, progressing brain injury, and regressing brain injury, wherein a correlation to one of the predefined levels determines the brain injury status of the patient. In another embodiment, the panel of biomarkers further comprises one or more citrullinated brain injury biomarker proteins selected from the group consisting of tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GRM3, KLH32, MAGE2, NRG3, OMG, SLC39A12, RTN1, MT3, isoforms thereof, post-translationally modified forms thereof, or combinations of any of the foregoing.

The present invention also provides diagnostic kits for use in diagnosing brain injury in a patient. In one embodiment, a diagnostic kit for diagnosing brain injury in a patient comprises (a) a substrate for collecting a biological sample from the patient; and (b) means for measuring the levels of one or more human citrullinated brain injury biomarker proteins selected from the group consisting of NRGN, MBP, GFAP, PAD, isoforms thereof, post-translationally modified forms thereof, or combinations of any of the foregoing. In another embodiment, the one or more human citrullinated brain injury biomarker proteins further comprises tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GRM3, KLH32, MAGE2, NRG3, OMG, SLC39A12, RTN1, MT3, isoforms thereof, post-translationally modified forms thereof, or combinations of any of the foregoing.

In certain embodiments, the ratio of one or more citrullinated peptides to the corresponding unmodified peptides in GFAP is one or more of SEQ ID NO:28:SEQ ID NO:27; SEQ ID NO:30:SEQ ID NO:29; SEQ ID NO:40:SEQ ID NO:41; SEQ ID NO:42:SEQ ID NO:43; SEQ ID NO:44: SEQ ID NO:45; SEQ ID NO:46: SEQ ID NO:47; SEQ ID NO:48: SEQ ID NO:49; SEQ ID NO:50: SEQ ID NO:51; SEQ ID NO:52: SEQ ID NO:53; SEQ ID NO:54: SEQ ID NO:55; SEQ ID NO:56: SEQ ID NO:57; SEQ ID NO:91: SEQ ID NO:92; SEQ ID NO:93: SEQ ID NO:94; SEQ ID NO:95: SEQ ID NO:96; SEQ ID NO:97: SEQ ID NO:27; SEQ ID NO:98: SEQ ID NO:160; SEQ ID NO:118: SEQ ID NO:119; SEQ ID NO:120: SEQ ID NO:121; SEQ ID NO:122: SEQ ID NO:123; and SEQ ID NO:124: SEQ ID N0:125.

In other embodiments, the ratio of one or more citrullinated peptides to the corresponding unmodified peptides in MBP is one or more of SEQ ID NO:32: SEQ ID NO:31; SEQ ID NO:34: SEQ ID NO:33; SEQ ID NO:75: SEQ ID NO:74; SEQ ID NO:77: SEQ ID NO:76; SEQ ID NO:68: SEQ ID NO:69; SEQ ID NO:79: SEQ ID NO:78; SEQ ID NO:80: SEQ ID NO:78; SEQ ID NO:104: SEQ ID NO:105; SEQ ID NO:106: SEQ ID NO:107; SEQ ID NO:108: SEQ ID NO:109; SEQ ID NO:110: SEQ ID NO:111; SEQ ID NO:112: SEQ ID NO:113; SEQ ID NO:114: SEQ ID NO:115; and SEQ ID NO:116: SEQ ID NO:117.

In further embodiments, the ratio of one or more citrullinated peptides to the corresponding unmodified peptides in NRGN is one or more of SEQ ID NO:35: SEQ ID NO:36; SEQ ID NO:37: SEQ ID NO:157; SEQ ID NO:71: SEQ ID NO:73; SEQ ID NO:77: SEQ ID NO:159; and SEQ ID NO:99: SEQ ID NO:100.

In additional embodiments, the ratio of one or more citrullinated peptides to the corresponding unmodified peptides in the proteins listed in Table 17 is one or more of SEQ ID NO:128: SEQ ID NO:129; SEQ ID NO:130: SEQ ID NO:131; SEQ ID NO:132: SEQ ID NO:133; SEQ ID NO:134: SEQ ID NO:135; SEQ ID NO:136: SEQ ID NO:137; SEQ ID NO:138: SEQ ID NO:139; SEQ ID NO:140: SEQ ID NO:141; SEQ ID NO:142: SEQ ID NO:143; SEQ ID NO:144: SEQ ID NO:145; SEQ ID NO:146: SEQ ID NO:147; SEQ ID NO:148: SEQ ID NO:149; SEQ ID NO:150: SEQ ID NO:151; SEQ ID NO:152: SEQ ID NO:153; and SEQ ID NO:154: SEQ ID NO:155.

Furthermore, the present invention provides for the combination of any of the foregoing ratios of citrullinated or other post-translationally modified peptides to the corresponding unmodified peptides provided herein including, but not limited to, SEQ ID NO:28:SEQ ID NO:27; SEQ ID NO:30:SEQ ID NO:29; SEQ ID NO:40: SEQ ID NO:41; SEQ ID NO:42:SEQ ID NO:43; SEQ ID NO:44: SEQ ID NO:45; SEQ ID NO:46: SEQ ID NO:47; SEQ ID NO:48: SEQ ID NO:49; SEQ ID NO:50: SEQ ID NO:51; SEQ ID NO:52: SEQ ID NO:53; SEQ ID NO:54: SEQ ID NO:55; SEQ ID NO:56: SEQ ID NO:57; SEQ ID NO:91: SEQ ID NO:92; SEQ ID NO:93: SEQ ID NO:94; SEQ ID NO:95: SEQ ID NO:96; SEQ ID NO:97: SEQ ID NO:27; SEQ ID NO:98: SEQ ID NO:160; SEQ ID NO:118: SEQ ID NO:119; SEQ ID NO:120: SEQ ID NO:121; SEQ ID NO:122: SEQ ID NO:123; SEQ ID NO:124: SEQ ID NO:125; SEQ ID NO:32: SEQ ID NO:31; SEQ ID NO:34: SEQ ID NO:33; SEQ ID NO:75: SEQ ID NO:74; SEQ ID NO:77: SEQ ID NO:76; SEQ ID NO:68: SEQ ID NO:69; SEQ ID NO:79: SEQ ID NO:78; SEQ ID NO:80: SEQ ID NO:78; SEQ ID NO:104: SEQ ID NO:105; SEQ ID NO:106: SEQ ID NO:107; SEQ ID NO:108: SEQ ID NO:109; SEQ ID NO:110: SEQ ID NO:111; SEQ ID NO:112: SEQ ID NO:113; SEQ ID NO:114: SEQ ID NO:115; SEQ ID NO:116: SEQ ID NO:117; SEQ ID NO:35: SEQ ID NO:36; SEQ ID NO:37: SEQ ID NO:157; SEQ ID NO:71: SEQ ID NO:73; SEQ ID NO:77: SEQ ID NO:159; SEQ ID NO:99: SEQ ID NO:100; SEQ ID NO:128: SEQ ID NO:129; SEQ ID NO:130: SEQ ID NO:131; SEQ ID NO:132: SEQ ID NO:133; SEQ ID NO:134: SEQ ID NO:135; SEQ ID NO:136: SEQ ID NO:137; SEQ ID NO:138: SEQ ID NO:139; SEQ ID NO:140: SEQ ID NO:141; SEQ ID NO:142: SEQ ID NO:143; SEQ ID NO:144: SEQ ID NO:145; SEQ ID NO:146: SEQ ID NO:147; SEQ ID NO:148: SEQ ID NO:149; SEQ ID NO:150: SEQ ID NO:151; SEQ ID NO:152: SEQ ID NO:153; and SEQ ID NO:154: SEQ ID NO:155.

In another aspect, the present invention provides methods for diagnosing brain injury by detecting autoantibodies to one or more citrullinated biomarker peptides described herein. In one embodiment, a method for diagnosing brain injury in a subject comprises the steps of (a) collecting a sample from the subject; (b) detecting the presence of autoantibodies to citrullinated brain injury biomarker peptides in the sample collected from the subject; and (c) correlating the amount of autoantibodies to citrullinated brain injury biomarker peptides to a patient having brain injury or to a patient not having brain injury, thereby providing the diagnosis. In another embodiment, the detecting step comprises the steps of (a) contacting a biological sample taken from a subject with a citrullinated brain injury biomarker peptide; and (b) detecting the binding of the peptide with an autoantibody specific for the peptide, wherein the detection of binding is indicative of the presence of citrullinated brain injury biomarker peptide autoantibodies in the subject. In a specific embodiment, the binding is detected by enzyme-linked immunosorbent assay (ELISA), immunoprecipitation or immunoblotting. In certain embodiments, the citrullinated brain injury biomarker peptide is one or more of NRGN, MBP, GFAP, PAD-2, tubulin beta-4B chain, tubulin alpha-1B chain, CNPase, PPIA, Septin-7, Elongation factor1-alpha2, TPPP, TPPP3, Ermin Isoform 2, and NDRG2 Isoform 2. In other embodiments, the citrullinated brain injury biomarker peptide is one or more of ASTN1, BAI3, CNDP1, ERMIN, GFAP, GRM3, KLH32, MAGE2, MBP, NRG3, NRGN, OMG, SLC39A12, RTN1, MT3, PAD.

In another embodiment, a method for assessing efficacy of a brain injury treatment regimen in a subject comprises the steps of (a) establishing a baseline level of autoantibodies to cit-NRGN, cit-MBP, and cit-GFAP in a subject prior to brain injury treatment regimen; (b) monitoring the levels of autoantibodies to cit-NRGN, cit-MBP, and cit-GFAP using a cit-NRGN, cit-MBP, and cit-GFAP peptide at least at one point after initiation of the brain injury treatment regimen; and (c) comparing the observed level of autoantibodies to cit-NRGN, cit-MBP, and cit-GFAP to the baseline level of autoantibodies to cit-NRGN, cit-MBP, and cit-GFAP, wherein a decrease in the level of autoantibodies is indicative of the efficacy of the brain injury treatment regimen. In a specific embodiment, the level of autoantibodies to cit-NRGN, cit-MBP, and cit-GFAP is measured by ELISA, immunoprecipitation or immunoblotting. In other embodiments, the baseline level of autoantibodies is also established with respect to one of more of citrullinated tubulin beta-4B chain, tubulin alpha-1B chain, CNPase, PPIA, Septin-7, Elongation factor1-alpha2, TPPP, TPPP3, Ermin Isoform 2, and NDRG2 Isoform 2. In other embodiments, the baseline level of autoantibodies is also established with respect to one or more of ASTN1, BAI3, CNDP1, ERMIN, GFAP, GRM3, KLH32, MAGE2, MBP, NRG3, NRGN, OMG, SLC39A12, RTN1, MT3, PAD.

In a further embodiment, a method for qualifying brain injury status in a subject comprises the steps of (a) measuring the level of autoantibodies to cit-NRGN, cit-MBP, and cit-GFAP in a biological sample from the subject; and (b) correlating the measurement with brain injury status. In a specific embodiment, the level of autoantibodies to cit-NRGN, cit-MBP, and cit-GFAP is measured by ELISA, immunoprecipitation or immunoblotting. In particular embodiments, the brain injury status is selected from the group consisting of the risk of brain injury, the development of brain injury, the presence or absence of brain injury, the stage of brain injury, the subtype of brain injury, the prognosis for the subject, and the effectiveness of treatment of brain injury.

In another aspect, the present invention relates to methods for detecting the presence of autoantibodies to citrullinated peptides in a subject (cit-peptide autoantibodies) in a subject. In certain embodiments, the citrullinated peptide is MBP, GFAP, tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GFAP, GRM3, KLH32, MAGE2, NRG3, NRGN, OMG, SLC39A12, RTN1, MT3, and PAD2, as well as the peptides listed in Tables 1-11 and 13-17. The present invention also relates to methods for detecting the presence of autoantibodies to unmodified peptides.

In particular embodiment, the method comprises contacting a biological sample taken from a subject with a polypeptide of the present invention and detecting the binding of the polypeptide with an autoantibody specific for the polypeptide, wherein the detection of binding is indicative of the presence of cit-polypeptide autoantibodies in the subject. In such methods, the binding can be detected by enzyme-linked immunosorbent assay (ELISA), immunoprecipitation or immunoblotting.

In yet another aspect, the present invention relates to methods for assessing efficacy of a brain injury treatment regimen in a subject. In particular embodiments, the methods comprise establishing a baseline level of cit-peptide autoantibodies in a subject prior to a brain injury treatment regimen; monitoring the level of cit-peptide autoantibodies using a polypeptide of the present invention at least at one point after initiation of the brain injury treatment regimen; and comparing the observed level of cit-peptide autoantibodies to the baseline level of cit-peptide autoantibodies, wherein a decrease in the level of peptide autoantibodies is indicative of the efficacy of the brain injury treatment regimen. The peptide can be one or more of peptide is MBP, GFAP, PAD-2, tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GFAP, GRM3, KLH32, MAGE2, NRG3, NRGN, OMG, SLC39A12, RTN1, MT3, and PAD2. In such methods, the binding can be detected by enzyme-linked immunosorbent assay (ELISA), immunoprecipitation or immunoblotting.

In a further aspect, the present invention relates to methods for qualifying brain injury status in a subject. Qualifying brain injury status can be qualifying the risk of brain injury, the development of brain injury, the presence or absence of brain injury, the stage of brain injury, the subtype of brain injury, the prognosis for the subject, and the effectiveness of treatment for brain injury. In certain embodiments, the methods comprise measuring the level of cit-peptide autoantibodies in a biological sample from the subject; and correlating the measurement with brain injury status. In one embodiment, the level of cit-peptide autoantibodies is measured using a polypeptide described herein. In another embodiment, the level of cit-peptide autoantibodies is measured by ELISA, immunoprecipitation or immunoblotting. The peptide can be one or more of peptide is MBP, GFAP, PAD-2, tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GFAP, GRM3, KLH32, MAGE2, NRG3, NRGN, OMG, SLC39A12, RTN1, MT3, and PAD2.

Finally, the present invention provides methods of detecting, measuring, determining, and the like, the biomarkers described herein in terms of both unmodified and modified forms, as well as autoantibodies thereto, i.e., combinations of both protein form and autoantibodies thereto.

BRIEF DESCRIPTION OF THE FIGURES

FIG. 1A: LTQ MS/MS spectrum of doubly charged species of NIVTPR*TPPPSQGK (residue 91-104) (SEQ ID NO: 9) at m/z 746.91. FIG. 1B: extracted ion chromatogram of doubly charged species of NIVTPR*TPPPSQGK (SEQ ID NO: 9) and NIVTPRTPPPSQGK (SEQ ID NO: 8). *: Likely Q deamination occurred for the peptide NIVTPRTPPPSQ GK (SEQ ID NO: 8). FIG. 1C: high resolution MS spectrum of double charged species of NIVTPRTPPPSQ GK (SEQ ID NO: 8). FIG. 1D: high resolution MS spectrum of double charged species of NIVTPR*TPPPSQ GK (SEQ ID NO: 9).

FIG. 2A: LTQ MS/MS spectrum of doubly charged species of PGFGYGGR*ASDYK (residue 122-134) (SEQ ID NO: 11) at m/z 688.32. FIG. 2B: extracted ion chromatogram of doubly charged species of PGFGYGGR*ASDYK (residues 122-134) (SEQ ID NO: 11) and PGFGYGGRASDYK (SEQ ID NO: 10).

FIG. 3A: Panel A: LTQ MS/MS spectrum of triply charged species of DGHHAAR*TTHYGSLPQK (residue 57-73) (SEQ ID NO: 13) at m/z 626.31. FIG. 3B: Panel B: extracted ion chromatogram of triply charged species of DGHHAARTTHYG-SLPQK (residues 122-134) (SEQ ID NO: 12) and DGHHAAR*TTHYGSLPQK (SEQ ID NO: 13).

FIG. 4 shows the amino acid sequence alignment for bovine NRGN and human NRGN. The underline indicates the peptides observed in tryptic digests. The initial Met (1)

is removed when the protein is translated, but is included in the numbering of the peptides. Shaded area indicated sequence difference of bovine and human NRGN. R68 (in bold, larger font) is the citrullination site in endogenous NRGN.

Figure 5A:
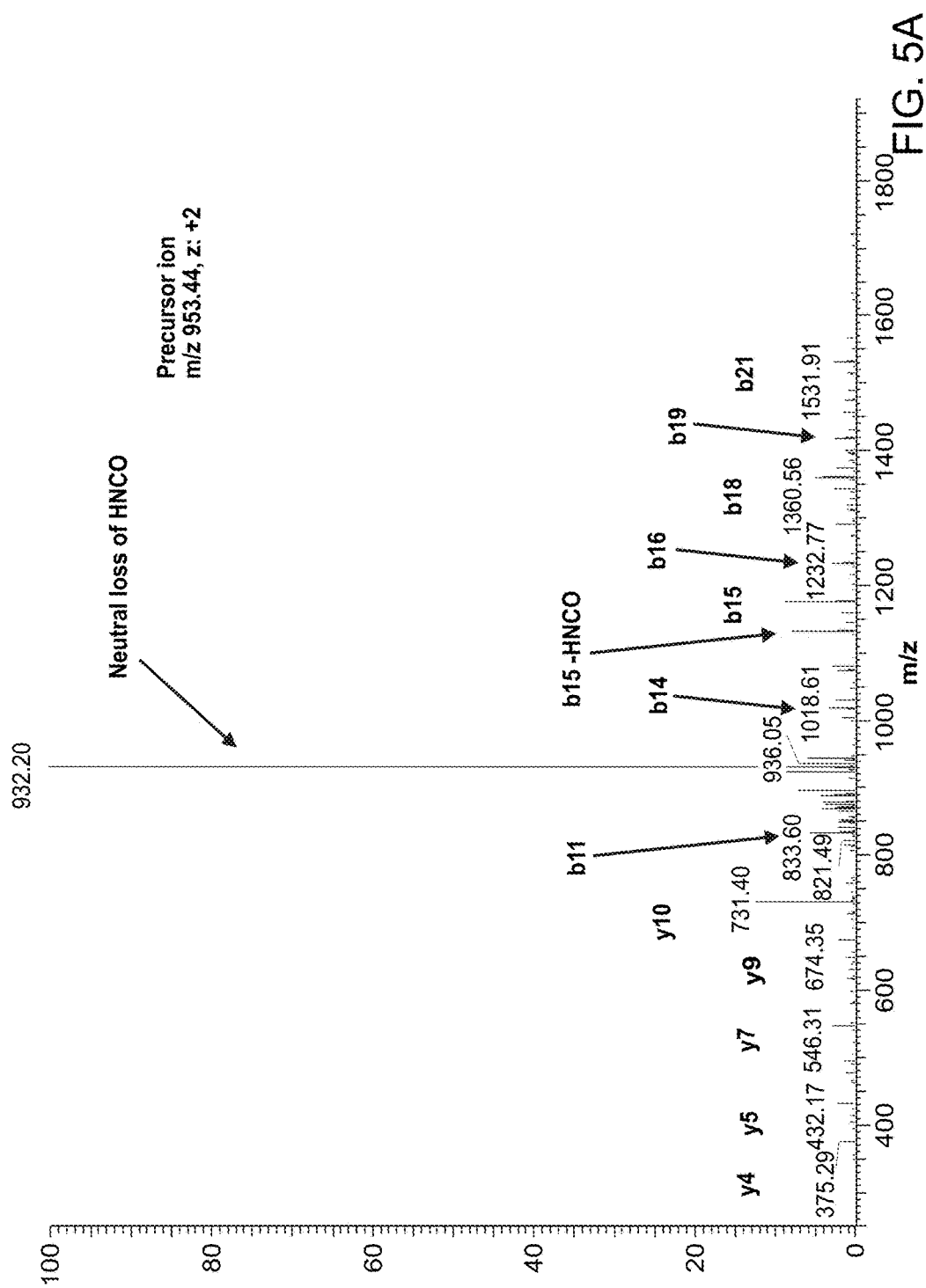
Figure 5B:
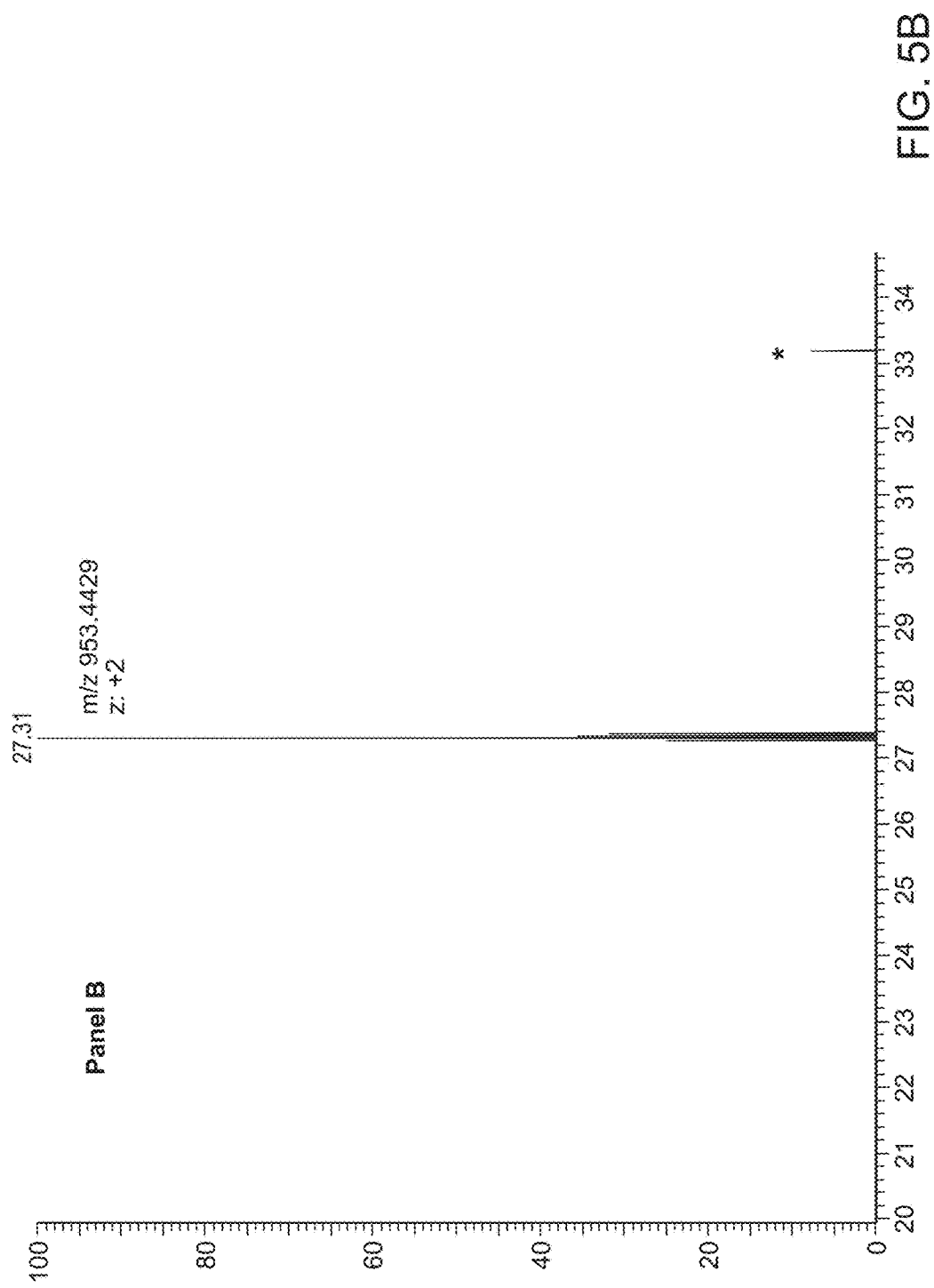

FIGS. 5A and 5B present MS/MS spectra and extracted ion chromatograms of a citrullinated tryptic peptide of bovine neurogranin. FIG. 5A: MS/MS spectrum of doubly charged species of KGPGPGGPGGAGGAR*GGAGGGPSGD (residues 54-78) (SEQ ID NO: 24) at m/z 953.44. FIG. 5B: extracted ion chromatogram of the ion m/z 953.44.

Figure 6B:
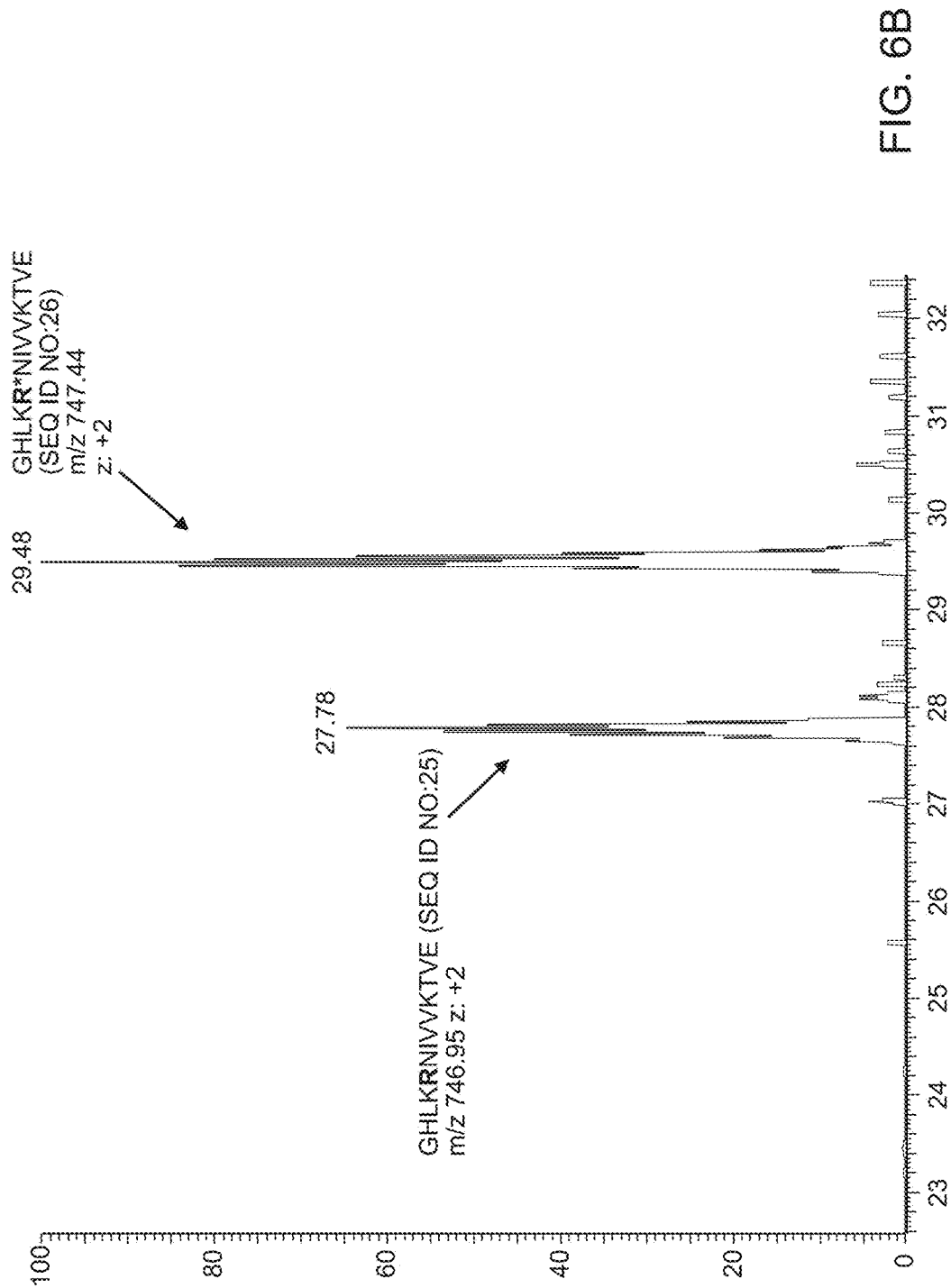

FIGS. 6A and 6B show MS/MS spectra and extracted ion chromatograms of citrullinated peptide of endogenous bovine GFAP digested with Glu-C. FIG. 6A: LTQ MS/MS spectrum of doubly charged species of GHLKR*NIVVKTVE (residues 398-410) (SEQ ID NO: 26) at m/z 747.44. FIG. 6B: extracted ion chromatogram of doubly charged species of GHLKR*NIVVKTVE (SEQ ID NO: 26) and GHLKRNIVVKTVE (SEQ ID NO: 25).

Figure 7A:
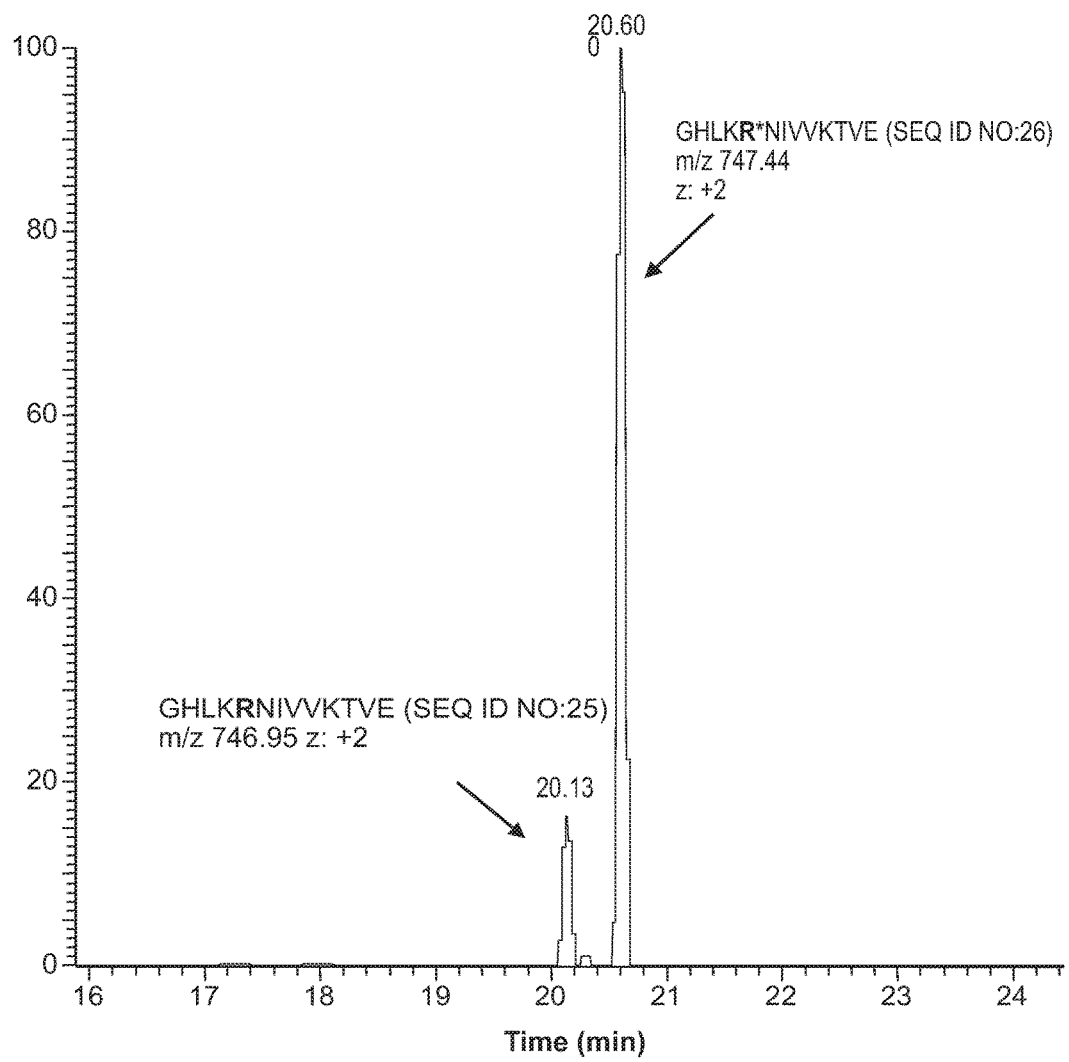
Figure 7B:
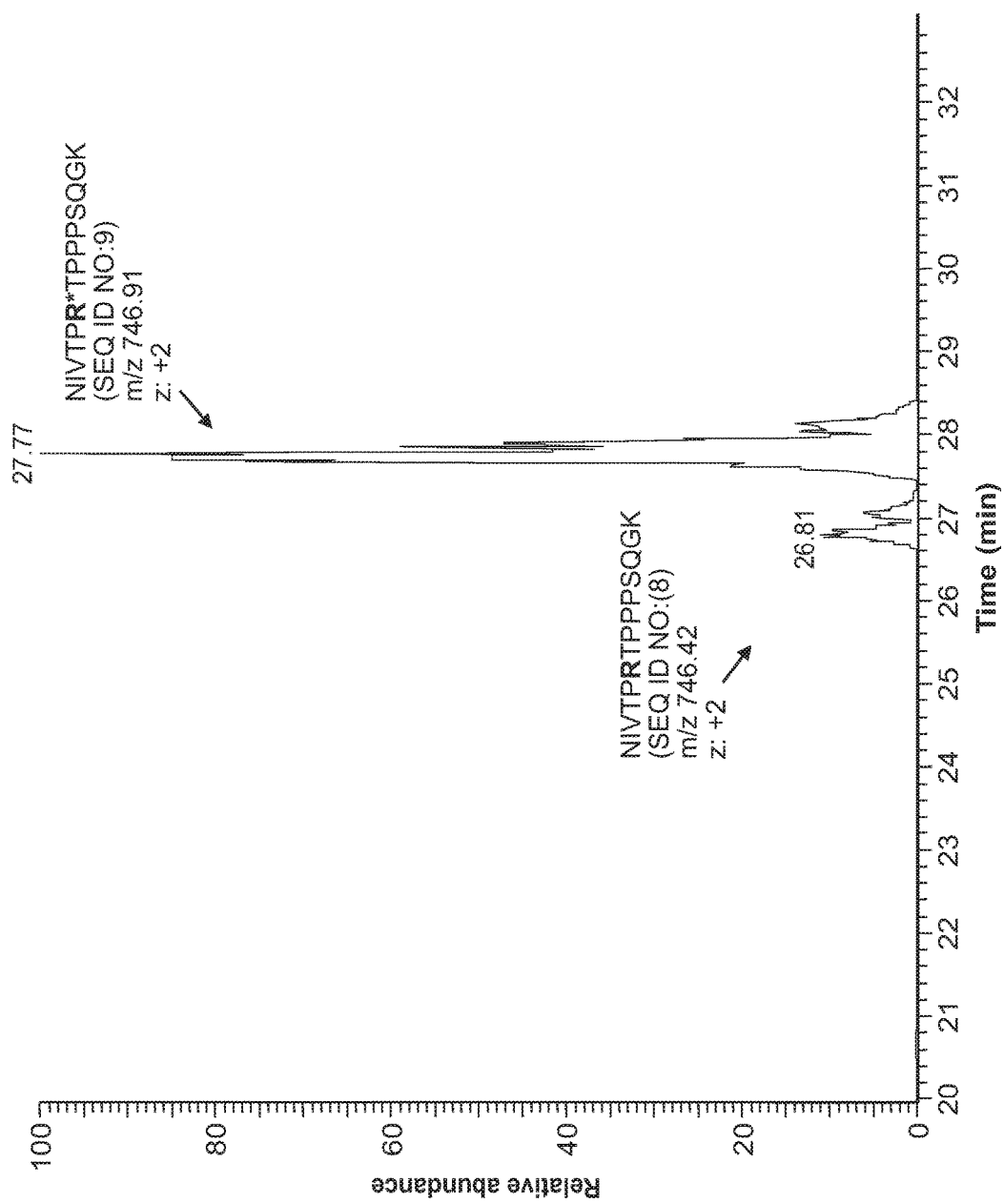

FIGS. 7A and 7B show extracted ion chromatograms of citrullinated peptide in an endogenous human GFAP sample. FIG. 7A: extracted ion chromatogram of doubly charged species of GHLKR*NIVVKTVE (residues 402-414) (SEQ ID NO: 30) and GHLKRNIVVKTVE (SEQ ID NO: 29) of human GFAP. FIG. 7B: extracted ion chromatogram of doubly charged species of NIVTPR*TPPPSQGK (residues 92-105) (SEQ ID NO: 32) and NIVTPRTPPPSQGK (SEQ ID NO: 31) of human MBP isoform 5.

FIG. 8 shows the amino acid sequence of recombinant human protein NRGN (SEQ ID NO: 161). The initial Met (1) is removed when the protein is translated but is included in the numbering of this protein. Shaded amino acids at N-terminus, T79, and R80 were introduced during subcloning. Shaded amino acids at N-terminus were not included in the numbering of this protein. The underline indicates the peptides identified in Lys-C digests and dotted line shows the peptide observed in Glu-C digests. Endogenous citrullination site was marked in italics. New citrullination sites observed after PAD2 treatment were in bold, larger font.

Figure 9A:
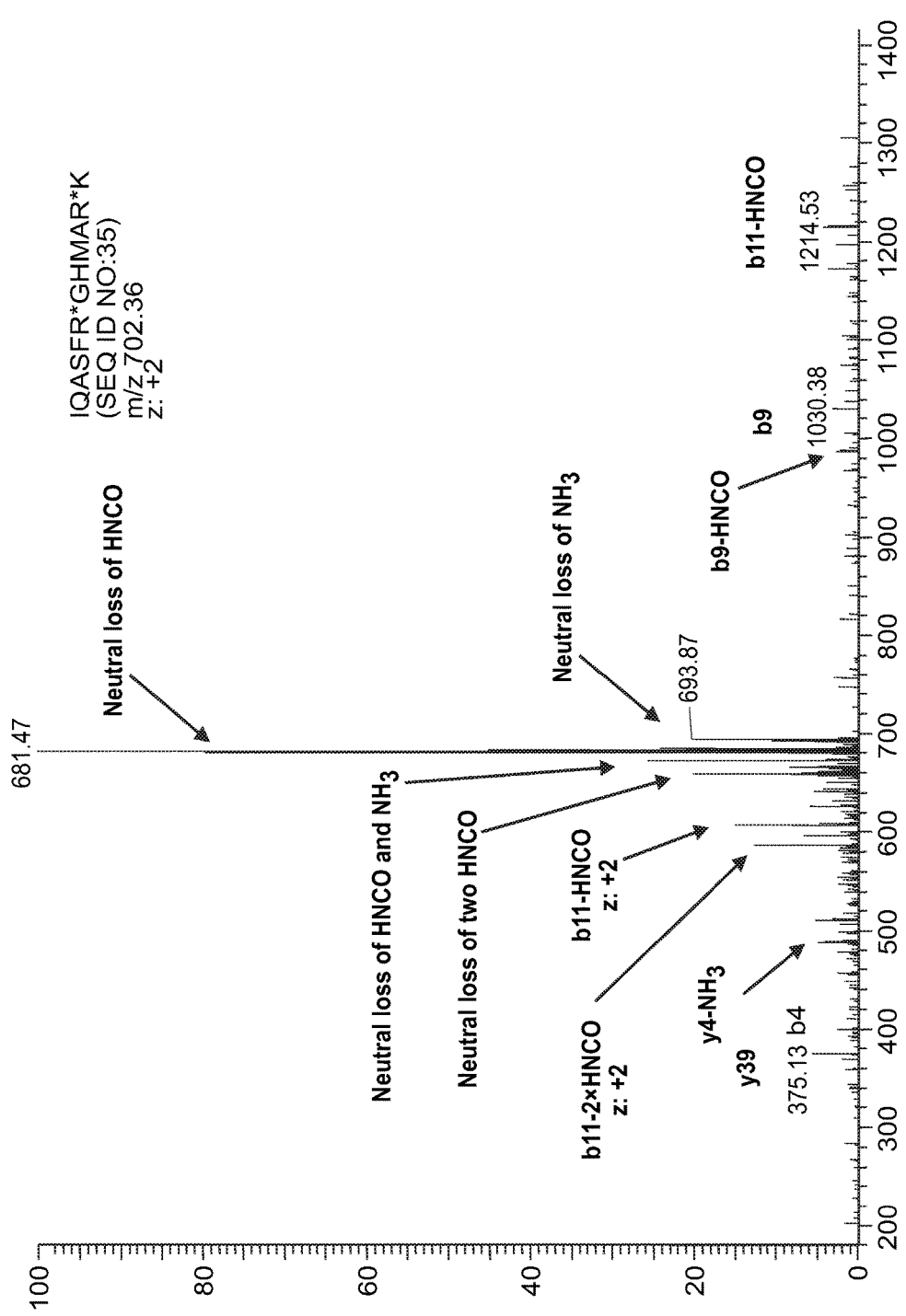
Figure 9B:
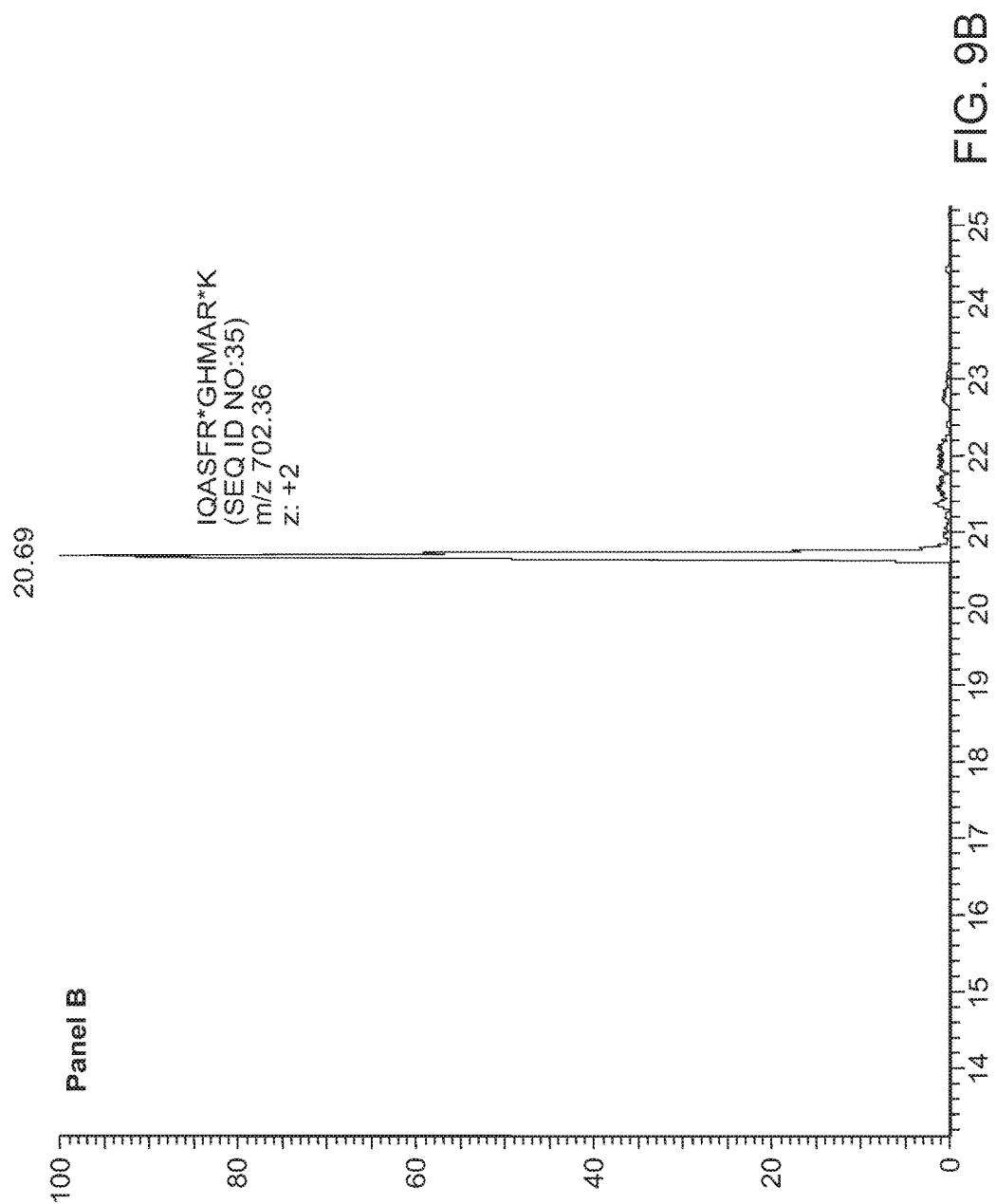

FIGS. 9A and 9B present MS/MS spectra and extracted ion chromatograms of a citrullinated peptide IQASFR*GHMAR*K (SEQ ID NO:101) of recombinant human protein NRGN after PAD2 treatment and digestion with Lys-C. FIG. 9A: LTQ MS/MS spectrum of doubly charged species of IQASFR*GHMAR*K (residues 33-44) (SEQ ID NO:101) at m/z 702.36. FIG. 9B: extracted ion chromatogram of doubly charged species of IQASFR*GHMAR*K (SEQ ID NO:101).

FIG. 10 shows the amino acid sequence of human GFAP and identified peptides with citrullination sites. The underline indicates the modified peptides in Lys-C digests. The dotted line indicates modified peptide in Glu-C digests. The initial Met (1) is removed when the protein is translated but is included in the numbering of the protein. Endogenous citrullination site was marked with an arrow and citrullination sites observed after PAD2 treatment were in italicized, bold, larger font.

FIG. 11 presents the aligned amino acid sequence of the isoform 5 (18.5 kDa, 170 residues) of human MBP (SEQ ID NO:162) and bovine MBP (169 amino acids) (SEQ ID NO:5). The initial Met (1) is removed in the numbering of both proteins. The underline indicated the peptide observed in Lys-C digests and dotted line showed the peptides observed in tryptic digests. Double-headed black arrows indicate citrullination sites previously reported in bovine MBP. Black arrows indicate citrullination sites previously reported in human MBP. Dotted arrows are previously identified citrullination sites in human MBP after PAD4 treatment. For all citrullinated residues identified in this study, endogenous citrullination sites were marked in grey shading and citrullination sites observed after PAD2 treatment were in italicized, bold larger font.

Figure 12A:
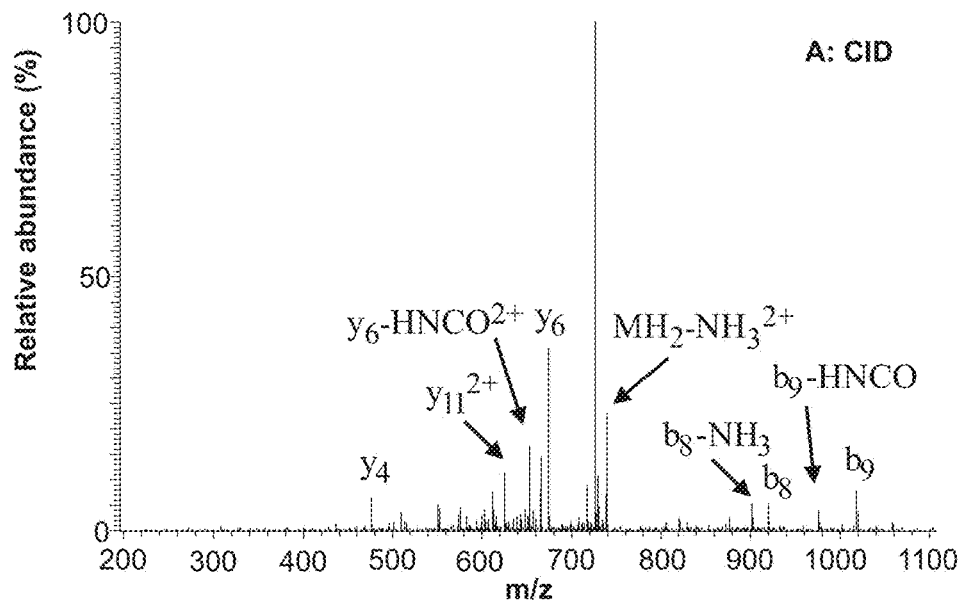
Figure 12B:
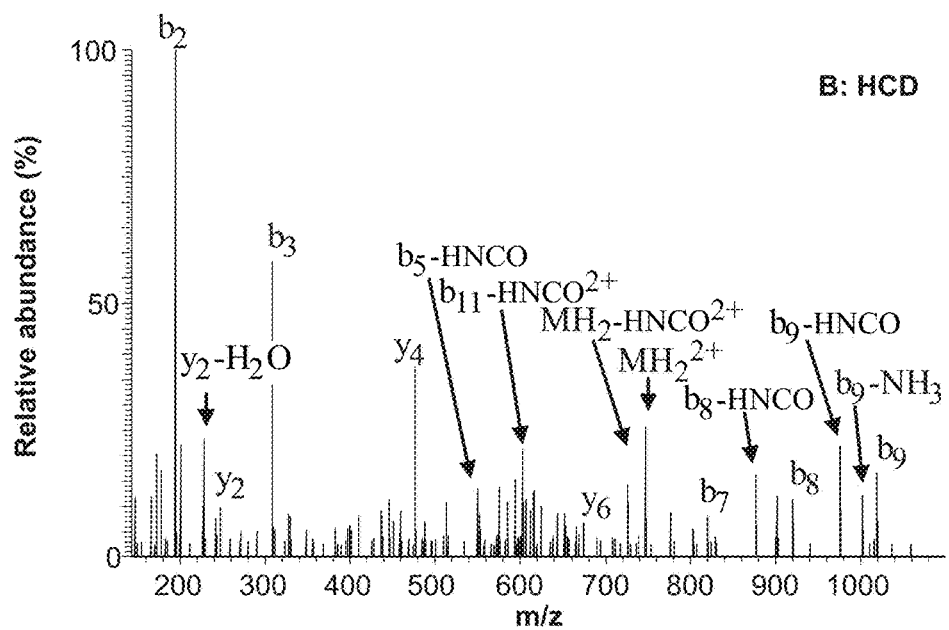

FIGS. 12A and 12B present a comparison of CID and HCD spectra of a citrullinated peptide of human GFAP in Glu-C digests. FIG. 12A: CID spectrum of the citrullinated peptide, GHLKR*NIVVKTVE (SEQ ID NO: 30) of human GFAP at m/z 747.44, z: +2; FIG. 12B: HCD spectrum of this citrullinated peptide at m/z 747.44.

Figures 13A, 13B, 13C:
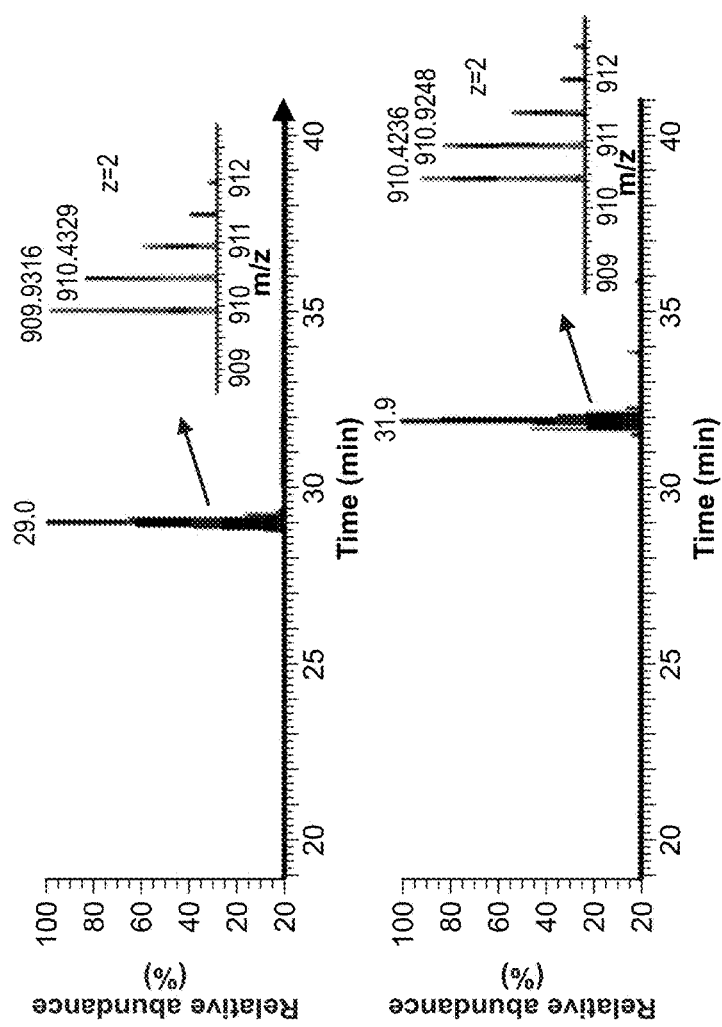

FIGS. 13A-13C present extracted ion chromatograms of the in vivo citrullinated peptide and intact peptide of NRGN in Lys-C digests of the AD3 brain sample. FIG. 13A: HPLC peak of the unmodified peptide at m/z 909.9275 with mass tolerance of 10 ppm. Right: isotopic clusters of the +2 ion. FIG. 13B: HPLC peak of the citrullinated peptide at m/z 910.4195 with mass tolerance of 10 ppm. Right: isotopic clusters of the +2 ion. FIG. 13C: Overlap of HPLC peaks shown in FIGS. 13A and 13B. From integrated peak area, occupancy rate of citrullinated peptide at R68 residue was 8.6% for the AD3 sample.

Figure 14:
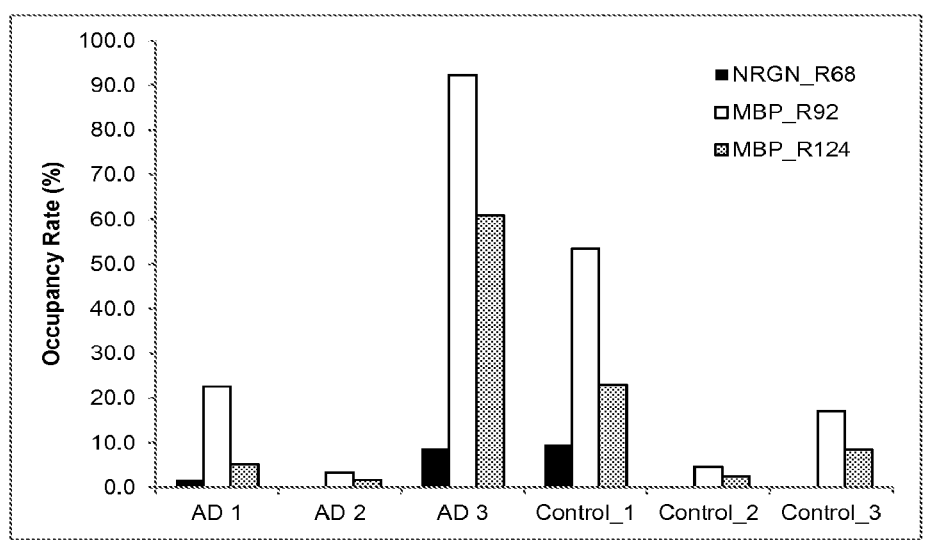

FIG. 14: Citrullination occupancy rate for NRGN at R68, MBP at R92 and R124. Occupancy rate was calculated based on integrated peak area of citrullinated peptide vs. the sum of citrullinated and intact peptides.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Brain and spinal cord (central nervous system, CNS) injury takes many forms, including hemorrhagic or ischemic stroke, hypoxic-ischemic encephalopathy, traumatic, mass effect compression from tumors or indolent as with degenerative brain diseases. Release or secretion of proteins from cells of the injured CNS can be useful for diagnostic/ prognostic assessment of patient viability, recovery and the effects of therapy to stabilize or prevent new or recurrent CNS injury in children and adults. It can also reflect compromise of the brain blood barrier. Thus detection of circulating CNS proteins in body fluids, including the peripheral blood, saliva, urine and CSF, could improve the diagnostic accuracy of CNS injury by identifying children and adults with subclinical and overt CNS injury. This can provide insight into stroke, brain injury following surgery or with life support, following trauma as well as providing the means to determine and validate new and existing CNS injury treatments for efficacy to improve outcomes. In addition to brain specificity for a circulating protein to identify brain injury, are specific protein post-translational modifications of brain proteins to increase the diagnostic specificity of acute brain injury. The present inventors have discovered that certain brain proteins are post-translationally modified. Such proteins include neurogranin (gene symbol: NRGN, Uniprot accession: Q92686), myelin basic protein (gene symbol: MBP, Uniprot accession: P02686) and glial fibrillary acidic protein (gene symbol GFAP, Uniprot accession: P14136), tubulin beta-4B chain, tubulin alpha-1B chain, CNPase, PPIA, Septin-7, Elongation factor1-alpha2, TPPP, TPPP3, Ermin Isoform 2, and NDRG2 Isoform 2. They discovered that NRGN and GFAP are endogenously citrullinated on specific arginines and citrullinated on additional arginines that were identified in vitro in proteins treated by the enzyme peptidyl arginine deiminase, PAD. PADs are calcium-activated enzymes that deiminate arginine residues when they are part of a protein creating a citrulline moiety in the place of the specific arginine residue. The ratio of citrullinated and unmodified forms of NRGN, MBP and GFAP (or fragments) can be quantitated multiple ways including antibody and aptamer based approaches. As well, mass spectrometry based methods can be used and the present inventors have developed specific quantitative multiple reaction monitoring assays for modified and unmodified peptides representing the total (unmodified) protein concentration, and each potential citrullinated residue. The value that quantitation of citrulline modification adds to detection of brain specific proteins is that it provides a window into the biology of the injured brain. The calcium burst necessary to increase PAD activity is a consequence of CNS cell injury. Quantifying the amount of the degree of citrullination provides insights into the scale, timing and recovery of injury that is critical to personalizing and developing new therapies appropriate to the phase of injury/recovery. In addition, citrullination of some proteins is known to increase their antigenicity, thus identification of citrullinated brain proteins may be very important for diagnosis of chronic neurodegenerative diseases such as Alzheimer's disease, multiple sclerosis and Parkinson's Disease. Detection and quantification of autoantibodies to these modified proteins could also be used to assess long term brain injury. Taken together, assays of post-translation modifications or the ratio of modified to unmodified at one or more specific arginine residues of circulating brain proteins will provide more accurate and specific diagnostic information for diagnosing brain injury.

I. Definitions

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, equines, bovines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies.

As used herein, the term "antigen" is generally used in reference to any substance that is capable of reacting with an antibody. It is intended that this term encompass any antigen and "immunogen" (i.e., a substance which induces the formation of antibodies). Thus, in an immunogenic reaction, antibodies are produced in response to the presence of an antigen (immunogen) or portion of an antigen. More specifically, the terms are used herein to describe an antigen that elicits a humoral and/or cellular immune response (i.e., is immunogenic), such that administration of the immunogen to an animal (e.g., via a vaccine) mounts an antigen-specific immune response against the same or similar antigens that are encountered within the tissues of the animal. In another embodiment, when it is desirable to suppress an immune response against a given antigen, an antigen may comprise a toleragen.

As used herein, the term "autoantibodies" refers to antibodies that are capable of reacting against an antigenic constituent of an individual's own tissue or cells (e.g., the antibodies recognize and bind to "self" antigens). In certain embodiments, the term "neurogranin autoantibodies" refers to antibodies produced by an individual that are immunospecific to the individual's own neurogranin protein. In other embodiments, the term "citrullinated neurogranin autoantibodies" or "cit-neurogranin autoantibodies" refers to antibodies produced by an individual that are immunospecific to the individual's own citrullinated neurogranin protein.

The term "brain injury" refers to a condition in which the brain is damaged by injury caused by an event. As used herein, an "injury" is an alteration in cellular or molecular integrity, activity, level, robustness, state, or other alteration that is traceable to an event. For example, an injury includes a physical, mechanical, chemical, biological, functional, infectious, or other modulator of cellular or molecular characteristics. An event can include a physical trauma such as a single or repetitive impact (percussive) or a biological abnormality such as a stroke resulting from either blockade or leakage of a blood vessel. An event is optionally an infection by an infectious agent. A person of skill in the art recognizes numerous equivalent events that are encompassed by the terms injury or event.

More specifically, the term "brain injury" refers to a condition that results in central nervous system damage, irrespective of its pathophysiological basis. Among the most frequent origins of a "brain injury" are stroke and traumatic brain injury (TBI). A "stroke" is classified into hemorrhagic and non-hemorrhagic. Examples of hemorrhagic stroke include cerebral hemorrhage, subarachnoid hemorrhage, and intracranial hemorrhage secondary to cerebral arterial malformation, while examples of non-hemorrhagic stroke include cerebral infarction.

The term "traumatic brain injury" or "TBI" refer to traumatic injuries to the brain which occur when physical trauma causes brain damage. For example, TBI can result from a closed head injury or a penetrating head injury. A "non-traumatic brain injury" refers to brain injuries that do not involve ischemia or external mechanical force (e.g., stroke, Alzheimer's disease, Parkinson's disease, Huntington's disease, multiple sclerosis, amyotrophic lateral sclerosis, brain hemorrhage, brain infections, brain tumor, among others).

The term "brain injury" also refers to subclinical brain injury, spinal cord injury, and anoxic-ischemic brain injury. The term "subclinical brain injury" (SCI) refers to brain injury without overt clinical evidence of brain injury. A lack of clinical evidence of brain injury when brain injury actually exists could result from degree of injury, type of injury, level of consciousness, medications particularly sedation and anesthesia.

The "spinal cord injury" refers to a condition in which the spinal cord receives compression/detrition due to a vertebral fracture or dislocation to cause dysfunction. As used herein, the term "anoxic-ischemic brain injury" refers to deprivation of oxygen supply to brain tissue resulting in compromised brain function and includes cerebral hypoxia. For example, anoxic-ischemic brain injury includes focal cerebral ischemia, global cerebral ischemia, hypoxic hypoxia (i.e., limited oxygen in the environment causes reduced brain function, such as with divers, aviators, mountain climbers, and fire fighters, all of whom are at risk for this kind of cerebral hypoxia), obstructions in the lungs (e.g., hypoxia resulting from choking, strangulation, the crushing of the windpipe).

The term "brain injury biomarker" (BIB), "brain injury biomarker protein", "brain injury biomarker peptide", brain injury biomarker polypeptide" and the like refer to a protein, including those described herein, that can be used in a method of the present invention, e.g., to diagnose brain injury in a patient. Brain injury biomarker proteins include, but are not limited to, neurogranin (NRGN), glial fibrillary acidic protein (GFAP) and myelin basic protein (MBP). The term further includes, but is not limited to, PAD-2, tubulin beta-4B chain, tubulin alpha-1B chain, CNPase, PPIA, Septin-7, Elongation factor1-alpha2, TPPP, TPPP3, Ermin Isoform 2, NDRG2 Isoform 2astrotactin 1 (ASTN1), brain angiogenesis inhibitor 3 (BAI3); carnosine dipeptidase 1 (CNDP1); ERMIN; glutamate receptor metabotropic 3 (GRM3); kelch-like protein 32 (KLH32); melanoma antigen family E,2 (MAGE2); neuregulin 3 (NRG3); oligodendrocyte myelin glycoprotein (OMG); solute carrier family 39 (zinc transporter); reticulon 1 (RTN1); and peptidylarginine deiminase (types 1-4 and 6) (PAD). The term also includes other brain injury biomarker proteins known in the art. In addition, the term "brain injury biomarkers" also includes the isoforms and/or post-translationally modified forms of any of the foregoing. In further embodiments, the term includes autoantibodies to the foregoing. The present invention contemplates the detection, measurement, quantification, determination and the like of both unmodified and modified (e.g., citrullination or other post-translational modification) proteins/polypeptides/peptides as well as autoantibodies to any of the foregoing. In certain embodiments, it is understood that reference to the detection, measurement, determination, and the like, of a biomarker refers detection of the protein/polypeptide/peptide (modified and/or unmodified). In other embodiments, reference to the detection, measurement, determination, and the like, of a biomarker refers detection of autoantibodies of the protein/polypeptide/peptide.

As used herein, the term "comparing" refers to making an assessment of how the proportion, level or cellular localization of one or more biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample. More specifically, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels/ratios that correspond to, for example, a patient having brain injury, not having brain injury, is responding to treatment for brain injury, is not responding to treatment for brain injury, is/is not likely to respond to a particular brain injury treatment, or having/not having another disease or condition. In a specific embodiment, the term "comparing" refers to assessing whether the level of one or more biomarkers of the present invention in a sample from a patient is the same as, more or less than, different from other otherwise correspond (or not) to levels/ratios of the same biomarkers in a control sample (e.g., predefined levels/ratios that correlate to uninfected individuals, standard brain injury levels/ratios, etc.).

In another embodiment, the term "comparing" refers to making an assessment of how the proportion, level or cellular localization of one or more biomarkers in a sample from a patient relates to the proportion, level or cellular localization of another biomarker in the same sample. For example, a ratio of one biomarker to another from the same patient sample can be compared. In another embodiment, a level of one biomarker in a sample (e.g., a post-translationally modified biomarker protein) can be compared to the level of the same biomarker (e.g., unmodified biomarker protein) in the sample. In a specific embodiment, the proportion of a citrullinated biomarker protein can be compared to the unmodified protein, both of which are measured in the same patient sample. Ratios of modified:unmodified biomarker proteins can be compared to other protein ratios in the same sample or to predefined reference or control ratios.

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient has a brain injury or is suffering from neurodegeneration. In specific embodiments, the parameter may comprise the level of one or more biomarkers of the present invention. A particular set or pattern of the amounts of one or more biomarkers may indicate that a patient has a brain injury (i.e., correlates to a patient having brain injury). In other embodiments, a correlation could be the ratio of a post-translationally modified protein to the unmodified protein indicates (or a change in the ratio over time or as compared to a reference/control ratio) could mean that the patient has a brain injury). In specific embodiments, a correlation could be the ratio of a citrullinated peptide to the non-citrullinated form, or any other combination in which a change in one peptide causes or is accompanied by a change in another.

In other embodiments, a particular set or pattern of the amounts of one or more biomarkers may be correlated to a patient being unaffected (i.e., indicates a patient does not have brain injury). In certain embodiments, "indicating," or "correlating," as used according to the present invention, may be by any linear or non-linear method of quantifying the relationship between levels/ratios of biomarkers to a standard, control or comparative value for the assessment of the diagnosis, prediction of brain injury or brain injury progression, assessment of efficacy of clinical treatment, identification of a patient that may respond to a particular treatment regime or pharmaceutical agent, monitoring of the progress of treatment, and in the context of a screening assay, for the identification of an anti-brain injury therapeutic.

The terms "patient," "individual," or "subject" are used interchangeably herein, and refer to a mammal, particularly, a human. The patient may have mild, intermediate or severe disease. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining a patient sample and/or detecting the level of a biomarker(s) in a sample. In one embodiment, the terms refer to obtaining a patient sample and detecting the level of one or more biomarkers in the sample. In another embodiment, the terms "measuring" and "determining" mean detecting the level of one or more biomarkers in a patient sample. Measuring can be accomplished by methods known in the art and those further described herein. The term "measuring" is also used interchangeably throughout with the term "detecting."

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of brain injury. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cerebrospinal fluid, urine, saliva, stool and synovial fluid), solid tissue samples such as a biopsy specimen or tissue cultures or cells derived therefrom and the progeny thereof. In certain embodiment, a sample comprises cerebrospinal fluid. In a specific embodiment, a sample comprises a blood sample. In another embodiment, a sample comprises a plasma sample. In yet another embodiment, a serum sample is used.

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

The terms "specifically binds to," "specific for," and related grammatical variants refer to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the present invention may be assayed for levels/ratios in a sample from an unaffected individual (UI) or a normal control individual (NC) (both terms are used interchangeably herein). In another embodiment, a "suitable control" or "appropriate control" is a value, level, feature, characteristic, property, ratio, etc. determined prior to performing a therapy (e.g., a brain injury treatment) on a patient. In yet another embodiment, a transcription rate, mRNA level, translation rate, protein level/ratio, biological activity, cellular characteristic or property, genotype, phenotype, etc., can be determined prior to, during, or after administering a therapy into a cell, organ, or patient. In a further embodiment, a "suitable control" or "appropriate control" is a predefined value, level, feature, characteristic, property, ratio, etc. A "suitable control" can be a profile or pattern of levels/ratios of one or more biomarkers of the present invention that correlates to brain injury, to which a patient sample can be compared. The patient sample can also be compared to a negative control, i.e., a profile that correlates to not having brain injury.

II. Detection of Brain Injury or Neurodegeneration Biomarkers

A. Detection by Mass Spectrometry

In one aspect, the biomarkers of the present invention may be detected by mass spectrometry, a method that employs a mass spectrometer to detect gas phase ions. Examples of mass spectrometers are time-of-flight, magnetic sector, quadrupole filter, ion trap, ion cyclotron resonance, Orbitrap, hybrids or combinations of the foregoing, and the like.

In particular embodiments, the biomarkers of the present invention are detected using selected reaction monitoring (SRM) mass spectrometry techniques. Selected reaction monitoring (SRM) is a non-scanning mass spectrometry technique, performed on triple quadrupole-like instruments and in which collision-induced dissociation is used as a means to increase selectivity. In SRM experiments two mass analyzers are used as static mass filters, to monitor a particular fragment ion of a selected precursor ion. The specific pair of mass-over-charge (m/z) values associated to the precursor and fragment ions selected is referred to as a "transition" and can be written as parent m/z→fragment m/z (e.g. 673.5→534.3). Unlike common MS based proteomics, no mass spectra are recorded in a SRM analysis. Instead, the detector acts as counting device for the ions matching the selected transition thereby returning an intensity distribution over time. Multiple SRM transitions can be measured within the same experiment on the chromatographic time scale by rapidly toggling between the different precursor/fragment pairs (sometimes called multiple reaction monitoring, MRM). Typically, the triple quadrupole instrument cycles through a series of transitions and records the signal of each transition as a function of the elution time. The method allows for additional selectivity by monitoring the chromatographic coelution of multiple transitions for a given analyte. The terms SRM/MRM are occasionally used also to describe experiments conducted in mass spectrometers other than triple quadrupoles (e.g. in trapping instruments) where upon fragmentation of a specific precursor ion a narrow mass range is scanned in MS2 mode, centered on a fragment ion specific to the precursor of interest or in general in experiments where fragmentation in the collision cell is used as a means to increase selectivity. In this application the terms SRM and MRM or also SRM/MRM can be used interchangeably, since they both refer to the same mass spectrometer operating principle. As a matter of clarity, the term MRM is used throughout the text, but the term includes both SRM and MRM, as well as any analogous technique, such as e.g. highly-selective reaction monitoring, hSRM, LC-SRM or any other SRM/MRM-like or SRM/MRM-mimicking approaches performed on any type of mass spectrometer and/or, in which the peptides are fragmented using any other fragmentation method such as e.g. CAD (collision-activated dissociation (also known as CID or collision-induced dissociation), HCD (higher energy CID), ECD (electron capture dissociation), PD (photodissociation) or ETD (electron transfer dissociation).

In another specific embodiment, the mass spectrometric method comprises matrix assisted laser desorption/ionization time-of-flight (MALDI-TOF MS or MALDI-TOF). In another embodiment, method comprises MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein.

In an alternative embodiment, the mass spectrometric technique comprises surface enhanced laser desorption and ionization or "SELDI," as described, for example, in U.S. Pat. Nos. 6,225,047 and 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes comprising energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the present invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

B. Detection by Immunoassay

In other embodiments, the biomarkers of the present invention can be detected and/or measured by immunoassay. Immunoassay requires biospecific capture reagents, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art.

The present invention contemplates traditional immunoassays including, for example, sandwich immunoassays including ELISA or fluorescence-based immunoassays, immunoblots, Western Blots (WB), as well as other enzyme immunoassays. Nephelometry is an assay performed in liquid phase, in which antibodies are in solution. Binding of the antigen to the antibody results in changes in absorbance, which is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

Although antibodies are useful because of their extensive characterization, any other suitable agent (e.g., a peptide, an aptamer, or a small organic molecule) that specifically binds a biomarker of the present invention is optionally used in place of the antibody in the above described immunoassays. For example, an aptamer that specifically binds all neurogranin and/or one or more of its breakdown products might be used. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

C. Detection by Electrochemiluminescent Assay

In several embodiments, the biomarker biomarkers of the present invention may be detected by means of an electrochemiluminescent assay developed by Meso Scale Discovery (Gaithersburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. Nos. 7,497,997; 7,491,540; 7,288,410; 7,036,946; 7,052,861; 6,977,722; 6,919,173; 6,673,533; 6,413,783; 6,362,011; 6,319,670; 6,207,369; 6,140,045; 6,090,545; and 5,866,434. See also U.S. Patent Applications Publication No. 2009/0170121; 2009/006339; 2009/0065357; 2006/0172340; 2006/0019319; 2005/0142033; 2005/0052646;

2004/0022677; 2003/0124572; 2003/0113713; 2003/0003460; 2002/0137234; 2002/0086335; and No. 2001/0021534.

D. Other Methods for Detecting Biomarkers

The biomarkers of the present invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Furthermore, a sample may also be analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Invitrogen Corp. (Carlsbad, Calif.), Affymetrix, Inc. (Fremong, Calif.), Zyomyx (Hayward, Calif.), R&D Systems, Inc. (Minneapolis, Minn.), Biacore (Uppsala, Sweden) and Procognia (Berkshire, UK). Examples of such protein biochips are described in the following patents or published patent applications: U.S. Pat. Nos. 6,537,749; 6,329,209; 6,225,047; 5,242,828; PCT International Publication No. WO 00/56934; and PCT International Publication No. WO 03/048768.

III. Determination of a Patient's Brain Injury Status

A. The present invention relates to the use of biomarkers to diagnose brain injury or neurodegeneration. It is understood that, for the sake of brevity, the term "brain injury" is used throughout the specification, but it is understood that the methods and biomarkers described herein are applicable in the context of diagnosing neurodegeneration. More specifically, the biomarkers of the present invention can be used in diagnostic tests to determine, qualify, and/or assess brain injury or status, for example, to diagnose brain injury, in an individual, subject or patient. In particular embodiments, brain injury status can include determining a patient's brain injury status or brain injury status, for example, to diagnose brain injury, in an individual, subject or patient. More specifically, the biomarkers to be detected in diagnosing brain injury (e.g., subclinical brain injury) include, but are not limited to, MBP, GFAP, tubulin beta-4B chain, tubulin alpha-1B chain, CNPase, PPIA, Septin-7, Elongation factor1-alpha2, TPPP, TPPP3, Ermin Isoform 2, NDRG2 Isoform 2, astrotactin 1 (ASTN1), brain angiogenesis inhibitor 3 (BAI3); carnosine dipeptidase 1 (CNDP1); ERMIN; glial fibrillary acidic protein (GFAP); glutamate receptor metabotropic 3 (GRM3); kelch-like protein 32 (KLH32); melanoma antigen family E,2 (MAGE2); neuregulin 3 (NRG3); neurogranin (NRGN); oligodendrocyte myelin glycoprotein (OMG); solute carrier family 39 (zinc transporter), member 12 (SLC39A12); reticulon 1 (RTN1); metallothionein (MT3), and peptidylarginine deiminase type-2 (PAD2). Tables 1-11 and 13-17 also list biomarkers (i.e., peptides) useful in the methods of the present invention. Other biomarkers known in the relevant art may be used in combination with the biomarkers described herein. The present invention further contemplates the detection, measurement, quantification, determination and the like of both unmodified and modified (e.g., citrullination or other post-translational modification) proteins/polypeptides/peptides as well as autoantibodies to any of the foregoing, determining a patient's brain injury status.

B. Biomarker Panels

The biomarkers of the present invention can be used in diagnostic tests to assess, determine, and/or qualify (used interchangeably herein) brain injury status in a patient. The phrase "brain injury status" includes any distinguishable manifestation of the condition, including not having brain injury. For example, brain injury status includes, without limitation, the presence or absence of brain injury in a patient, the risk of developing brain injury, the stage or severity of brain injury, the progress of brain injury (e.g., progress of brain injury over time) and the effectiveness or response to treatment of brain injury (e.g., clinical follow up and surveillance of brain injury after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different brain injury statuses of at least $p<0.05$, $p<10'$, $p<10^{-3}$, $p<10^{-4}$ or $p<10'$. Diagnostic tests that use these biomarkers may show an ROC of at least 0.6, at least about 0.7, at least about 0.8, or at least about 0.9.

The biomarkers can be differentially present in UI (NC or non-brain injury) and brain injury, and, therefore, are useful in aiding in the determination of brain injury status. In certain embodiments, the biomarkers are measured in a patient sample using the methods described herein and compared, for example, to predefined biomarker levels/ratios and correlated to brain injury status. In particular embodiments, the measurement(s) may then be compared with a relevant diagnostic amount(s), cut-off(s), or multivariate model scores that distinguish a positive brain injury status from a negative brain injury status. The diagnostic amount(s) represents a measured amount of a biomarker(s) above which or below which a patient is classified as having a particular brain injury status. For example, if the biomarker(s) is/are up-regulated compared to normal during brain injury, then a measured amount(s) above the diagnostic cutoff(s) provides a diagnosis of brain injury. Alternatively, if the biomarker(s) is/are down-regulated during brain injury, then a measured amount(s) at or below the diagnostic cutoff(s) provides a diagnosis of non-brain injury. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from patients with the different brain injury statuses, and drawing the cut-off to suit the desired levels of specificity and sensitivity.

In other embodiments, ratios of post-translationally modified biomarkers to the corresponding unmodified biomarkers are useful in aiding in the determination of brain injury status. In certain embodiments, the biomarker ratios are indicative of diagnosis. In other embodiments, a biomarker ratio can be compared to another biomarker ratio in the same sample or to a set of biomarker ratios from a control or reference sample.

Indeed, as the skilled artisan will appreciate there are many ways to use the measurements of two or more biomarkers in order to improve the diagnostic question under investigation. In a quite simple, but nonetheless often effective approach, a positive result is assumed if a sample is positive for at least one of the markers investigated.

Furthermore, in certain embodiments, the values measured for markers of a biomarker panel are mathematically combined and the combined value is correlated to the underlying diagnostic question. Biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating a biomarker combination of the present invention, e.g. to diagnose brain injury, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

C. Determining Risk of Developing Brain Injury

In a specific embodiment, the present invention provides methods for determining the risk of developing brain injury in a patient. Biomarker percentages, ratios, amounts or patterns are characteristic of various risk states, e.g., high, medium or low. The risk of developing brain injury is determined by measuring the relevant biomarkers and then either submitting them to a classification algorithm or comparing them with a reference amount, i.e., a predefined level or pattern of biomarkers that is associated with the particular risk level.

D. Determining Brain Injury Severity

In another embodiment, the present invention provides methods for determining the severity of brain injury in a patient. Each grade or stage of brain injury likely has a characteristic level of a biomarker or relative levels/ratios of a set of biomarkers (a pattern or ratio). The severity of brain injury is determined by measuring the relevant biomarkers and then either submitting them to a classification algorithm or comparing them with a reference amount, i.e., a predefined level or pattern of biomarkers that is associated with the particular stage.

E. Determining Brain Injury Prognosis

In one embodiment, the present invention provides methods for determining the course of brain injury in a patient. Brain injury course refers to changes in brain injury status over time, including brain injury progression (worsening) and brain injury regression (improvement). Over time, the amount or relative amount (e.g., the pattern or ratio) of the biomarkers changes. For example, biomarker "X" may be increased with brain injury, while biomarker "Y" may be decreased with brain injury. Therefore, the trend of these biomarkers, either increased or decreased over time toward brain injury or non-brain injury indicates the course of the condition. Accordingly, this method involves measuring the level of one or more biomarkers in a patient at least two different time points, e.g., a first time and a second time, and comparing the change, if any. The course of brain injury is determined based on these comparisons.

F. Patient Management

In certain embodiments of the methods of qualifying brain injury status, the methods further comprise managing patient treatment based on the status. Such management includes the actions of the physician or clinician subsequent to determining brain injury status. For example, if a physician makes a diagnosis of brain injury, then a certain regime of monitoring would follow. An assessment of the course of brain injury using the methods of the present invention may then require a certain brain injury therapy regimen. Alternatively, a diagnosis of non-brain injury might be followed with further testing to determine a specific disease that the patient might be suffering from. Also, further tests may be called for if the diagnostic test gives an inconclusive result on brain injury status.

G. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern, profile or ratio) of one or more of the biomarkers of the present invention may change toward a non-brain injury profile. Therefore, one can follow the course of one or more biomarkers in the patient during the course of treatment. Accordingly, this method involves measuring one or more biomarkers in a patient receiving drug therapy, and correlating the biomarker levels/ratios with the brain injury status of the patient (e.g., by comparison to predefined levels/ratios of the biomarkers that correspond to different brain injury statuses). One embodiment of this method involves determining the levels/ratios of one or more biomarkers for at least two different time points during a course of drug therapy, e.g., a first time and a second time, and comparing the change in levels/ratios of the biomarkers, if any. For example, the levels/ratios of one or more biomarkers can be measured before and after drug administration or at two different time points during drug administration. The effect of therapy is determined based on these comparisons. If a treatment is effective, then the level/ratio of one or more biomarkers will trend toward normal, while if treatment is ineffective, the level/ratio of one or more biomarkers will trend toward brain injury indications.

H. Generation of Classification Algorithms for Qualifying Brain Injury Status

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

IV. Kits for the Detection of Brain Injury Biomarkers

In another aspect, the present invention provides kits for qualifying brain injury status, which kits are used to detect the biomarkers described herein. In a specific embodiment, the kit is provided as an ELISA kit comprising antibodies to the biomarkers of the present invention including, but not limited to, MBP, GFAP, PAD-2, tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GFAP, GRM3, KLH32, MAGE2, NRG3, NRGN, OMG, SLC39A12, RTN1, MT3, and PAD2, as well as the peptides listed in Tables 1-11 and 13-17. In a specific embodiment, the antibodies specifically bind to the modified or unmodified forms of NRGN or peptides thereof.

The ELISA kit may comprise a solid support, such as a chip, microtiter plate (e.g., a 96-well plate), bead, or resin having biomarker capture reagents attached thereon. The kit may further comprise a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP.

The kit for qualifying brain injury status may be provided as an immuno-chromatography strip comprising a membrane on which the antibodies are immobilized, and a means for detecting, e.g., gold particle bound antibodies, where the membrane, includes NC membrane and PVDF membrane. The kit may comprise a plastic plate on which a sample application pad, gold particle bound antibodies temporally immobilized on a glass fiber filter, a nitrocellulose membrane on which antibody bands and a secondary antibody band are immobilized and an absorbent pad are positioned in a serial manner, so as to keep continuous capillary flow of blood serum.

In certain embodiments, a patient can be diagnosed by adding blood or blood serum from the patient to the kit and detecting the relevant biomarkers conjugated with antibodies, specifically, by a method which comprises the steps of: (i) collecting blood or blood serum from the patient; (ii) separating blood serum from the patient's blood; (iii) adding the blood serum from patient to a diagnostic kit; and, (iv) detecting the biomarkers conjugated with antibodies. In this method, the antibodies are brought into contact with the patient's blood. If the biomarkers are present in the sample, the antibodies will bind to the sample, or a portion thereof. In other kit and diagnostic embodiments, blood or blood serum need not be collected from the patient (i.e., it is already collected). Moreover, in other embodiments, the sample may comprise a tissue sample or a clinical sample.

The kit can also comprise a washing solution or instructions for making a washing solution, in which the combination of the capture reagents and the washing solution allows capture of the biomarkers on the solid support for subsequent detection by, e.g., antibodies or mass spectrometry. In a further embodiment, a kit can comprise instructions for suitable operational parameters in the form of a label or separate insert. For example, the instructions may inform a consumer about how to collect the sample, how to wash the probe or the particular biomarkers to be detected, etc. In yet another embodiment, the kit can comprise one or more containers with biomarker samples, to be used as standard(s) for calibration.

IV. Citrullinated Polypeptides

The present invention provides citrullinated polypeptides. As used herein, the terms "polypeptide," "peptide," and "protein" are used interchangeably herein to refer to polymers of amino acids of any length. Thus, peptides, oligopeptides, and proteins are included within the definition of polypeptide. This term also encompasses post expression modifications of the polypeptide, for example, glycosylations, acetylations, phosphorylations and the like. Included within the definition are, for example, polypeptides containing one or more analogues of an amino acid (including, for example, unnatural amino acids, etc.), polypeptides with substituted linkages, as well as other modifications known in the art, both naturally occurring and non-naturally occurring.

In a particular aspect, the citrullinated polypeptide sequences are human amino acid sequences. The present invention also encompasses both the full length amino acid sequences having at least one of the arginine amino acids converted to a citrulline, or fragments thereof. The limitation being that any fragment of any desired length has at least one citrulline that specifically binds to autoantibodies. Indeed, in a specific example, the present invention encompasses any NRGN peptide that is demonstrated to be a potential target of cit-NRGN auto antibodies in brain injury patients. The full length amino acid sequence for human NRGN is shown at SEQ ID NO:1. As a further example, the amino acid sequences for MBP, GFAP, and PAD-2 are shown in SEQ ID NOS:2-4, respectively. The amino acid sequences of the other biomarker proteins described herein, namely, tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GRM3, KLH32, MAGE2, NRG3, OMG, SLC39A12, RTN1, MT3, are publicly available.

In a particular aspect, the citrullinated peptides of the invention bind with high affinity to cit-peptide autoantibodies (the term "peptide" is used generally and can refer to a protein biomarker described herein including NRGN, MBP, etc.). It is understood by one of skill in the art, that "high affinity" is used synonymously with the terms "specifically binds to" and "specific for" and refers to the capability of the citrullinated NRGN peptides (for example) to bind with higher or increased affinity to a cit-NRGN autoantibody as compared with a non-citrullinated NRGN antibody. It is further understood that such binding affinity can be readily established for example in vitro using a peptide binding assay in which a sample peptide is used to displace a standard peptide.

Accordingly, in a specific embodiment, the present invention provides a NRGN polypeptide comprising one or more citrullinated arginine sites. In other embodiments, the present invention provides peptides comprising one or more citrullinated arginine sites of MBP, GFAP, PAD-2, tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GRM3, KLH32, MAGE2, NRG3, OMG, SLC39A12, RTN1, MT3, isoforms thereof, post-translationally modified forms thereof. Reference is made to the Tables and sequence listing provided herein for the citrullinated arginine residues.

Methods for generating peptides are well known in the art. Therefore, additional citrullinated polypeptides are within the scope of the invention. The replacement of one or more arginine residues with a citrulline residue to generate a multitude of citrullinated polypeptides (of any length) and subsequent analyses thereof can be carried out without undue experimentation.

Certain of these polypeptide sequences may contain additional arginines that may be converted to citrulline. Generally, the polypeptides of the present invention may comprise any suitable length for specific recognition by cit-peptide autoantibodies. In one embodiment, the citrullinated polypeptide is a full length protein. In other embodiments, the citrullinated polypeptide may comprise at least about 2 amino acids to about several hundred amino acids in length. More specifically, the citrullinated polypeptides may comprise at least about 8 or 9 amino acids to several hundred amino acids in length. Even more specifically, the citrullinated polypeptides may comprise at least about 10-20 amino acids in length to at least about 100 amino acids in length. Furthermore the citrullinated polypeptides of the present invention may comprise about 9 to about 50 amino acids in length and include any ranges of length therein (i.e., 9-50, 9-45, 9-40, 9-35, 9-30, 9-25, 9-20, 9-15, etc.) as is understood by one of skill in the art. Peptides of over about 50 amino acids in length are also encompassed by the present invention. The length of polypeptide is only restricted by its binding capability to specifically bind cit-polypeptide autoantibodies.

The polypeptides of the present invention may also include multipeptides. In the context of the present invention, a multipeptide is a molecule comprised of at least two antigenic peptide units, i.e. combinations of peptide units that may or may not be linked by a covalent bond. Such multipeptides may be comprised of linear, branched, cyclic peptide units or a combination of these. Multipeptides may be comprised both of peptide units having the same amino acid sequence, and of peptide units having different amino acid sequences. A multipeptide according to the invention comprises at least 7, preferably at least 10 amino acids, i.e. the peptide units may overlap. In specific embodiments, the present invention may comprise cyclic versions of citrullinated polypeptides.

In addition, the citrullinated polypeptides of the present invention may also include dimers and trimers of the peptides as well as additional stabilizing flanking sequences as is understood by those of skill in the art and described for example in U.S. Pat. Nos. 6,184,204 and 5,824,315. A multimer according to the invention can either be a homomer, consisting of a multitude of the same peptide, or a heteromer consisting of different peptides. As stated, the amino acid sequences of the polypeptides according to the invention can be flanked by random amino acid sequences. Preferred are flanking sequences that have a stabilizing effect on the polypeptides, thus increasing their biological availability. In addition, other peptidomimetics are also useful in the polypeptides of the present invention. For a general review, see A. F. Spatola, in CHEMISTRY AND BIOCHEMISTRY OF AMINO ACIDS, PEPTIDES AND PROTEINS, B. Weinstein, eds., Marcel Dekker, New York, p. 267 (1983). The polypeptides of the invention also encompass polypeptides that have been modified by, for example, phosphorylation, glycosylation or lipidation.

Furthermore, the polypeptides of the present invention may also encompass "functionally equivalent variants" or "analogues" of the polypeptides. As such, this would include but not be limited to polypeptides with partial sequence homology, polypeptides having one or more specific conservative and/or non-conservative amino acid changes and polypeptide conjugates which do not alter the biological or structural properties of the polypeptide.

In terms of "functional analogues", it is well understood by those skilled in the art, that inherent in the definition of a biologically functional polypeptide analogue is the concept that there is a limit to the number of changes that may be made within a defined portion of the molecule and still result in a molecule with an acceptable level of equivalent biological activity. A plurality of distinct polypeptides with different substitutions may easily be made and used in accordance with the invention. It is also understood that certain residues are particularly important to the biological or structural properties of a polypeptide, and such residues may not generally be exchanged.

Functional analogues can be generated by conservative or non-conservative amino acid substitutions. Amino acid substitutions are generally based on the relative similarity of the amino acid side-chain substituents, for example, their hydrophobicity, hydrophilicity, charge, size and the like. Thus, within the scope of the invention, conservative amino acid changes means, an amino acid change at a particular position which is of the same type as originally present; i.e. a hydrophobic amino acid exchanged for a hydrophobic amino acid, a basic amino acid for a basic amino acid, etc. Examples of conservative substitutions include the substitution of non-polar (hydrophobic) residues such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another. Such amino acid changes result in functional analogues in that they do not significantly alter the overall charge and/or configuration of the polypeptide. Examples of such conservative changes are well-known to the skilled artisan and are within the scope of the present invention. Conservative substitution also includes the use of a chemically derivatized residue in place of a non-derivatized residue provided that the resulting polypeptide is a biologically functional equivalent to the polypeptides of the invention. Therefore, the citrullinated polypeptides of the present invention encompass a polypeptide having an amino acid sequence that differs from the sequences provided herein by one or more conservative amino acid substitutions. The citrullinated polypeptides of the invention also encompass a polypeptide having an amino acid sequence that differs from the sequences provided herein by a single mutation, where the single mutation represents a single amino acid deletion, insertion or substitution.

The present invention further provides citrullinated peptides. The citrullinated peptides of the present invention may be made by methods known to those of skill in the art most notably and preferably by chemical synthesis using techniques well known in the chemistry of proteins such as solid phase synthesis (Merrifield et al., 65 J. AM. CHEM. ASSOC. 2149 (1964); Merrifield et al., 85 J. AMER. CHEM. SOC. 2149 (1963); and Merrifield et al., 35 INT. J. PEPTIDE PROTEIN RES. 161-214 (1990)) or synthesis in homogenous solution (METHODS OF ORGANIC CHEMISTRY, E. Wansch (Ed.) Vol. 15, pts. I and II, Thieme, Stuttgart (1987)) to generate synthetic peptides. Citrulline is a post-translationally modified arginine that is created through the process of deimination which is catalyzed by the enzyme peptidylarginine deiminase 4 (PAD-4) that removes a positive charge from arginine and makes the resulting citrulline polar in nature.

In one embodiment, citrullinated peptides of the invention can be made from known commercially available sources. In this aspect, the lyophilized protein is reconstituted in an appropriate buffer to which the enzyme peptidylarginine deiminase 4 is added. Alternatively, $Ca^{2+}$ is added to PAD-4 in solution. The solution is allowed to stand at an appropriate temperature for a time sufficient to cause modification of arginine residues to citrulline and thus create a citrullinated protein. The citrullinated protein is then isolated by the removal of the enzyme using a high molecular weight membrane to separate the enzyme or other methods of chromatography. One of skill in the art will understand that the temperature of incubation, buffer condition and time of incubation may vary depending on the protein that is being deiminated (Masson-Bessiere et al., 166 J. IMMUNOL. 4177-4184 (2001)).

The citrullinated proteins may be further isolated and purified by methods selected on the basis of properties revealed by its sequence. Purification can be achieved by protein purification procedures such as chromatography methods (gel-filtration, ion-exchange and immunoaffinity), by high-performance liquid chromatography (HPLC, RP-HPLC, ion-exchange HPLC, size-exclusion HPLC, high-performance chromatofocusing and hydrophobic interaction chromatography) or by precipitation (immunoprecipitation). Polyacrylamide gel electrophoresis can also be used to isolate the citrullinated proteins based on the molecular weight of the protein, charge properties and hydrophobicity. The purified citrullinated proteins can be used in further biochemical analyses to establish secondary and tertiary structure which may aid in the design of pharmaceuticals to interact with the protein, alter the protein charge configuration or charge interaction with other proteins or alter its function.

V. Assays of Autoantibodies to Citrullinated Peptides

The present invention provides compositions and methods for using citrullinated peptides. In several embodiments, the citrullinated peptides described herein can be used to assay for the presence of corresponding autoantibodies. In a specific embodiment, a method for detecting the presence of autoantibodies to citrullinated NRGN in a subject comprises contacting a biological sample taken from a subject with a citrullinated NRGN polypeptide, and detecting the binding of the polypeptide with an autoantibody specific for the polypeptide, wherein the detection of binding is indicative of the presence of citrullinated NRGN autoantibodies in the subject. The present invention contemplates the detection of autoantibodies to tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GRM3, KLH32, MAGE2, NRG3, OMG, SLC39A12, RTN1, MT3, isoforms thereof, post-translationally modified forms thereof, or combinations of any of the foregoing. More specifically, the present invention contemplates the detection/quantification/measurement of autoantibodies against the modified and/or unmodified protein/peptide.

Methods for assaying such autoantibodies are described herein in and known to those of ordinary skill in the art. For example, an immunoassay can be used to detect and analyze autoantibodies in a biological sample. As used herein, the term "immunoassay" is used in reference to any method in which antibodies are used in the detection of an antigen. It is contemplated that a range of immunoassay formats be encompassed by this definition, including but not limited to, direct immunoassays, indirect immunoassays, and "sandwich immunoassays." However, it is not intended that the present invention be limited to any particular format. It is contemplated that other formats, including radioimmunoassays (RIA), immunofluorescent assays (IFA), and other assay formats, including, but not limited to, variations on the ELISA, RIA and/or IFA methods will be useful in the methods of the present invention. The term also includes immunoprecipitation and immunoblotting.

Thus, in one aspect, the methods of the present invention include using a sandwich assay to detect the cit-NRGN autoantibodies. It is understood that in the context of this section, the term NRGN is used as a specific example out of convenience. The assays and peptides described below are applicable to the other proteins/peptides/biomarkers described herein including, but not limited to, tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GRM3, KLH32, MAGE2, NRG3, OMG, SLC39A12, RTN1, MT3, isoforms thereof, post-translationally modified forms thereof, or combinations of any of the foregoing. Sandwich assays generally involve the use of two binding agents, e.g., antibodies, each capable of binding to a different portion, or epitope, of the protein(s) to be detected and/or quantified. In a sandwich assay, the analyte is typically bound by a first binding agent, which is immobilized on a solid support, and thereafter a second binding agent binds to the analyte, thus forming an insoluble complex. See, e.g., U.S. Pat. No. 4,376,110. Alternatively, the sandwich assay may be performed in solution, also referred to as a homogeneous assay. See, e.g., U.S. Pat. No. 7,413,862.

In some embodiments of these methods, a capture probe including a first binding agent is capable of specifically binding to a brain injury-associated antigen, e.g., a NRGN polypeptide, which is bound to one or more autoantibodies. In turn, the detection probe including a second binding agent binds to the autoantibodies. Thus, in this particular example, a four-part complex is formed between: (1) the capture probe, (2) the disease-associated antigen, (3) the autoantibody, and (4) the detection probe. In an alternative embodiment, the positions of the first and second binding agents are reversed, such that the capture probe attached to the solid support is capable of specifically binding to the autoantibodies and the detection probe is capable of specifically binding to the brain injury-associated antigen.

As stated above, the methods can be performed using any immunological technique known to those skilled in the art of immunochemistry. As examples, ELISA, immunofluorescence, radioimmunoassays or similar techniques may be utilized. In general, an appropriate capture probe is immobilized on a solid surface and the sample to be tested (e.g., human serum) is brought into contact with the capture probe. For example, modified glass substrates that covalently or non-covalently bind proteins can be used to bind the disease-associated antigen. The substrate may be treated with suitable blocking agents to minimize non-specific binding. If the autoantibody is present in the sample, a complex between the autoantibody and the capture probe is formed. A detection probe is then added, which specifically recognizes an epitope of a human immunoglobulin (Ig), if present. The anti-human immunoglobulin detection probe may be directed against the Fc region of the human antibody and with as little cross-reactivity as possible against the capture antibody species.

In another embodiment, the methods comprise contacting a sample with a capture probe including an antibody capable of binding to a disease-associated antigen. The sample is also contacted with a detection probe including anti-human Ig antibodies. The presence, absence, and/or amount of the complex may be detected, wherein the presence or absence of the complex is indicative of the presence or absence of the autoantibodies.

The complex can then be detected or quantitatively measured using methods well-known in the art. The detection probe may be labeled with biochemical markers such as, for example, a nanoparticle, horseradish peroxidase (HRP) or alkaline phosphatase (AP), and detection of the complex can be achieved by the addition of a substrate for the enzyme which generates a calorimetric, chemiluminescent or fluorescent product. Alternatively, the presence of the complex may be determined by addition of a marker protein labeled with a detectable label, for example an appropriate enzyme. In this case, the amount of enzymatic activity measured is inversely proportional to the quantity of complex formed and a negative control is needed as a reference to determine the presence of antigen in the sample. Another method for detecting the complex may utilize antibodies or antigens that have been labeled with radioisotopes followed by measure of radioactivity.

The sample may be contacted with the detection probe before, after, or simultaneously with the capture probe. In one embodiment, the sample is first contacted with the detection probe so that autoantibodies present in the sample bind to the detection probe to form a target analyte complex. The mixture is then contacted with the substrate having capture probes bound thereto so that the target analyte complex binds to the capture probe on the substrate. In another embodiment, the sample is first contacted with the substrate so that a target analyte complex present in the sample binds to a capture probe, and the target analyte complex bound to the capture probe is then contacted with the detection probe so that the autoantibodies bind to the detection probe. In another embodiment, the sample, the detection probe and the capture probe on the substrate are contacted simultaneously.

The present invention further provides kits for commercial sale. In certain embodiments, the kit may comprise at least one cit-NRGN polypeptide. The kit may comprise the equipment, solutions and and/or instructions necessary for all steps in the process of creating cit-NRGN polypeptides, detecting cit-NRGN autoantibodies, and the like. Furthermore, the kit can further comprise peptides of MBP, GFAP, PAD-2, tubulin beta-4B chain, tubulin alpha-1B chain, CNPase, PPIA, Septin-7, Elongation factor1-alpha2, TPPP, TPPP3, Ermin Isoform 2, NDRG2 Isoform 2, ASTN1, BAI3, CNDP1, ERMIN, GRM3, KLH32, MAGE2, NRG3, OMG, SLC39A12, RTN1, MT3, isoforms thereof, post-translationally modified forms thereof, for use in detecting autoantibodies thereto.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Reagents and Chemicals.

Bovine myelin basic protein (MBP) and peptidylarginine deiminase type 2 (PAD2) were obtained from Sigma-Aldrich (St. Louis, Mo.). Bovine neurogranin (NRGN) and bovine glial fibrillary acidic protein (GFAP) were identified by mass spectrometry (MS) within the bovine MBP sample. Recombinant human NRGN was expressed in bacteria (Rosetta 2 DE3, pEX—N-His-NRGN plasmid) and purified with Ni-NTA agarose beads. Additional amino acid residues were introduced in the recombinant protein NRGN, including His tag at N-terminus, T79 and R80 at C-terminus (FIG. 8). Native human glial fibrillary acidic protein (GFAP) from human brain was purchased from Calbiochem (EMD Chemical, Inc., Gibbstown, N.J.). Human MBP was identified by mass spectrometry within the human GFAP sample. Sequencing grade modified trypsin and endoproteinase Glu-C were purchased from Promega (Madison, Wis.). Endoproteinase Lys-C was obtained from Roche Diagnostics (Indianapolis, Ind.). RapiGest surfactant was purchased from Waters (Milford, Mass.). Other chemicals were from Sigma-Aldrich (St. Louis, Mo.).

Peptidylargininedeiminase Treatment and Proteolysis.

Bovine MBP, human GFAP, and human recombinant protein NRGN were untreated or treated with PAD2 to convert peptidylarginine to peptidylcitrulline. Protein concentration was determined using a Pierce bicinchoninc acid (BCA) protein assay kit (Pierce, Rockford, Ill.). Each protein (2 µg) was treated with 0.15 µg of PAD2 (specific activity, 0.254 unit/µg; one unit will produce 1 µmole of N-α-benzoylcitrulline ethyl ester from N-benzoyl-L-arginine ethyl ester (BAEE) per hr at 55° C. at pH 7.2) in a total volume of 40 uL of a buffer composed of 20 mM $CaCl_2$, 200 mM Tris-HCl pH 7.5, 10 mM dithiothreitol, at 55° C. for 2 hours. Untreated samples were dissolved in the same buffer. Samples with and without PAD2 treatment were denatured with 0.1% RapiGest surfactant, reduced with 5 mM tris(2-carboxyethyl)phosphine at 50° C. for 30 minutes, and alkylated with 10 mM iodoacetamide at room temperature for 30 min (in the dark). Sequencing grade modified trypsin, Lys-C, or Glu-C was added to protein samples at a ratio of 1:20 (enzyme to substrate). The samples were incubated at 37° C. for 16 hours. Samples were desalted by solid phase extraction with Oasis reverse-phase HLB cartridges (30 mg/30 µm, Waters, Milford, Mass.).

Protein Extraction from Human Brain Tissue Samples.

Human spinal cord tissue was obtained with permission from two patients of the School of Medicine Hospital at Johns Hopkins University. The tissue sample (~60 mg) was homogenized in 0.5 mL lysis buffer (8 M urea, Amberlite IRN 150L, 2 M thiourea, 4% Chaps, 1% DTT) and proteins were extracted with Sample Grinding Kit (GE Healthcare, Piscataway, N.J.) according to the product protocol. The homogenate was centrifuged at 12,000 rpm for 10 min and the supernatant was saved in −80° C. freezer. The supernatant (100 µL) was cleaned with 2-D clean-up kit (GE Healthcare, Piscataway, N.J.) following the instruction. After precipitation and centrifugation, the pellet was dissolved in 6 M urea. The protein concentration of two preparations was determined using Pierce BCA protein assay kit (Pierce, Rockford, Ill.). The protein extract was reduced, alkylated, and digested with trypsin, Lys-C, or Glu-C as described above.

LC-MS/MS and Data Analysis.

Digested protein samples (100 ng) were analyzed by nanoflow HPLC on a LTQ-Orbitrap mass spectrometer (Thermo Fisher Scientific, San Jose, Calif.). An Agilent 1200 series nanoflow LC system (Agilent, Santa Clara, Calif.) was used for chromatographic separation with Solvent A (0.1% formic acid) and Solvent B (90% acetonitrile in 0.1% formic acid). Samples were loaded onto reverse-phase capillary columns, 75 μm inner diameter PicoFrit-Self/P column (New Objective, Woburn, Mass.), in house packed with 10 cm of Magic C18AQ packing material (5 μm diameter particles, 200 Å pore size) from Michrom Biore-sources, Inc. (Auburn, Calif.). Separation started with 2% solvent B for 8 min at a flow rate of 2 μL/min. A 36 min linear gradient from 10% to 45% solvent B was followed by a 10 min linear gradient from 45% to 95% solvent B at a flow rate of 300 nL/min.

The LTQ-Orbitrap with a nanoelectrospray ionization source was controlled by Xcalibur 2.0.7 and LTQ-Orbitrap MS SP2 (Thermo Fisher Scientific, San Jose, Calif.). The LTQ-Orbitrap mass spectrometer was operated in positive mode with the electrospray voltage at +1.7 kV. An MS survey scan (from m/z 250-1800) was acquired in the Orbitrap with a resolution r=60,000 at m/z 400. The top five most intense ions were isolated and fragmented by CID (normalized collision energy: 35%) in the linear ion trap. The MS/MS spectra were acquired in the linear ion trap at unit resolution sequentially. Dynamic exclusion was enabled with exclusion duration of 30 sec.

Peptides and proteins were initially identified using the Sorcerer 2 SEQUEST (version 3.5, Sage-N Research, Milpitas, Calif.) search engine with postsearch analysis using Scaffold 3 (Proteome Software Inc., Portland, Oreg.). MS/MS spectra were searched against the International Protein Index human sequence database (v3.79) or International Protein Index bovine sequence database (v3.68). Search parameters included carbamidomethylation at cysteines, semi-enzymatic digestion with up to three missed cleavages, asparagines or glutamine deamination as variable modifications. Mass tolerance was 50 ppm for precursor ions and 1.00 Da for fragment ions. Manual verification was applied to MS/MS spectra of citrullinated peptides and their unmodified counterpart. First, MS/MS spectra were compared with theoretical fragment ion peaks. Second, m/z values of precursor ions were compared to theoretical values obtained from MS-Product (http://prospector.ucsf.edu). Third, HPLC peaks of citrullinated peptides and their unmodified counterpart were identified from all protein samples.

Results

Example 1: LC-MS/MS Analysis of Bovine MBP Protein

It was reported previously that bovine MBP has two citrullination sites. Because bovine MBP was readily available commercially, bovine MBP was selected as a model protein to establish a LC-MS/MS method for the identification of citrullinated peptides from complex mixtures. Both Lys-C and trypsin were used as endoproteinase to generate peptide fragments from bovine MBP sample.

Figure 1A:
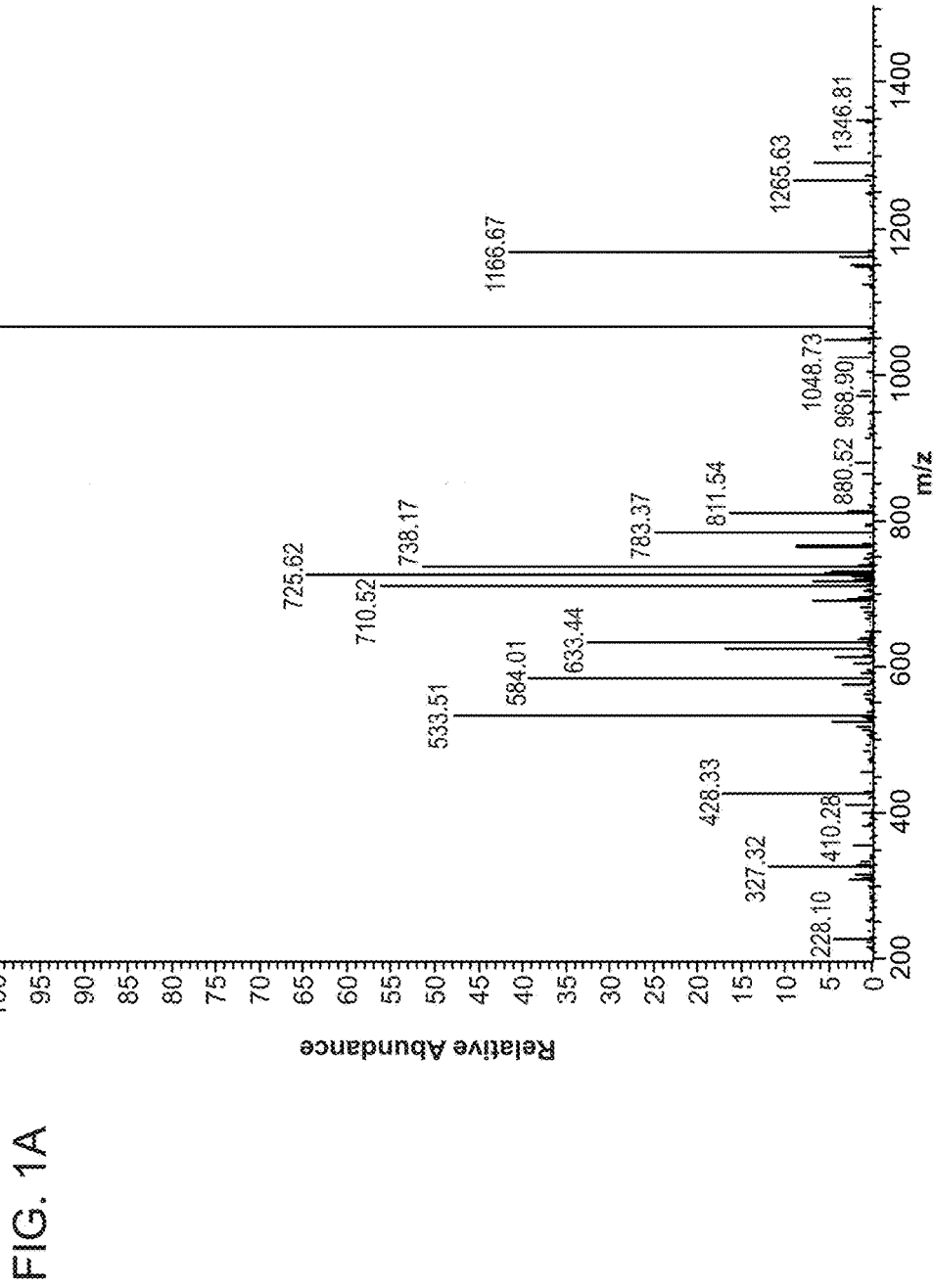
FIGS. 1A-1D present MS/MS spectra and extracted ion chromatograms of citrullinated peptides of endogenous bovine MBP digested with Lys-C.
Figure 1B:
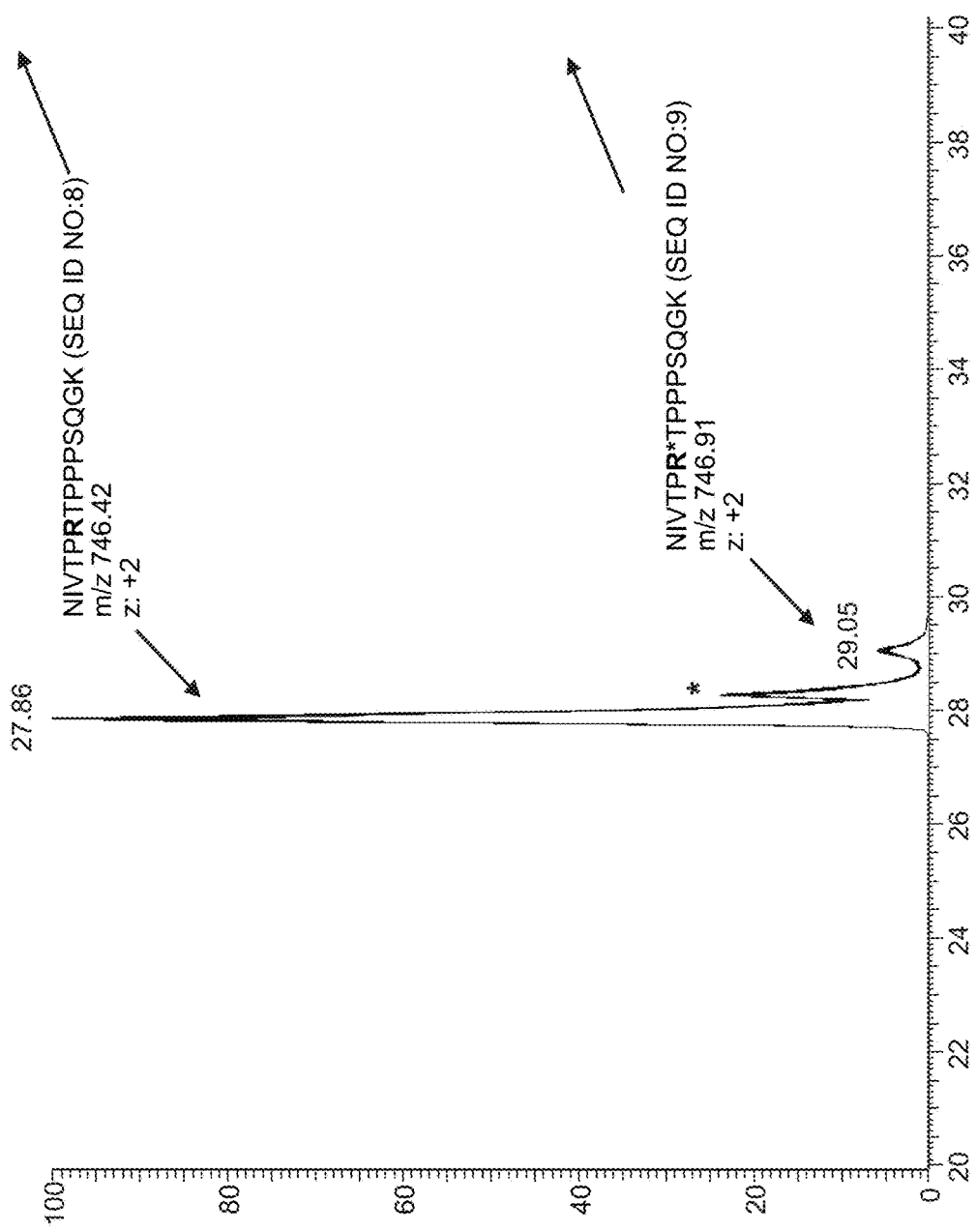
Figure 1C:
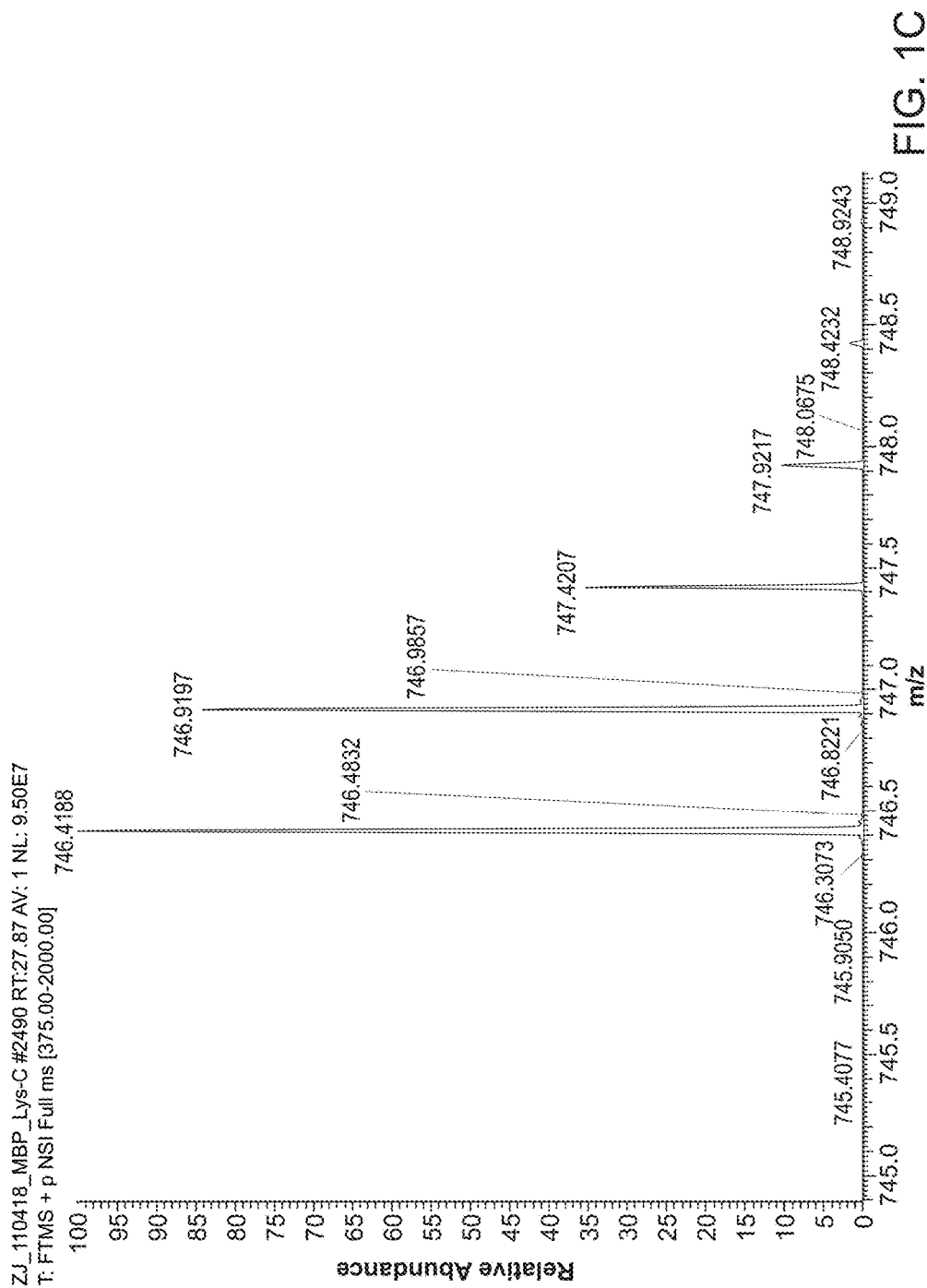
Figure 1D:
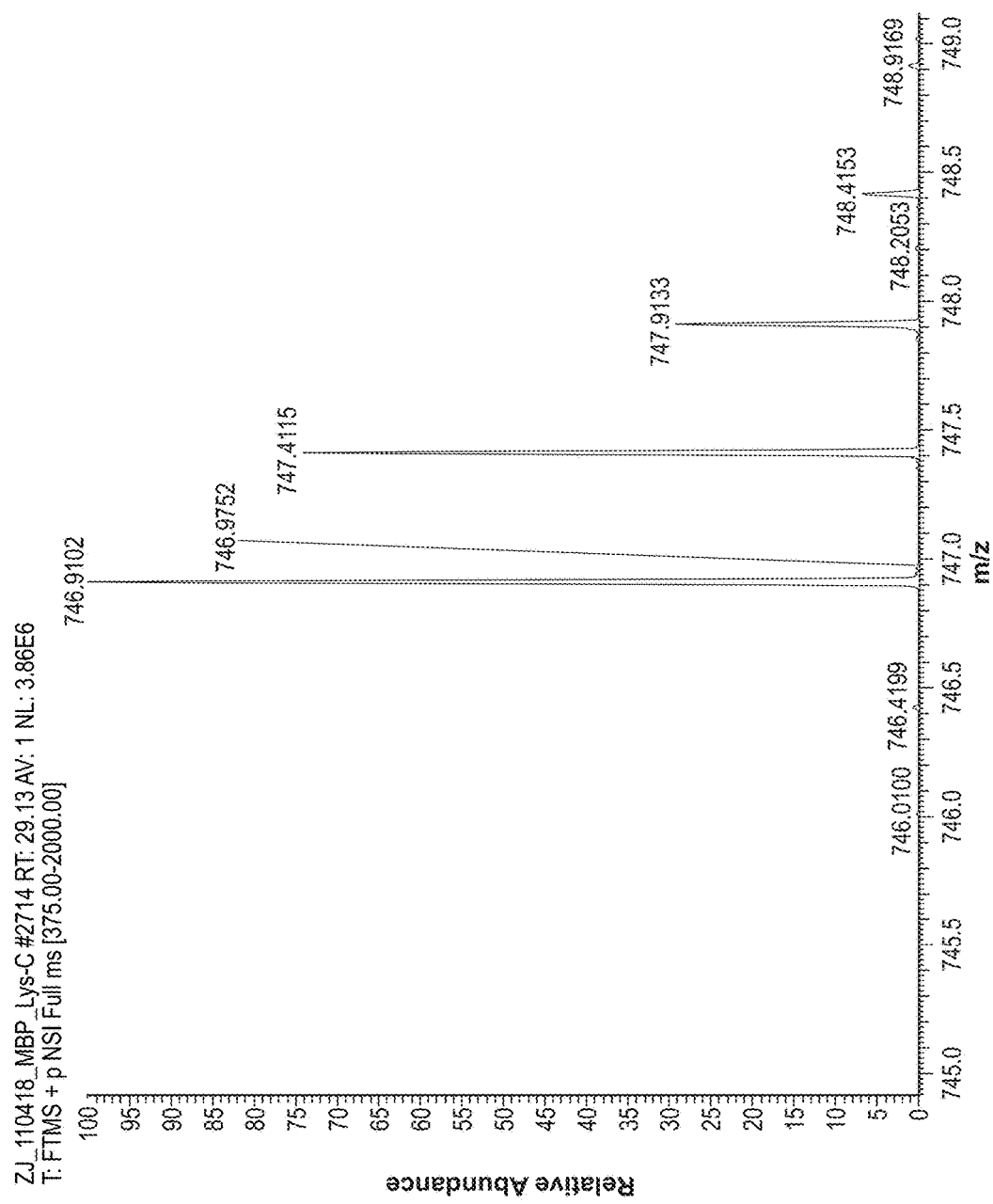
Figure 2A:
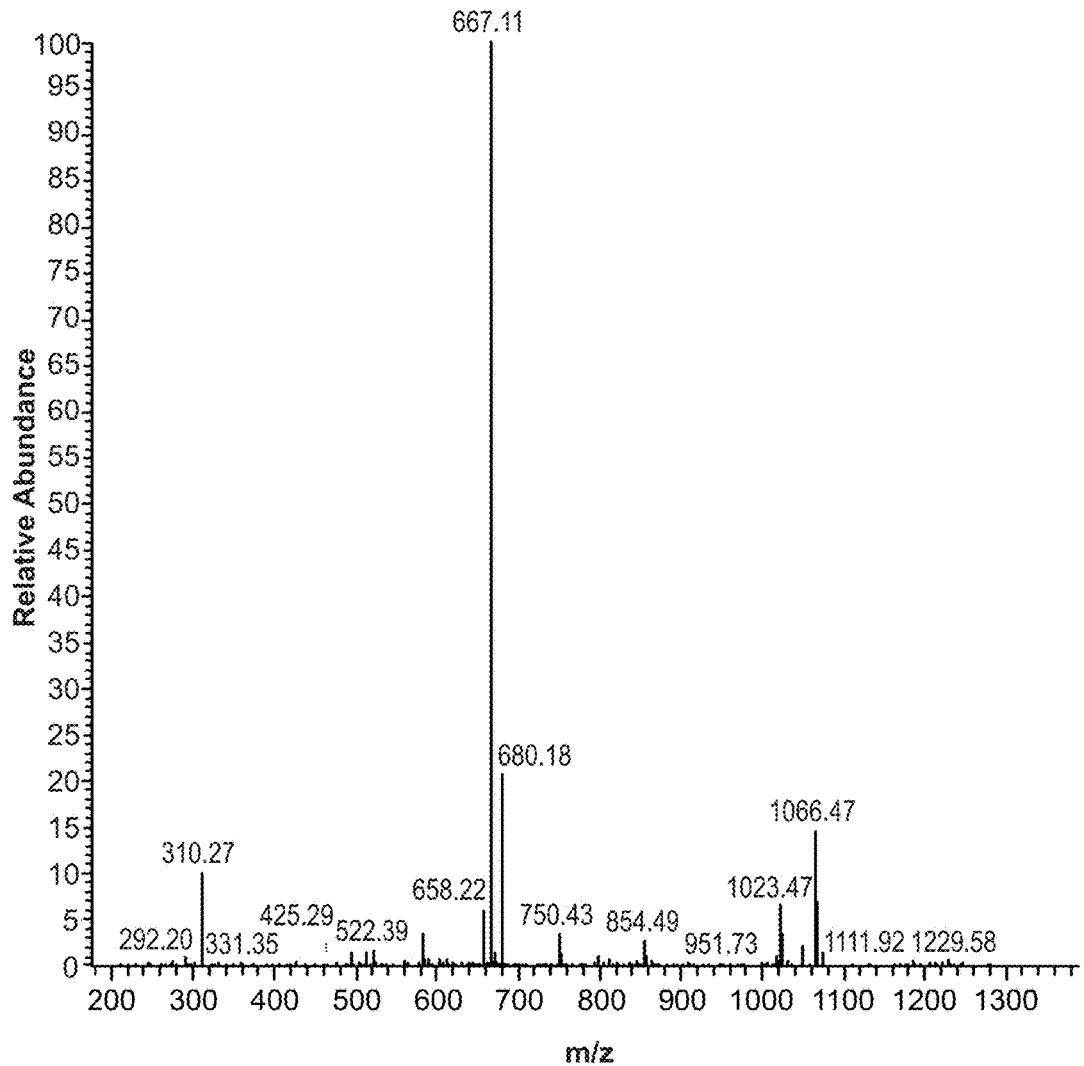
FIGS. 2A and 2B show MS/MS spectra and extracted ion chromatograms of citrullinated peptide of endogenous bovine MBP digested with Lys-C.
Figure 2B:
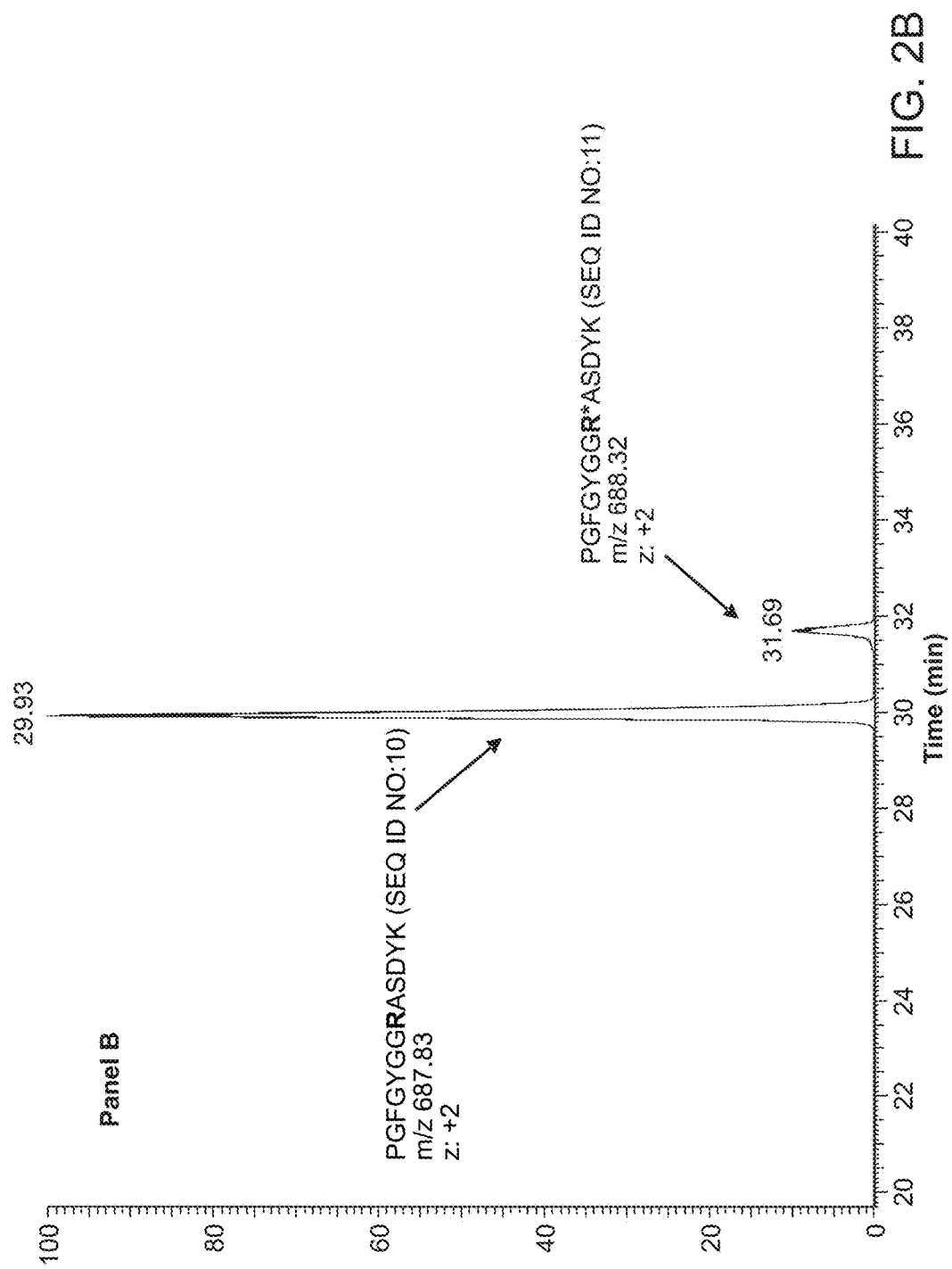
Figure 3A:
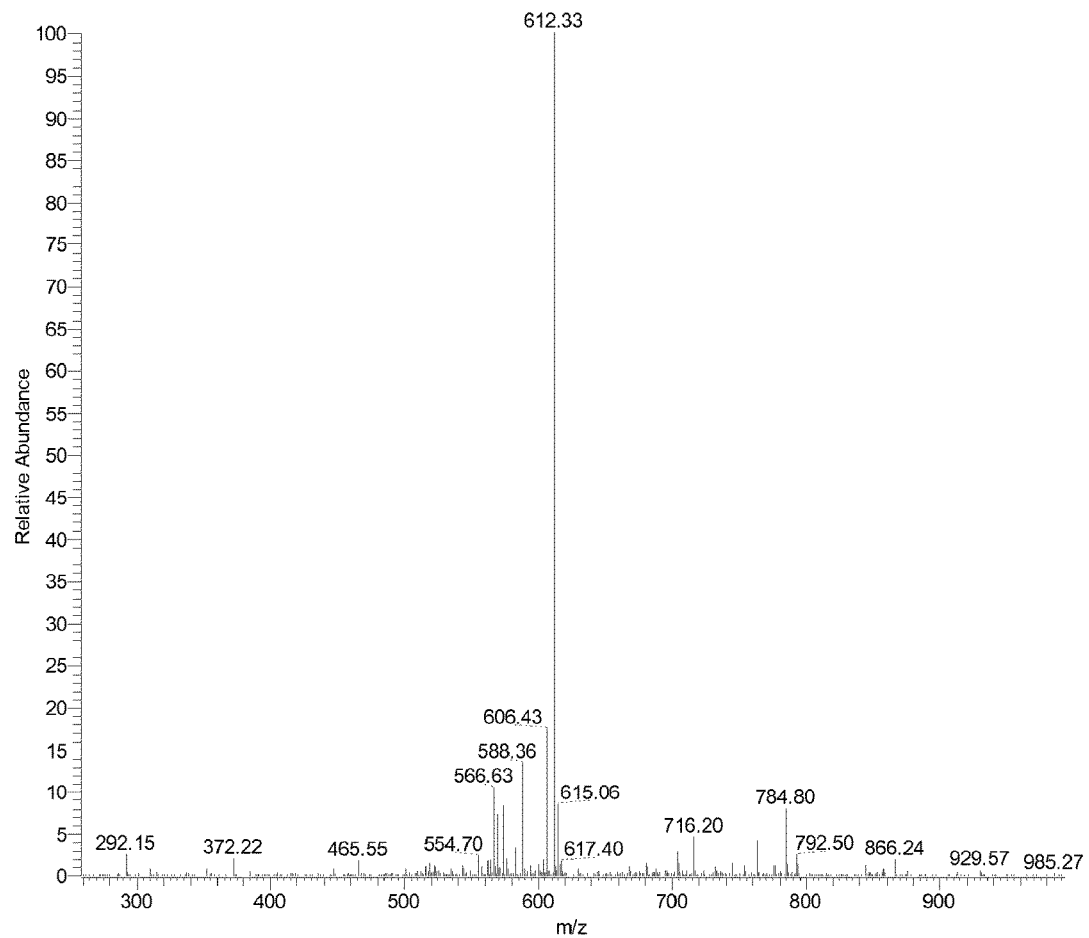
FIGS. 3A and 3B show MS/MS spectra and extracted ion chromatograms of citrullinated peptide of endogenous bovine MBP digested with Lys-C.
Figure 3B:
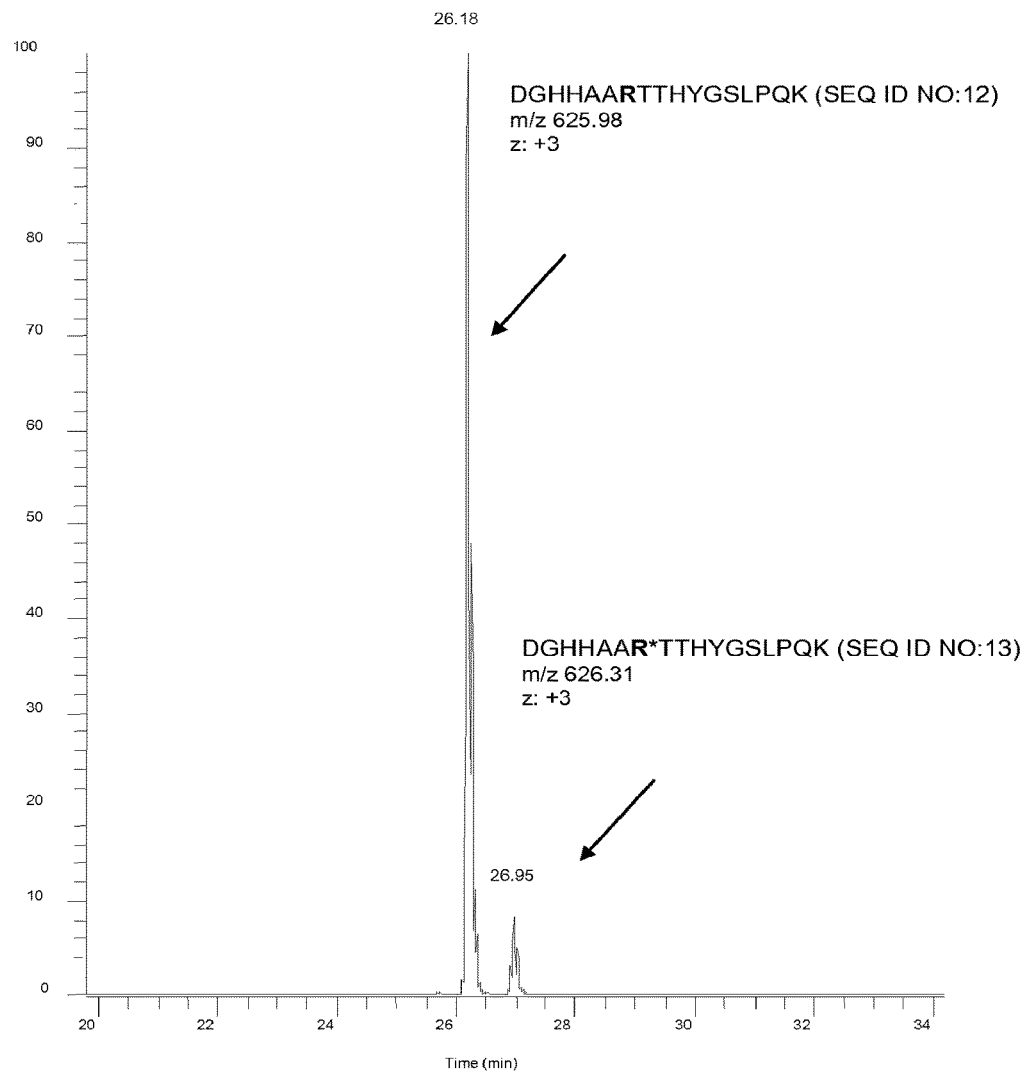

A total of five arginine residues were found citrullinated naturally in bovine MBP (Table 1). The citrullinated peptides and related unmodified peptides were identified by initial database searching. Each LTQ-MS/MS spectrum (FIGS. 1A, 2A, and 3A) was manually verified by comparing it with theoretical fragment ion peaks. Citrullination of a peptide results in mass increment increase of 0.98402 amu. The peptide sequences were also confirmed by high-resolution Orbitrap MS analysis (Table 1 and FIGS. 1C, 1D). Natural citrullination at R41, R47, and R63 residues in MBP protein were first identified. Citrullination at R129 residue (R130 in human MBP) was previously reported in human MBP protein and citrullination of R96 residue was reported previously in bovine MBP. These citrullinated arginine residues are conserved in human. The citrullinated peptide NIVTPR*TPPPSQGK (residue 91-104) (SEQ ID NO:9), PGFGYGGR*ASDYK (residue 122-134) (SEQ ID NO:11), and DGHHAAR*TTHYGSLPQK (residue 57-73) (SEQ ID NO: 13) were eluted later than their unmodified peptides on the reversed-phase HPLC column (FIGS. 1B, 2B and 3B). These results can be explained by the loss of positive charged functional group of arginine after citrullination. As shown in FIG. 2A, neutral loss of isocyanic acid (HN=CO) in the MS/MS spectra of citrullinated peptides is a typical fragmentation pathway under collision induced dissociation (CID). This unique fragment ion was monitored in the identification and verification of citrullinated peptides.

TABLE 1

Citrullinated Peptide and Related Unmodified Peptide of MBP Identified in Bovine MBP Digested with Lys-C or Trypsin; New Sites are Underlined.

| Peptide Sequence | Sequence Number[a] | Enzyme | Theoretical m/z[b] | Experimental m/z | z[c] | R.T. (min) | Citrullinated amino acid residue |
|---|---|---|---|---|---|---|---|
| NIVTPRTPPPSQGK (SEQ ID NO: 8) | 91-104[d] | Lys-C | 746.4181 | 746.4188 | +2 | 27.9 | NA[e] |
| NIVTPR*TPPPSQGK (SEQ ID NO: 9) | 91-104 | Lys-C | 746.9095 | 746.9110 | +2 | 29.1 | R96[f] |

TABLE 1-continued

Citrullinated Peptide and Related Unmodified Peptide of MBP Identified in
Bovine MBP Digested with Lys-C or Trypsin; New Sites are Underlined.

| Peptide Sequence | Sequence Number[a] | Enzyme | Theoretical m/z[b] | Experimental m/z | z[c] | R.T. (min) | Citrullinated amino acid residue |
|---|---|---|---|---|---|---|---|
| PGFGYGGRASDYK (SEQ ID NO: 10) | 122-134 | Lys-C | 687.8261 | 687.8264 | +2 | 29.9 | NA |
| PGFGYGGR*ASDYK (SEQ ID NO: 11) | 122-134 | Lys-C | 688.3181 | 688.3188 | +2 | 31.7 | R129[f] |
| DGHHAARTTHYGSLPQK (SEQ ID NO: 12) | 57-73 | Lys-C | 625.9785 | 625.9796 | +3 | 26.2 | NA |
| DGHHAAR*TTHYGSLPQK (SEQ ID NO: 13) | 57-73 | Lys-C | 626.3065 | 626.3068 | +3 | 27.0 | R63[g] |
| DTGILDSLGR*FFGSDR (SEQ ID NO: 14) | 32-47 | Trypsin | 878.9287 | 878.9311 | +2 | 47.7 | R41[g] |
| DTGILDSLGR*FFGSDR*GAPK (SEQ ID NO: 15) | 32-51 | Trypsin | 1056.0238 | 1056.0277 | +2 | 46.7 | R41, R47[g] |
| NIVTPR (SEQ ID NO: 16) | 91-96 | Trypsin | 350.2110 | 350.2110 | +2 | 26.1 | NA |
| NIVTPR*TPPPSQGK (SEQ ID NO: 9) | 91-104 | Trypsin | 746.9095 | 746.9102 | +2 | 28.4 | R96[f] |
| PGFGYGGR (SEQ ID NO: 17) | 122-129 | Trypsin | 405.6983 | 405.6981 | +2 | 28.6 | NA |
| PGFGYGGR*ASDYK (SEQ ID NO: 11) | 122-134 | Trypsin | 688.3181 | 688.3188 | +2 | 30.8 | R129[f] |

[a]sequence number, the initiating amino acid at position 1 is alanine for bovine MBP
[b]mass-to-charge ratio of the peptide
[c]charge state of selected precursor ions
[d]peptides with or without phosphorylation at T97 were both detected
[e]NA, not applicable, as no citrullinated residues was identified
[f]Peptide sequence is conserved in human.
[g]Citrullinated arginine residue is conserved in human, but peptide sequence is different.

These citrullinated amino acid residues were confirmed in tryptic digests of bovine MBP. The observation of citrullinated peptides NIVTPR*TPPPSQGK (residue 91-104) (SEQ ID NO:9), PGFGYGGR*ASDYK (residue 122-134) (SEQ ID NO:11), and their unmodified counterpart NIVTPR (residue 91-96) (SEQ ID NO:16), PGFGYGGR (residue 122-129) (SEQ ID NO:17) indicated that citrullination inhibited proteolytic digestion by trypsin (Table 1). These results were different from a previous report that citrullination seemed to not affect tryptic cleavage. The peptide NIVTPRTPPPSQGK (SEQ ID NO:8) likely underwent deamination at Q102 (FIG. 1B). This deamination was also reported previously in the chicken MBP protein.

It was reported previously that the R106 residue of bovine MBP can be mono- or di-methylated. The peptide, GRGLSLSRFSWGAEGQK (residue 105-121) (SEQ ID NO:18) without modification, with mono- or di-methylation at R106 were observed. After PAD2 treatment, GR*GLSLSR*FSWGAEGQK (residue 105-121) (SEQ ID NO:19), peptide GRGLSLSR*FSWGAEGQK (SEQ ID NO:20) with mono- and di-methylation at R106 were observed. These results indicated that mono- or dimethylated arginine may not be citrullinated by PAD2 enzyme.

Example 2: Bovine NRGN and GFAP in MBP Sample

A new protein, neurogranin (NRGN), was found citrullinated in bovine MBP sample. A citrullinated peptide of GFAP was also found. This is the first time that citrullinated residue of GFAP was identified. Both citrullinated peptides and their unmodified counterpart of bovine NRGN and GFAP were identified in the bovine MBP sample (Table 2). The sequence of the citrullinated peptides was confirmed by comparing MS/MS spectra with theoretical fragment ions, unique fragmentation pattern of citrullinated peptide (FIGS. 5A, 5B, 6A and 6B), and high resolution mass-to-charge ratio of precursor ions.

TABLE 2

Other Citrullinated Peptides and Proteins Identified in Bovine MBP Sample Digested with Lys-C, Glu-C, or Trypsin; New Sites are Underlined.

| Protein | Peptide Sequence | Sequence Number [a] | Enzyme | Theoretical m/z [b] | Experimental m/z | z [c] | Citrullinated amino acid residue |
|---------|------------------|---------------------|--------|---------------------|------------------|-------|----------------------------------|
| NRGN | GPGPGGPGGAGGARGGAGG GPSGD (SEQ ID NO: 21) | 55-78 | Lys-C | 888.9040 | 888.9058 | +2 | NA [d] |
|  | GPGPGGPGGAGGAR*GGAG GGPSGD (SEQ ID NO: 22) | 55-78 | Lys-C | 889.3960 | 889.3983 | +2 | R68 [e] |
|  | GPGPGGPGGAGGAR (SEQ ID NO: 23) | 55-68 | Trypsin | 532.7652 | 532.7656 | +2 | NA |
|  | KGPGPGGPGGAGGAR*GGA GGGPSGD (SEQ ID NO: 24) | 54-78 | Trypsin | 953.4435 | 953.4429 | +2 | R68 [e] |
| GFAP | GHLKRNIVVKTVE (SEQ ID NO: 25) | 398-410 | Glu-C | 746.9515 | 746.9504 | +2 | NA |
|  | GHLKR*NIVVKTVE (SEQ ID NO: 26) | 398-410 | Glu-C | 747.4435 | 747.4420 | +2 | R402 [f] |

[a] sequence number includes the initiating Met at position 1 for all proteins except for MBP, bovine. Met is cleaved from in the mature protein.
[b] mass-to-charge ratio of the peptide
[c] z is the charge state of selected precursor ions
[d] NA, not applicable, as no citrullinated residues was identified
[e] Citrullinated arginine residue is conserved in human, but peptide sequence is different.
[f] Peptide sequence is conserved in human.

R68 residue of NRGN was identified as a natural citrullination site present in bovine NRGN. The peptide sequences were confirmed in the digests of Lys-C and trypsin. Because the primary sequence of NRGN is highly conserved across species (FIG. 4), this unique post-translational modification may also be present in human NRGN.

Citrullination at R402 residue of GFAP was identified in endogenous GFAP. Citrullinated peptide GHLKR*NIVVKTVE (residues 398-410) (SEQ ID NO: 26) and the unmodified counterpart (SEQ ID NO: 25) were observed in the Glu-C digests of bovine MBP (FIGS. 6A and 6B).

Example 3: Citrullinated Protein Identified from Human GFAP Sample

It was reported previously that GFAP and MBP protein were citrullinated in the human autoimmune disease, multiple sclerosis (MS). In the previous studies, the citrullinated GFAP and MBP were detected using an antibody against chemically modified citrulline. However, the citrullinated residue(s) of GFAP was not identified.

TABLE 3

Citrullinated Peptide and Unmodified Peptide Identified in Human GFAP Samples Digested with Lys-C, Glu-C; New Sites are Underlined.

| Protein | Peptide Sequence | Sequence Number [a] | Enzyme | Theoretical m/z [b] | Experimental m/z | z [c] | R.T. (min) | Citrullinated amino acid residue |
|---------|------------------|---------------------|--------|---------------------|------------------|-------|------------|----------------------------------|
| GFAP, human | FADLTDAAARNAELLR QAK (SEQ ID NO: 27) | 261-279 | Lys-C | 692.0395 | 692.0394 | +3 | 36.6 | NA [d] |
|  | FADLTDAAAR*NAELL RQAK (SEQ ID NO: 28) | 261-279 | Lys-C | 692.3675 | 692.3679 | +3 | 38.0 | R270 |
|  | GHLKRNIVVKTVE (SEQ ID NO: 29) | 402-414 | Glu-C | 746.9515 | 746.9543 | +2 | 29.5 | NA |
|  | GHLKR*NIVVKTVE (SEQ ID NO: 30) | 402-414 | Glu-C | 747.4435 | 747.4464 | +2 | 29.5 | R406 |

TABLE 3-continued

Citrullinated Peptide and Unmodified Peptide Identified in Human GFAP
Samples Digested with Lys-C, Glu-C; New Sites are Underlined.

| Protein | Peptide Sequence | Sequence Number [a] | Enzyme | Theoretical m/z [b] | Experimental m/z | z [c] | R.T. (min) | Citrullinated amino acid residue |
|---|---|---|---|---|---|---|---|---|
| MBP, human | NIVTPRTPPPSQGK (SEQ ID NO: 31) | 92-105 | Lys-C | 746.4181 | 746.4174 | +2 | 26.7 | NA |
| | NIVTPR*TPPPSQGK (SEQ ID NO: 32) | 92-105 | Lys-C | 746.9095 | 746.9084 | +2 | 27.7 | R97 |

[a] sequence number includes the initiating Met at position 1 for GFAP. Met is removed in the mature protein.
[b] mass-to-charge ratio of the peptide
[c] z is the charge state of selected precursor ions
[d] NA, not applicable, as no citrullinated residues was identified In this investigation, two natural citrullination sites, R270 and R406 residues, were found in an endogenous human GFAP sample digested with Lys-C or Glu-C (Table 3). LC peaks of citrullinated peptide GHLKR*NIVVKTVE (402-414) (SEQ ID NO: 30) and the unmodified counterpart are shown in FIG. 7A. MS/MS spectrum of the citrullinated peptide GHLKR*NIVVKTVE (402-414) (SEQ ID NO: 30) was the same as FIG. 6A and was not shown here. Natural citrullination of R406 residue (R402 in bovine) was also found in bovine GFAP as described above. However, relative abundance of the citrullinated peptide GHLKR*NIVVKTVE (402-414) (SEQ ID NO:30) versus unmodified peptide (SEQ ID NO:29) was much higher in the human GFAP sample (FIGS. 6B and 7A). This result indicated that higher percentage of endogenous GFAP protein was citrullinated in human sample (without considering ionization efficiencies of the two peptides).

Human MBP protein was identified in the human GFAP sample digested with Lys-C (Table 3). This was not unexpected because the GFAP sample was extracted from human brain tissue. Proteins that bind to GFAP may also be isolated during protein purification. Both citrullinated peptide NIVTPR*TPPPSQGK (residues 226-239) (SEQ ID NO:33) and the unmodified counterpart (SEQ ID NO:34) were identified. MS/MS spectra of the citrullinated peptide NIVTPR*TPPPSQ GK (residues 226-239) (SEQ ID NO:33) is the same as FIG. 1A and was not shown here. The peptide sequences were also confirmed by high resolution precursor ion MS analysis (less than ±5 ppm). LC peaks of the citrullinated peptide NIVTPR*TPPPSQGK (residues 226-239) (SEQ ID NO:33) and the unmodified peptide were shown in FIG. 7B. Relative ratio of the citrullinated peptide versus unmodified counterpart was higher in human MBP than that in bovine MBP protein (FIG. 7B and FIG. 1B).

Example 4: LC-MS/MS Analysis of NRGN, GFAP, and MBP after PAD2 Treatment

To locate all possible citrullination sites in NRGN, GFAP, and MBP, these three proteins were treated with PAD2 enzyme. Lys-C and Glu-C were used to generate appropriate peptides for mass spectrometry analysis. The recombinant human NRGN has additional amino acids at the N- and C-terminals introduced as a consequence of subcloning (FIG. 8).

The R68, natural citrullination site found in bovine NRGN, was also citrullinated in human recombinant NRGN after PAD2 treatment. Five additional citrullination sites were observed for recombinant protein NRGN (Table 4 and FIGS. 9A and 9B), including the R80 amino acid introduced during subcloning. These results demonstrated that all five arginine residues of human NRGN may be citrullinated. MS/MS spectrum and extracted ion chromatogram of citrullinated peptide IQASFR*GHMAR*K (residues 33-44) (SEQ ID NO: 101) at m/z 702.36 of human recombinant NRGN in Lys-C digests were shown in FIGS. 9A and 9B. This citrullinated peptide was also observed in the Lys-C digests of bovine NRGN after PAD2 treatment. The unmodified peptide IQASFRGHMARK (residues 33-44) (SEQ ID NO: 36) of NRGN was not observed after PAD2 treatment. This result indicated that PAD2 enzyme catalyzed complete conversion of peptidylarginine to peptidylcitrulline.

For human GFAP protein, a total of thirteen citrullinated arginine residues were identified (Table 4). Two arginine residues, R270 and R406, were found citrullinated naturally in human GFAP protein (Table 3). Eleven additional citrullinated residues were found in PAD2 treated human GFAP in either Lys-C or Glu-C digestions (Table 4 and FIG. 10). The peptide sequences were confirmed by high resolution MS analysis of precursor ions and their CID spectra. Considering the fact that all arginine residues of NRGN can be citrullinated, it's possible that there are additional citrullination sites in the remaining 34 arginine residues of human GFAP.

TABLE 4

Citrullination Sites Identified from GFAP, MBP and NRGN after PAD2 Treatment Followed by Lys-C or Glu-C Digestion; New Sites are Underlined.

| Protein | Citrullinated peptide | Sequence number [a] | Theoretical m/z [b] | Experimental m/z | Enzyme | Citrullinated amino acid residue |
|---|---|---|---|---|---|---|
| NRGN human | IQASFR*GHMAR*K (SEQ ID NO: 35) | 33-44 | 702.3642 | 702.3629 | Lys-C | R38, R43 |
| | GPGPGGPGGAGVAR*GGAGGG PSGDTR* (SEQ ID NO: 37) | 55-80 | 1039.4859 | 1039.4839 | Lys-C | R68, R80 [c] |
| NRGN bovine | IQASFR*GHMAR*K (SEQ ID NO: 38) | 33-44 | 702.3642 | 702.3647 | Lys-C | R38, R43 |
| | GPGPGGPGGAGGAR*GGAGGG PSGD (SEQ ID NO: 39) | 55-78 | 889.3960 | 889.3967 | Lys-C | R68 |
| GFAP human | VR*FLEQQNK (SEQ ID NO: 40) | 87-95 | 581.8144 | 581.8152 | Lys-C | R88 |
| | ALAAELNQLR*AK (SEQ ID NO: 42) | 96-107 | 649.8750 | 649.8754 | Lys-C | R105 |
| | LR*LR*LDQLTANSAR*LE (SEQ ID NO: 44) | 123-138 | 936.5129 | 936.5170 | Glu-C | R124 R126, R136 |
| | AENNLAAYR*QEADE (SEQ ID NO: 46) | 165-178 | 797.8526 | 797.8555 | Glu-C | R173 |
| | LQEQLAR*QQV HVE (SEQ ID NO: 48) | 211-223 | 789.9154 | 789.9181 | Glu-C | R217 |
| | WYR*SKFADLTDAAAR*NAE (SEQ ID NO: 50) | 256-273 | 1043.9996 | 1043.9951 | Glu-C | R258, R270 |
| | FADLTDAAAR*NAELLRQAK (SEQ ID NO: 28) | 261-279 | 692.3675 | 692.3679 | Lys-C | R270 |
| | ANDYR*R*QLQSLTCDLE (SEQ ID NO: 52) | 282-297 | 992.4575 | 992.4612 | Glu-C | R286, R287 |
| | LALDIEIATYR*K (SEQ ID NO: 54) | 357-368 | 703.8981 | 703.8985 | Lys-C | R367 |
| | GHLKR*NIVVKTVE (SEQ ID NO: 56) | 402-414 | 747.4435 | 747.4455 | Glu-C | R406 |
| MBP human | NIVTPR*TPPPSQGK (SEQ ID NO: 32) | 92-105 | 746.9095 | 746.9089 | Lys-C | R97 |
| MBP bovine | YLASASTMDHAR*HGFLPR*HR (SEQ ID NO: 58) | 12-31 | 775.7150 (z: +3) | 775.7166 (z: +3) | trypsin | R23, R29 |
| | YLASASTMDHAR*HGFLPR*HR * (SEQ ID NO: 60) | 12-31 | 776.0430 (z: +3) | 776.0431 (z: +3) | trypsin | R23, R29, R31 |
| | DTGILDSLGR*FFGSDR*GAPK (SEQ ID NO: 61) | 32-51 | 1056.0238 | 1056.0266 | trypsin | R41, R47 |
| | R*GSGKDGHHAAR*TTHYGSLP QK (SEQ ID NO: 63) | 52-73 | 591.5454 (z: +4) | 591.5466 (z: +4) | Lys-C | R52, R63 |
| | DGHHAAR*TTHYGSLPQK (SEQ ID NO: 13) | 57-73 | 938.9561 | 938.9566 | Lys-C | R63 |
| | AQGHR*PQDENPVVHFFK (SEQ ID NO: 65) | 74-90 | 1003.9952 | 1003.9971 | Lys-C | R78 |
| | NIVTPR*TPPPSQGK [d] (SEQ ID NO: 9) | 91-104 | 746.9095 | 746.9109 | Lys-C | R96 |
| | GR*GLSLSR*FSWGAEGQK [e] (SEQ ID NO: 66) | 105-121 | 919.4632 | 919.4651 | Lys-C | R106, R112 |

TABLE 4-continued

Citrullination Sites Identified from GFAP, MBP and NRGN after PAD2
Treatment Followed by Lys-C or Glu-C Digestion; New Sites are Underlined.

| Protein | Citrullinated peptide | Sequence number [a] | Theoretical m/z [b] | Experimental m/z | Enzyme | Citrullinated amino acid residue |
|---|---|---|---|---|---|---|
| | PGFGYGGR*ASDYK (SEQ ID NO: 11) | 122-134 | 688.3181 | 688.3184 | Lys-C | R129 |
| | LGGR*DSR*SGSPMAR*R* (SEQ ID NO: 68) | 155-169 | 803.8837 | 803.8842 | Lys-C | R158, R161 R168, R169 |

[a] sequence number includes the initiating Met at position 1 for all proteins except for MBP, bovine
[b] mass-to-charge ratio of doubly charged ions; charge state of precursor ions is +2 usually
[c] T79 and R80 are introduced into recombinant protein NRGN during subcloning
[d] peptides with or without phosphorylation at T97 were both detected
[e] mono- and di-methylation of R106 were observed on this peptide It was reported previously that 11 arginine residues of human MBP may be citrullinated. Six arginine residues were endogenous citrullination sites (FIG. 11) and five sites were citrullinated after PAD4 treatment. Bovine MBP was reported to have at least two citrullination sites (FIG. 11).

It was found herein that residue R97 was naturally citrullinated in human MBP (isoform 5, 170 residues) as described above. In bovine MBP protein, three new natural citrullination sites, R41, R47, and R63, were identified which were not reported previously. Two natural citrullination sites at the residues R96 and R129 (R130 in human MBP) were confirmed. In the bovine MBP sample treated with PAD2 enzyme, five new sites were identified, and eleven citrullination sites were confirmed (Table 4 and FIG. 11). The C-terminal peptide LGGR*DSR*SGSPMAR*R* (SEQ ID NO: 83) contains four citrullination sites. The sequences of all peptides were confirmed by high resolution MS analysis of precursor ions and their CID spectra. These results showed that all arginine residues of MBP may be citrullinated by PAD enzyme. As shown above, eight new citrullination sites have been identified in bovine MBP: R29, R41, R47, R63, R106, R112, R161, and R168. The corresponding residues in human MBP are R31, R43, R49, R65, R107, R113, R162, and R169.

Example 5: Citrullinated Protein in Human Tissue Samples

MBP, GFAP, and NRGN were identified in the human spinal brain tissue sample in both trypsin and lys-C digests. Protein sequence coverage was 64%, 54%, and 32% respectively. For MBP, eleven endogenous citrullination sites were confirmed in human tissue sample (FIG. 11). The citrullination sites include five novel arginine residues (R43, R49, R65, R162, and R169) that were identified in this invention. This result proves that citrullinated forms of neurological proteins are present in human samples. The modified form of the peptides and proteins can be detected in complex mixtures using our current method.

Example 6: Multiple Reactions Monitor (MRM) Assays for NRGN, GFAP, and MBP

Based on these discoveries, the present inventors have developed MRM assays for the quantification of endogenous human proteins, NRGN, GFAP, MBP, and PAD2 (Tables 5-9, 11-12, and 14-17). The MRM assays were only a fraction of possible example bioanalytical assays based on citrullinated and unmodified peptides described in Table 1-4. These are not a full list of all possible MRM assays. Alternative MRM assays can be developed based on peptides ions of different charge states, peptides with other modifications (for example, oxidation, methylation, and phosphorylation), peptides with combination of citrullinated residues and/or modifications, and peptides generated using other endoproteinase or chemical reagents. Additional citrullination sites may be present for the human GFAP protein. Similar MRM assays can be developed for these additional modified peptides of human GFAP protein. MRM assays could be developed for citrullinated peptides or proteins that were chemically modified.

Other bioanalytical assays can also be developed targeting at either citrullinated peptides and/or their unmodified counterparts. For example, antibodies could be produced to the modified proteins or peptides and be used as assay reagents. Additional assays include but are not limited to, ELISA assays, HPLC with various detectors, capillary electrophoresis (CE) coupled with a mass spectrometer or any other detectors. Similar bioanalytical assays could be developed for citrullinated peptides or proteins that were chemically modified. For high sensitive assays, enrichment method could be developed to improve recovery of modified proteins or peptides. The enrichment methods could be based on chemical reactions that are specific to ureido group of citrulline. Other enrichment methods could antibody based, for example, antibodies against conjugated citrulline, modified peptides, or modified proteins.

One or more of these modified proteins could be used in MRM assays or other bioanalytical assays. Any or combination of modified residues, peptides of one or more of these modified proteins could be used in a bioanalytical assays.

TABLE 5

Developed MRM Assay for Endogenous Human NRGN

| Protein | Peptide | Enzyme | Q1, m/z | Charge | Q3, m/z |
|---|---|---|---|---|---|
| | GPGPGGPGGAGVAR (SEQ ID NO: 70) | Trypsin | 553.79 | +2 | 476.75 |
| | | | 553.79 | +2 | 448.24 |
| | | | 553.79 | +2 | 952.50 |
| | | | 553.79 | +2 | 684.38 |
| | | | 553.79 | +2 | 741.40 |
| | GPGPGGPGGAGVAR*GGAGGGPSGD (SEQ ID NO: 71) | Trypsin | 910.42 | +2 | 888.92 |
| | | | 910.42 | +2 | 731.29 |
| | | | 910.42 | +2 | 1089.54 |
| | | | 910.42 | +2 | 674.27 |
| | | | 910.42 | +2 | 546.21 |
| | KGPGPGGPGGAGVAR*GGAGGGPSGD (SEQ ID NO: 72) | Trypsin | 974.47 | +2 | 952.97 |
| | | | 974.47 | +2 | 731.29 |
| | | | 974.47 | +2 | 833.43 |
| | | | 974.47 | +2 | 1060.55 |
| | | | 974.47 | +2 | 546.21 |
| NRGN, human | GPGPGGPGGAGVARGGAGGGPSGD (SEQ ID NO: 73) | Lys-C | 909.93 | +2 | 804.87 |
| | | | 909.93 | +2 | 833.38 |
| | | | 909.93 | +2 | 1115.51 |
| | | | 909.93 | +2 | 546.24 |
| | | | 909.93 | +2 | 1058.49 |
| | GPGPGGPGGAGVAR*GGAGGGPSGD (SEQ ID NO: 71) | Lys-C | 910.42 | +2 | 888.92 |
| | | | 910.42 | +2 | 731.29 |
| | | | 910.42 | +2 | 1089.54 |
| | | | 910.42 | +2 | 674.27 |
| | | | 910.42 | | 546.21 |
| | IQASFRGHMARK (SEQ ID NO: 36) | Lys-C | 467.92 | +3 | 580.81 |
| | | | 467.92 | +3 | 644.84 |
| | | | 467.92 | +3 | 545.29 |
| | | | 467.92 | +3 | 456.47 |
| | | | 467.92 | +3 | 516.74 |

TABLE 5-continued

Developed MRM Assay for Endogenous Human NRGN

| Protein | Peptide | Enzyme | Q1, m/z | Charge | Q3, m/z |
|---|---|---|---|---|---|
| | IQASFR*GHMAR*K (SEQ ID NO: 35) | Lys-C | 468.58 | +3 | 454.48 |
| | | | 468.58 | +3 | 581.79 |
| | | | 468.58 | +3 | 645.82 |
| | | | 468.58 | +3 | 607.81 |
| | | | 468.58 | +3 | 546.27 |

TABLE 6

Developed MRM Assay for Endogenous Human GFAP

| Protein | Peptide | Enzyme | Q1, m/z | Charge | Q3, m/z |
|---|---|---|---|---|---|
| | VRFLEQQNK (SEQ ID NO: 41) | Lys-C | 581.32 | +2 | 517.27 |
| | | | 581.32 | +2 | 645.37 |
| | | | 581.32 | +2 | 773.43 |
| | | | 581.32 | +2 | 901.49 |
| | | | 581.32 | +2 | 1015.53 |
| | VR*FLEQQNK (SEQ ID NO: 40) | Lys-C | 581.81 | +2 | 560.31 |
| | | | 581.81 | +2 | 404.23 |
| | | | 581.81 | +2 | 906.47 |
| | | | 581.81 | +2 | 759.40 |
| | | | 581.81 | +2 | 646.32 |
| | ALAAELNQLRAK (SEQ ID NO: 43) | Lys-C | 649.38 | +2 | 374.25 |
| | | | 649.38 | +2 | 487.33 |
| | | | 649.38 | +2 | 924.51 |
| | | | 649.38 | +2 | 1080.62 |
| | | | 649.38 | +2 | 1151.65 |
| | ALAAELNQLR*AK (SEQ ID NO: 42) | Lys-C | 649.88 | +2 | 628.38 |
| GFAP | | | 649.88 | +2 | 375.24 |
| human | | | 649.88 | +2 | 488.32 |
| | | | 649.88 | +2 | 730.42 |
| | | | 649.88 | +2 | 924.51 |
| | LALDIEIATYRK (SEQ ID NO: 55) | Lys-C | 703.41 | +2 | 466.28 |
| | | | 703.41 | +2 | 567.33 |
| | | | 703.41 | +2 | 638.36 |
| | | | 703.41 | +2 | 751.45 |
| | | | 703.41 | +2 | 880.49 |
| | LALDIEIATYR*K (SEQ ID NO: 54) | Lys-C | 703.90 | +2 | 682.40 |
| | | | 703.90 | +2 | 839.49 |
| | | | 703.90 | +2 | 881.47 |
| | | | 703.90 | +2 | 752.43 |
| | | | 703.90 | +2 | 568.31 |
| | GHLKRNIVVKTVE (SEQ ID NO: 57) | Glu-C | 498.31 | +3 | 486.81 |
| | | | 498.31 | +3 | 573.37 |
| | | | 498.31 | +3 | 673.43 |
| | | | 498.31 | +3 | 593.37 |
| | | | 498.31 | +3 | 649.91 |
| | GHLKR*NIVVKTVE (SEQ ID NO: 56) | Glu-C | 498.63 | +3 | 484.30 |
| | | | 498.63 | +3 | 487.30 |
| | | | 498.63 | +3 | 410.74 |
| | | | 498.63 | +3 | 575.34 |
| | | | 498.63 | +3 | 674.41 |

TABLE 7

Developed MRM Assay for Endogenous Human MBP

| Protein | Peptide | Enzyme | Q1, m/z | Charge | Q3, m/z |
|---|---|---|---|---|---|
| | NIVTPRTPPPSQGK (SEQ ID NO: 31) | Lys-C | 746.42 | +2 | 583.32 |
| | | | 746.42 | +2 | 632.86 |
| | | | 746.42 | +2 | 710.38 |
| | | | 746.42 | +2 | 1064.58 |
| | | | 746.42 | +2 | 1165.63 |
| | NIVTPR*TPPPSQGK (SEQ ID NO: 32) | Lys-C | 746.91 | +2 | 725.41 |
| | | | 746.91 | +2 | 710.38 |
| | | | 746.91 | +2 | 1065.57 |
| | | | 746.91 | +2 | 1166.62 |
| | | | 746.91 | +2 | 533.29 |
| | SHGRTQDENPVVHFFK (SEQ ID NO: 74) | Lys-C | 949.47 | +2 | 782.35 |
| | | | 949.47 | +2 | 802.88 |
| | | | 949.47 | +2 | 911.40 |
| | | | 949.47 | +2 | 987.54 |
| | | | 949.47 | +2 | 1116.58 |
| | SHGR*TQDENPVVHFFK (SEQ ID NO: 75) | Lys-C | 949.96 | +2 | 928.46 |
| | | | 949.96 | +2 | 987.54 |
| | | | 949.96 | +2 | 873.50 |
| MBP | | | 949.96 | +2 | 677.38 |
| human | | | 949.96 | +2 | 578.31 |
| | DSHHPARTAHYGSLPQK (SEQ ID NO: 76) | Lys-C | 951.47 | +2 | 372.22 |
| | | | 951.47 | +2 | 792.43 |
| | | | 951.47 | +2 | 893.96 |
| | | | 951.47 | +2 | 929.48 |
| | | | 951.47 | +2 | 1110.52 |
| | DSHHPAR*TAHYGSLPQK (SEQ ID NO: 77) | Lys-C | 951.96 | +2 | 930.46 |
| | | | 951.96 | +2 | 759.36 |
| | | | 951.96 | +2 | 872.95 |
| | | | 951.96 | +2 | 894.45 |
| | | | 951.96 | +2 | 1101.57 |
| | LGGRDSRSGSPMARR (SEQ ID NO: 69) | Lys-C | 534.95 | +3 | 515.28 |
| | | | 534.95 | +3 | 523.34 |
| | | | 534.95 | +3 | 552.79 |
| | | | 534.95 | +3 | 714.86 |
| | | | 534.95 | +3 | 499.23 |
| | LGGR*DSR*SGSPMAR*R* (SEQ ID NO: 68) | Lys-C | 803.88 | +2 | 782.39 |
| | | | 803.88 | +2 | 760.89 |
| | | | 803.88 | +2 | 632.32 |

TABLE 7-continued

Developed MRM Assay for Endogenous Human MBP

| Protein | Peptide | Enzyme | Q1, m/z | Charge | Q3, m/z |
|---|---|---|---|---|---|
| | | | 803.88 | +2 | 975.32 |
| | | | 803.88 | +2 | 863.40 |
| | GRGLSLSRFSWGAEGQRPGFGYGGRASDYK[a] (SEQ ID NO: 78) | Lys-C | 1073.87 | +3 | 512.23 |
| | | | 1073.87 | +3 | 796.39 |
| | | | 1073.87 | +3 | 827.48 |
| | | | 1073.87 | +3 | 974.55 |
| | | | 1073.87 | +3 | 1061.59 |
| | GRGLSLSRFSWGAEGQRPGFGYGGR*ASDYK (SEQ ID NO: 79) | Lys-C | 1074.19 | +3 | 1059.86 |
| MBP | | | 1074.19 | +3 | 797.38 |
| human | | | 1074.19 | +3 | 854.4 |
| | | | 1074.19 | +3 | 1017.46 |
| | | | 1074.19 | +3 | 827.48 |
| | GR*GLSLSR*FSWGAEGQRPGFGYGGR*ASDYK (SEQ ID NO: 80) | Lys-C | 1074.85 | +3 | 1060.52 |
| | | | 1074.85 | +3 | 797.38 |
| | | | 1074.85 | +3 | 854.40 |
| | | | 1074.85 | +3 | 585.34 |
| | | | 1074.85 | +3 | 829.45 |
| | GRGLSLSRFSWGAEGQRPGFGYGGRASDYK[a] (SEQ ID NO: 78) | Lys-C | 1073.87 | +3 | 512.23 |

[a]When Lys-C is used, this peptide is longer for human MBP protein because of sequence difference.

TABLE 8

Developed MRM Assay for Human PAD2

| Protein | Peptide | Enzyme | Q1, m/z | Charge | Q3, m/z |
|---|---|---|---|---|---|
| | GFPVVLDSPR (SEQ ID NO: 81) | Trypsin | 543.80 | +2 | 441.76 |
| | | | 543.80 | +2 | 882.50 |
| | | | 543.80 | +2 | 587.31 |
| | | | 543.80 | +2 | 686.38 |
| PAD2 human | | | 543.80 | +2 | 474.23 |
| | WIQDEIEFGYIEAPHK (SEQ ID NO: 82) | Trypsin | 987.98 | +2 | 914.47 |
| | | | 987.98 | +2 | 694.39 |
| | | | 987.98 | +2 | 1061.54 |
| | | | 987.98 | +2 | 1190.58 |
| | | | 987.98 | +2 | 452.26 |

Example 6: In Vivo Analysis of Human GFAP Using CID Triggered HCD

To assess the potential for the citrullination of GFAP, the purified human protein was treated with the PAD2 enzyme in presence of activating calcium. Trypsin, Lys-C or Glu-C were used to generate appropriate peptides of the untreated and treated sample prior to mass spectrometry analysis. In the untreated sample, there were 5 natural citrullination sites, residues R30, R36, R270, R406, and R416, identified for human GFAP protein (Table 9; MS/MS spectra of the citrullinated peptides (data not shown)). Each MS/MS spectrum was manually verified by comparing it with theoretical fragment ions. The peptide sequences were also confirmed by high-resolution Orbitrap MS analysis (Table 12). Neutral loss of isocyanic acid (HNCO) in the MS/MS spectra of citrullinated peptides is a typical fragmentation pathway upon collision induced dissociation. This unique fragment ion was monitored for identification and verification of citrullinated peptides and was observed in majority of samples.

With HCD fragmentation for the same untreated sample the peptide amide backbone cleavage dominates MS/MS spectra of citrullinated peptides as illustrated from a representative typical HCD spectrum of a citrullinated GFAP peptide shown in FIG. 12A and FIG. 12B. The relative abundance of the neutral loss fragment ion was reduced significantly. The formation of sequence-informative b and y ions with HCD greatly facilitates the identification of citrullinated peptides and proteins from complex protein digests. For the identification of citrullinated peptides, HCD spectra are complementary to CID spectra.

After PAD2 treatment of GFAP, a total of seventeen citrullinated arginine residues were identified (Table 9). Note this includes site that were only detected with Lys-C or Glu-C digestion and not trypsin. These included the five in vivo citrullination sites of GFAP observed in the untreated sample as well as an additional twelve citrullinated residues. The peptide sequences were confirmed by CID spectra (FIGS. 13A-13C) and the high accurate m/z values of the precursor ions.

Example 7: LC-MS/MS Analysis of Bovine MBP Protein

A total of five arginine residues of bovine MBP were found citrullinated in the untreated sample whether digested with trypsin (Table 9) or digested with Lys-C (Table 13). The observation of citrullinated peptides NIVTPR*TPPPSQGK (residue 91-104) (SEQ ID NO:9), PGFGYGGR*ASDYK (residue 122-134) (SEQ ID NO:11), and their unmodified counterpart NIVTPR (residue 91-96) (SEQ ID NO: 16), PGFGYGGR (residue 122-129) (SEQ ID NO:17) indicated that citrullination may inhibit proteolytic digestion by trypsin at the C-terminal of citrulline residue. However, one citrullinated peptide of MBP does contain citrulline at the C-terminal (Table 9 and Supplement Table 13). The peptide NIVTPRTPPPSQGK (SEQ ID NO:8) can also undergo deamination at residue Q102. This deamination was reported previously in chicken MBP protein. A neutral loss peak can be used as a diagnostic fragment ion to differentiate this peptide with a N or Q deamination from the peptide with citrullination at residue R96. However, MS/MS spectrum of peptides with N or Q deamination may not be collected due to low ion intensities. In this case, high resolution HCD spectrum was helpful in identifying the peptides with citrullination at arginine residues.

In the bovine MBP sample treated in vitro with the PAD2 enzyme, five novel (not detected previously) citrullination sites were identified, and all eleven citrullination sites that had previously reported were confirmed (Table 9). The CID spectra of all peptides were shown in Table 12 and FIG. 14. The C-terminal peptide LGGR*DSR*SGSPMAR*R* (SEQ ID NO: 83) contains four potential citrullination sites and truncated C-terminal peptides were also observed (Table 9).

Example 8: Citrullinated Peptide of NRGN

Bovine neurogranin was identified within in the commercial bovine MBP sample, as a contaminant which co-purified with MBP. This bovine NRGN protein was found both as the R68 unmodified and citrullinated forms (Table 14). The sequence of the citrullinated peptides containing R68 were confirmed by MS/MS spectra upon CID (data not shown) and accurate m/z value of precursor ions. To locate all possible citrullination sites in human NRGN, which is highly conserved with bovine, recombinant human NRGN was treated with PAD2 enzyme and the untreated and treated samples were digested with either trypsin, Lys-C, or Glu-C. Not unexpected, residue R68 of human NRGN was also citrullinated in human NRGN after PAD2 treatment. Five additional citrullination sites were observed for recombinant protein NRGN after treatment (Table 9 and Table 15). This included an additional R80 amino acid not found in the endogenous protein but had been introduced during cloning of the NRGN. These results demonstrated that all five arginine residues of human NRGN can be citrullinated in vitro. Data of MS/MS spectra of the citrullinated peptides of human NRGN not shown.

Example 9: Citrullinated Proteins in Human Brain Samples

Endogenous citrullinated sites of three brain proteins GFAP, MBP, and NRGN were identified and quantified in brain tissue samples obtained from non-Alzheimer controls (n=3) and with Alzheimer's disease (n=3) (Table 2 for clinical description). GFAP, MBP, and NRGN were identified in all of the human brain tissue samples with maximum amino acid sequence coverage of 64%, 54%, and 44% respectively. The peptide sequences and the citrullinated residues are listed in Table 11. In vivo, GFAP contained five citrullination sites at residues R30, R36, R270, R406, and R416 while MBP had fourteen residues citrullinated, including six novel arginine residues (R32, R44, R50, R92, R189, and R196). Mapping of citrullinated arginine residues demonstrated conserved in vivo citrullination of MBP R92 and R124, GFAP R406 and 416 in both the non-AZ and AZ samples and MBP R32 and GFAP R270 detected only in AZ samples. Residue R68 of NRGN was found citrullinated (representative chromatographic peak of the citrullinated and unmodified peptides containing residue R68 of human NRGN; see, FIGS. 13A-13C). With mass tolerance of 10 ppm, the citrullinated peptide can be differentiated from the C13 peak of the unmodified peptide based on the m/z value of the precursor ion.

Based on integrated peak area (FIG. 13C), occupancy rate of citrullination can be estimated by calculating the ratio of modified peptide vs. the sum of modified and unmodified peptides. It was estimated that occupancy rate of citrullinated peptide at R68 residue was 8.6% for the AD3 brain tissue sample without considering different ionization efficiency of the two peptides (FIG. 14). The occupancy rate of the endogenous citrullination site of NRGN (residue R68) and MBP (residues R92 and R124) in all brain tissue samples were determined for citrullinated peptides identified in Lys-C digests. For peptide DSHHPAR*TAHYGSLPQK (SEQ ID NO: 77) of MBP that contains residue R92, peak area of both charge +4 and charge +3 ions are included. The occupancy rates of three sites were significantly higher for AD3 and Control_1 samples. Citrullination of NRGN at residue R68 was detected in AD1, AD3, and C1 control samples. The higher ratio of citrullination may be age related.

Example 10: Citrullinated Proteins in Human Brain Samples with Stroke

Endogenous citrullination of a number of additional brain proteins were identified in brain tissue samples from a single patient from an area of normal brain and from the penumbra region of an infarcted area from a clinical stroke. Several of these citrullinated forms were only identified in the stroke tissue (Tubulin beta-4B chain, Tubulin alpha-1B chain, TPPP3, and NDRG2, Isoform 2) suggesting ischemic specific modification of these proteins.

TABLE 9

Citrullination sites of MBP, GFAP, and NRGN

| Protein, UniProt ID | Peptide | Sequence number [a] | Enzyme | In vitro site | In vivo site |
|---|---|---|---|---|---|
| MBP, bovine | YLASASTMDHAR*HGFLPR (SEQ ID NO: 84) | 12-29 | Trypsin | R23 | |
| P02687 | YLASASTMDHAR*HGFLPR*HR (SEQ ID NO: 58) | 12-31 | Trypsin | R23, R29 | |
| | YLASASTMDHAR*HGFLPR*HR* (SEQ ID NO: 60) | 12-31 | Trypsin | R23, R29, R31 | |
| | DTGILDSLGR*FFGSDR (SEQ ID NO: 14) | 32-47 | Trypsin | R41 | R41 |
| | FFGSDR*GAPK (SEQ ID NO: 85) | 42-51 | Trypsin | R47 | R47 |
| | R*GSGKDGHHAAR*TTHYGSLPQK (SEQ ID NO: 63) | 52-73 | Lys-C | R52, R63 | R63 |
| | DGHHAAR*TTHYGSLPQK (SEQ ID NO: 13) | 57-73 | Trypsin, Lys-C | R63 | R63 |
| | AQGHR*PQDENPVVHFFK (SEQ ID NO: 65) | 74-90 | Trypsin, Lys-C | R78 | |
| | NIVTPR*TPPPSQGK (SEQ ID NO: 32) | 91-104 | Trypsin, Lys-C | R96 | R96 |
| | GR*GLSLSR*FSWGAEGQK (SEQ ID NO: 66) | 105-121 | Trypsin, Lys-C | R106, R112 | |
| | PGFGYGGR*ASDYK (SEQ ID NO: 11) | 122-134 | Trypsin, Lys-C | R129 | R129 |
| | LGGR*DSR*SGSPMA(−) [c] (SEQ ID NO: 87) | 155-167 | Trypsin, Lys-C | R158, R161 | |
| | LGGR*DSR*SGSPMAR*(−) (SEQ ID NO: 89) | 155-168 | Trypsin, Lys-C | R158, R161, R168 | |
| | LGGR*DSR*SGSPMAR*R*(−) (SEQ ID NO: 83) | 155-169 | Trypsin, Lys-C | R158, R161, R168, R169 | |
| GFAP, Human | R*LGPGTR*LSLAR (SEQ ID NO: 158) | 30-41 | Trypsin | R30, R36 | R30, R36 R36 |
| P14136 | LGPGTR*LSLAR (SEQ ID NO: 93) | 31-41 | Trypsin | R36 | |
| | VR*FLEQQNK (SEQ ID NO: 40) | 87-95 | Lys-C | R88 | |
| | ALAAELNQLR*AK (SEQ ID NO: 42) | 96-107 | Lys-C | R105 | |
| | LR*LR*LDQLTANSAR*LE (SEQ ID NO: 44) | 123-138 | Glu-C | R124, R126, R136 | |
| | AENNLAAYR*QEADE (SEQ ID NO: 46) | 165-178 | Glu-C | R173 | |
| | LQEQLAR*QQVHVE (SEQ ID NO: 48) | 211-223 | Glu-C | R217 | |
| | WYR*SKFADLTDAAAR*NAE (SEQ ID NO: 50) | 256-273 | Glu-C | R258, R270 | |
| | FADLTDAAAR*NAELLR (SEQ ID NO: 95) | 261-276 | Trypsin | R270 | R270 |
| | FADLTDAAAR*NAELLR*QAK (SEQ ID NO: 97) | 261-279 | Lys-C | R270, R276 | |
| | ANDYR*R*QLQSLTCDLE (SEQ ID NO: 52) | 282-297 | Glu-C | R286, R287 | |

TABLE 9-continued

Citrullination sites of MBP, GFAP, and NRGN

| Protein, UniProt ID | Peptide | Sequence number [a] | Enzyme | In vitro site | In vivo site |
|---|---|---|---|---|---|
| | LALDIEIATYR*K (SEQ ID NO: 54) | 357-368 | Lys-C | R367 | |
| | GHLKR*NIVVKTVE (SEQ ID NO: 56) | 402-414 | Glu-C | R406 | R406 |
| | TVEMR*DGEVIK (SEQ ID NO: 98) | 412-422 | Trypsin | R416 | R416 |
| NRGN, human, Q92686 | GPGPGGPGGAGVAR*GGAGGGPSGD(-) (SEQ ID NO: 71) | 55-78 | Trypsin, Lys-C | R68 | R68 |
| | RGRKGPGPGGPGGAGVAR*GGAGGGPSGD(-) (SEQ ID NO: 99) | 51-78 | Glu-C | R68 | R68 |
| NRGN, recombinant protein [b] | IQASFR*GHMAR*K (SEQ ID NO: 101) | 33-44 | Lys-C | R38, R43 | |
| | GPGPGGPGGAGVAR*GGAGGGPSGDTR*(-) (SEQ ID NO: 102) | 55-80 | Lys-C | R68, R80 b | |
| | R*GR*KGPGPGGPGGAGVAR*GGAGGGPSGDTR*(-) (SEQ ID NO: 103) | 51-80 | Glu-C | R51, R53 R68, R80 b | |

[a] sequence number includes the initiating Met at position 1 for all proteins
[b] T79 and R80 are introduced into recombinant protein NRGN during subcloning
[c] (-) indicates the C-terminal of this protein

TABLE 10

Summary of human brain tissue samples

| Samples | CERAD [a] | BRAAK Stages | Age | Sex | Race | PMD Score | From |
|---|---|---|---|---|---|---|---|
| Control 1 | | 1 | 91 | F | W | 8 | Occ [b] |
| Control 2 | | 0 | 80 | F | W | 8 | Occ |
| Control 3 | 1 | 2 | 68 | F | W | 12 | Occ |
| AD 1 | C | 6 | 68 | F | W | 5.5 | Occ |
| AD 2 | C | 6 | 79 | F | W | 4 | Occ |
| AD 3 | C | 6 | 92 | F | W | 7 | Occ |

[a] CERAD: Consortium to establish a registry for Alzheimer's Disease
[b] Occ: occipital brain section

TABLE 11

In vivo citrullination sites of human MBP, GFAP, and NRGN

| Protein, UniProt ID | Peptide | Enzyme | In vivo site | Control [a] 1 | 2 | 3 | AD [a] 1 | 2 | 3 |
|---|---|---|---|---|---|---|---|---|---|
| MBP, human P02686-3 | YLATASTMDHAR*HGFLPR (SEQ ID NO: 104) | Trypsin | R26 | + | + | | + | + | |
| | YLATASTMDHAR*HGFLPR*HR (SEQ ID NO: 106) | Trypsin | R26, R32 | | | | + | + | |
| | HR*DTGILDSIGR (SEQ ID NO: 108) | Trypsin | R34 | + | + | + | + | + | |
| | DTGILDSIGR*FFGGDR (SEQ ID NO: 110) | Trypsin | R44 | + | + | | + | + | |
| | FFGGDR*GAPK (SEQ ID NO: 112) | Trypsin | R50 | + | + | | + | + | + |
| | DSHHPAR*TAHYGSLPQK (SEQ ID NO: 77) | Trypsin, Lys-C | R92 | + | + | + | + | + | + |
| | SHGR*TQDENPVVHFFK (SEQ ID NO: 75) | Trypsin, Lys-C | R106 | + | + | + | + | | + |

TABLE 11-continued

In vivo citrullination sites of human MBP, GFAP, and NRGN

| Protein, UniProt ID | Peptide | Enzyme | In vivo site | Control[a] 1 | 2 | 3 | AD[a] 1 | 2 | 3 |
|---|---|---|---|---|---|---|---|---|---|
| | NIVTPR*TPPPSQGK (SEQ ID NO: 32) | Trypsin, Lys-C | R124 | + | + | + | + | + | + |
| | FSWGAEGQR*PGFGYGGR (SEQ ID NO: 114) | Trypsin | R149 | + | + | | + | | + |
| | PGFGYGGR*ASDYK (SEQ ID NO: 116) | Trypsin | R157 | + | + | | + | + | + |
| | LGGR*DSR*SGSPMAR*R* (-) (SEQ ID NO: 68) | Trypsin, Lys-C | R186, R189 R196, R197 | + | | + | + | | + |
| GFAP, Human | R*LGPGTR*LSLAR (SEQ ID NO: 118) | Trypsin | R30, R36 | + | | + | + | + | |
| P14136 | LGPGTR*LSLAR (SEQ ID NO: 120) | Trypsin | R36 | + | | + | + | + | |
| | FADLTDAAAR*NAELLR (SEQ ID NO: 122) | Trypsin | R270 | | | | | + | + |
| | GHLKR*NIVVKTVE (SEQ ID NO: 30) | Glu-C | R406 | + | + | + | + | + | + |
| | TVEMR*DGEVIK (SEQ ID NO: 124) | Trypsin | R416 | + | + | + | + | + | + |
| NRGN, Human Q92686 | GPGPGGPGGAGVAR*GGAG GGPSGD(-) (SEQ ID NO: 71) | Trypsin, Lys-C | R68 | + | | | + | | + |
| | RGRKGPGPGGPGGAGVAR* GGAGGGPSGD(-) (SEQ ID NO: 99) | Glu-C | R68 | + | | | | | + |

[a] Refer to Table 2 for the details of brain tissue samples

TABLE 12

Citrullinated peptides of human GFAP after PAD2 treatment followed by trypsin, Lys-C or Glu-C digestion

| Protein, UniProt ID | Citrullinated peptide | Sequence number[a] | Theoretical m/z[b] | Experimental m/z | Enzyme | Residue |
|---|---|---|---|---|---|---|
| GFAP, human P14136 | R*LGPGTR*LSLAR (SEQ ID NO: 118) | 30-41 | 649.8806 | 649.8832 | Trypsin | R30, R36 |
| | LGPGTR*LSLAR (SEQ ID NO: 120) | 31-41 | 571.3380 | 571.3375 | Trypsin | R36 |
| | VR*FLEQQNK (SEQ ID NO: 40) | 87-95 | 581.8144 | 581.8152 | Lys-C | R88 |
| | ALAAELNQLR*AK (SEQ ID NO: 42) | 96-107 | 649.8750 | 649.8754 | Lys-C | R105 |
| | LR*LR*LDQLTANSAR*LE (SEQ ID NO: 44) | 123-138 | 936.5129 | 936.5170 | Glu-C | R124, R126, R136 |
| | AENNLAAYR*QEADE (SEQ ID NO: 46) | 165-178 | 797.8526 | 797.8555 | Glu-C | R173 |

TABLE 12-continued

Citrullinated peptides of human GFAP after PAD2 treatment
followed by trypsin, Lys-C or Glu-C digestion

| Protein, UniProt ID | Citrullinated peptide | Sequence number [a] | Theoretical m/z [b] | Experimental m/z | Enzyme | Residue |
|---|---|---|---|---|---|---|
| | LQEQLAR*QQVHVE (SEQ ID NO: 48) | 211-223 | 789.9154 | 789.9181 | Glu-C | R217 |
| | WYR*SKFADLTDAAAR*NAE (SEQ ID NO: 50) | 256-273 | 1043.9996 | 1043.9951 | Glu-C | R258, R270 |
| | FADLTDAAAR*NAELLR (SEQ ID NO: 28) | 261-276 | 874.4523 | 874.4540 | Trypsin | R270 |
| | FADLTDAAAR*NAELLR*QAK (SEQ ID NO: 97) | 261-279 | 1038.5396 | 1038.5411 | Lys-C | R270, R276 |
| | ANDYR*R*QLQSLTCDLE (SEQ ID NO: 52) | 282-297 | 992.4575 | 992.4612 | Glu-C | R286, R287 |
| | LALDIEIATYR*K (SEQ ID NO: 54) | 357-368 | 703.8981 | 703.8985 | Lys-C | R367 |
| | GHLKR*NIVVKTVE (SEQ ID NO: 30) | 402-414 | 747.4435 | 747.4455 | Glu-C | R406 |
| | TVEMR*DGEVIK (SEQ ID NO: 124) | 412-422 | 639.3239 | 639.3220 | Trypsin | R416 |

[a] sequence number includes the initiating Met at position 1
[b] mass-to-charge ratio of doubly charged ions

TABLE 13

Citrullinated peptides of bovine MBP after PAD treatment
followed by trypsin or Lys-C digestion

| Protein, UniProt ID | Citrullinated peptide | Sequence number [a] | Theoretical m/z [b] | Experimental m/z | Enzyme | Residue |
|---|---|---|---|---|---|---|
| MBP, bovine P02687 | YLASASTMDHAR*HGFLPR (SEQ ID NO: 84) | 12-29 | 677.6670 (z: +3) | 677.6676 (z: +3) | Trypsin | R23 |
| | YLASASTMDHAR*HGFLPR*HR (SEQ ID NO: 58) | 12-31 | 775.7150 (z: +3) | 775.7166 (z: +3) | Trypsin | R23, R29 |
| | YLASASTMDHAR*HGFLPR*HR* (SEQ ID NO: 60) | 12-31 | 776.0430 (z: +3) | 776.0431 (z: +3) | Trypsin | R23, R29, R31 |
| | DTGILDSLGR*FFGSDR (SEQ ID NO: 14) | 32-47 | 878.9287 | 878.9320 | Trypsin | R41 |
| | FFGSDR*GAPK (SEQ ID NO: 85) | 42-51 | 541.7669 | 541.7678 | Trypsin | R47 |
| | R*GSGKDGHHAAR*TTHYGSLPQK (SEQ ID NO: 63) | 52-73 | 591.5454 (z: +4) | 591.5466 (z: +4) | Lys-C | R52, R63 |
| | DGHHAAR*TTHYGSLPQK (SEQ ID NO: 13) | 57-73 | 938.9561 | 938.9566 | Trypsin, Lys-C | R63 |
| | AQGHR*PQDENPVVHFFK (SEQ ID NO: 65) | 74-90 | 1003.9952 | 1003.9971 | Trypsin, Lys-C | R78 |
| | NIVTPR*TPPPSQGK [c] (SEQ ID NO: 32) | 91-104 | 746.9095 | 746.9109 | Trypsin, Lys-C | R96 |
| | GR*GLSLSR*FSWGAEGQK [d] (SEQ ID NO: 66) | 105-121 | 919.4632 | 919.4651 | Trypsin, Lys-C | R106, R112 |

TABLE 13-continued

Citrullinated peptides of bovine MBP after PAD treatment followed by trypsin or Lys-C digestion

| Protein, UniProt ID | Citrullinated peptide | Sequence number [a] | Theoretical m/z [b] | Experimental m/z | Enzyme | Residue |
|---|---|---|---|---|---|---|
| | PGFGYGGR*ASDYK (SEQ ID NO: 11) | 122-134 | 688.3181 | 688.3184 | Trypsin, Lys-C | R129 |
| | LGGR*DSR*SGSPMA(−) [e] (SEQ ID NO: 87) | 155-167 | 646.7986 | 646.7998 | Trypsin, Lys-C | R158, R161 |
| | LGGR*DSR*SGSPMAR*(−) (SEQ ID NO: 89) | 155-168 | 725.3411 | 725.3438 | Trypsin, Lys-C | R158, R161, R168 |
| | LGGR*DSR*SGSPMAR*R*(−) (SEQ ID NO: 83) | 155-169 | 803.8837 | 803.8842 | Trypsin, Lys-C | R158, R161, R168, R169 |

[a] sequence number does not include the initiating Met at position 1
[b] charge state of precursor ion is +2 unless otherwise specified
[c] peptides with or without phosphorylation at T97 were both detected
[d] peptides with mono- and di-methylation at residue R106 were observed
[e] (−) indicates the C-terminal of this protein

TABLE 14

Citrullinated peptides and related unmodified peptide of neurogranin

| Protein, UniProt ID | Peptide Sequence | Seq. Number [a] | Enzyme | Theoretical m/z [b] | Exp. m/z | Residues |
|---|---|---|---|---|---|---|
| NRGN, bovine P35722 | GPGPGGPGGAGGARGGAGGG PSGD(−) (SEQ ID NO: 21) | 55-78 | Lys-C | 888.9040 | 888.9058 | NA [c] |
| | GPGPGGPGGAGGAR*GGAGG GPSGD(−) (SEQ ID NO: 22) | 55-78 | Lys-C | 889.3960 | 889.3983 | R68 |
| | GPGPGGPGGAGGAR (SEQ ID NO: 23) | 55-68 | Trypsin | 532.7652 | 532.7656 | NA |
| | KGPGPGGPGGAGGAR*GGAG GGPSGD(−) (SEQ ID NO: 23) | 54-78 | Trypsin | 953.4435 | 953.4429 | R68 |
| NRGN, human Q92686 | GPGPGGPGGAGVARGGAGGG PSGD(−) (SEQ ID NO: 24) | 54-78 | Lys-C | 909.9275 | 909.9316 | NA |
| | GPGPGGPGGAGVAR*GGAGG GPSGD(−) (SEQ ID NO: 73) | 55-78 | Trypsin, Lys-C | 910.4195 | 910.4236 | R68 |
| | RGRKGPGPGGPGGAGVARGG AGGGPSGD(−) (SEQ ID NO: 71) | 51-78 | Glu-C | 772.7270 (z: +3) | 772.7285 (z: +3) | NA |
| | RGRKGPGPGGPGGAGVAR*G GAGGGPSGD(−) (SEQ ID NO: 100) | 51-78 | Glu-C | 773.0550 (z: +3) | 773.0557 (z: +3) | R68 |
| NRGN, recombinant protein | IQASFR*GHMAR*K (SEQ ID NO: 101) | 33-44 | Lys-C | 702.3642 | 702.3629 | R38, R43 |
| | GPGPGGPGGAGVAR*GGAGG GPSGDTR*(−) (SEQ ID NO: 102) | 55-80 | Lys-C | 1039.4859 | 1039.4839 | R68, R80 |

TABLE 14-continued

Citrullinated peptides and related unmodified peptide of neurogranin

| Protein, UniProt ID | Peptide Sequence | Seq. Number [a] | Enzyme | Theoretical m/z [b] | Exp. m/z | Residues |
|---|---|---|---|---|---|---|
| | R*GR*KGPGPGGPGGAGVAR* GGAGGGPSGDTR*(-) (SEQ ID NO: 103) | 51-80 | Glu-C | 859.7553 (z: +3) | 859.7544 (z: +3) | R51, R53, R68, R80 [b] |

[a] sequence number includes the initiating Met at position 1. Met is cleaved from in the mature protein.
[b] mass-to-charge ratio of the peptide
[c] NA, not applicable for unmodified peptides

TABLE 15

In vivo citrullinated peptides of human MBP

| Protein, UniProt ID | Citrullinated peptide | Sequence number [a] | Theoretical m/z [b] | Experimental m/z | Enzyme | Residues |
|---|---|---|---|---|---|---|
| MBP, human P02686-3 | YLATASTMDHAR*HGFLPR (SEQ ID NO: 104) | 15-32 | 1023.0047 | 1023.0049 | Trypsin | R26 |
| | YLATASTMDHAR*HGFLPR*HR (SEQ ID NO: 106) | 15-34 | 780.3869 (z: +3) | 780.3881 (z: 3) | Trypsin | R26, R32 |
| | HR*DTGILDSIGR (SEQ ID NO: 108) | 33-44 | 670.8495 | 670.8501 | Trypsin | R34 |
| | DTGILDSIGR*FFGGDR (SEQ ID NO: 110) | 35-50 | 863.9234 | 863.9266 | Trypsin | R44 |
| | FFGGDR*GAPK (SEQ ID NO: 112) | 45-54 | 526.7616 | 526.7618 | Trypsin | R50 |
| | DSHHPAR*TAHYGSLPQK (SEQ ID NO: 77) | 86-102 | 951.9639 | 951.9655 | Trypsin, Lys-C | R92 |
| | SHGR*TQDENPVVHFFK (SEQ ID NO: 75) | 103-118 | 949.9608 | 949.9587 | Trypsin, Lys-C | R106 |
| | NIVTPR*TPPPSQGK (SEQ ID NO: 75) | 119-132 | 746.9095 | 746.9106 | Trypsin, Lys-C | R124 |
| | FSWGAEGQR*PGFGYGGR (SEQ ID NO: 114) | 141-157 | 915.4213 | 915.4208 | Trypsin | R149 |
| | PGFGYGGR*ASDYK (SEQ ID NO: 116) | 150-162 | 688.3184 | 688.3177 | Trypsin | R157 |
| | LGGR*DSR*SGSPMAR*R* (SEQ ID NO: 68) | 783-197 | 803.8837 | 803.8853 | Trypsin, Lys-C | R186, R189, R196, R197 |

[a] sequence number does not include the initiating Met at position 1
[b] charge state of precursor ion is +2 unless otherwise specified

TABLE 16

In vivo citrullination sites of human MBP and GFAP in brain tissue

| Protein (UniProt ID) | Peptide | Enzyme | In vivo site | Brain Sample[1] |
|---|---|---|---|---|
| MBP, human (P02686-3) | YLATASTMDHAR*HGFLPR (SEQ ID NO: 104) | Trypsin | R26 | C, S |
| | HR*DTGILDSIGR (SEQ ID NO: 108) | Trypsin | R34 | C, S |
| | FFGGDR*GAPK (SEQ ID NO: 112) | Trypsin | R50 | C, S |
| | DSHHPAR*TAHYGSLPQK (SEQ ID NO: 77) | Trypsin, Lys-C | R92 | C, S |

TABLE 16-continued

In vivo citrullination sites of human MBP and GFAP in brain tissue

| Protein (UniProt ID) | Peptide | Enzyme | In vivo site | Brain Sample[1] |
|---|---|---|---|---|
| | SHGR*TQDENPVVHFFK (SEQ ID NO: 75) | Trypsin, Lys-C | R106 | C, S |
| | NIVTPR*TPPPSQGK (SEQ ID NO: 32) | Trypsin, Lys-C | R124 | C, S |
| | FSWGAEGQR*PGFGYGGR (SEQ ID NO: 114) | Trypsin | R149 | C, S |
| | PGFGYGGR*ASDYK (SEQ ID NO: 116) | Trypsin | R157 | C, S |
| | LGGR*DSR*SGSPMAR*R* (SEQ ID NO: 68) | Lys-C | R186 R189 R196 R197 | C, S C, S C, S C, S |
| GFAP, Human (P14136) | R*LGPGTR*LSLAR (SEQ ID NO: 118) | Trypsin | R30 R36 | C, S C, S |
| | GHLKR*NIVVKTVE (SEQ ID NO: 30) | Glu-C | R406 | C, S, |
| | TVEMR*DGEVIK (SEQ ID NO: 124) | Trypsin | R416 | C, S, |
| NRGN, Human (Q92686) | IQASFR (SEQ ID NO: 126) | Trypsin | NA | C, S |
| | GPGPGGPGGAGVAR (SEQ ID NO: 70) | Trypsin | NA | C, S |
| | KGPGPGGPGGAGVAR (SEQ ID NO: 127) | Trypsin | NA | C, S |
| | GPGPGGPGGAGVARGGAGG GPSGD (SEQ ID NO: 73) | Lys-C | NA | C, S |
| | RGRKGPGPGGPGGAGVARG GAGGGPSGD (SEQ ID NO:) | Glu-C | NA | C, S |

[1]Brain tissue sample from one patient. S, brain tissue from stroke region; C: brain tissue from normal region. Extent of modification may differ between control and disease.

TABLE 17

In vivo citrullination sites of other proteins in human brain tissue (not patented yet)

| Proteins | UniProt ID | Peptide | start | stop | Residue | Brain Sample[1] |
|---|---|---|---|---|---|---|
| Tubulin beta-4B chain | P68371 | IREEYPDR*IMNTF (SEQ ID NO: 128) | 155 | 167 | R162 | S |
| Tubulin alpha-1B chain | P68363 | YMACCLLYR*GDVVPK (SEQ ID NO: 130) | 312 | 326 | R320 | C, S |
| | | VR*TGTYR*QLFHPE (SEQ ID NO: 132) | 78 | 90 | R79, R84 | S |
| CNPase | P09543 | STLAR*VIVDK (SEQ ID NO: 134) | 64 | 73 | R68 | C, S |
| | | ITPGAR*GAFSEEYK (SEQ ID NO: 136) | 88 | 101 | R93 | C, S |
| PPIA | P62937 | TAENFR*ALSTGEK (SEQ ID NO: 138) | 32 | 44 | R37 | C, S |
| Septin-7 | Q16181 | ILEQQNSSR*TLEK (SEQ ID NO: 140) | 417 | 429 | R425 | C, S |
| Elongation factor 1-alpha 2 | Q05639 | PLR*LPLQDVYK (SEQ ID NO: 142) | 245 | 255 | R247 | C, S |
| | | VYKIGGIGTVPVGR*VE (SEQ ID NO: 144) | 253 | 268 | R266 | C, S |
| TPPP | O94811 | AISSPTVSR*LTDTTK (SEQ ID NO: 146) | 157 | 171 | R165 | C, S |
| TPPP3 | Q9BW30 | TGGAVDRLTDTSR*YTGSHK (SEQ ID NO: 148) | 118 | 136 | R130 | S |
| | | GIAGR*QDILDDSGYVSAYK (SEQ ID NO: 150) | 147 | 165 | R151 | S |

TABLE 17-continued

In vivo citrullination sites of other proteins in human brain tissue (not patented yet)

| Proteins | UniProt ID | Peptide | start | stop | Residue | Brain Sample[1] |
|---|---|---|---|---|---|---|
| Ermin, Isoform 2 | Q8TAM6-2 | LTDVDSPLPHYR*VEPSLE (SEQ ID NO: 152) | 46 | 63 | R57 | C |
| NDRG2, Isoform 2 | Q9UN36-2 | TASLTSAASVDGNR*SR (SEQ ID NO: 154) | 316 | 331 | R329 | S |

[1] Brain tissue sample from one patient. S, brain tissue from stroke region; C, brain tissue from normal region.

We claim:

1. A method for detecting citrullinated brain injury biomarker proteins in a sample from a subject having or suspected of having brain injury, the method comprising:
   detecting in the subject's sample citrullinated arginine residues in citrullinated brain injury biomarker protein glial fibrillary acidic protein (GFAP) and/or citrullinated brain injury biomarker protein myelin basic protein (MBP) by detecting the citrullinated arginine residues in said citrullinated biomarker proteins using a detection method selected from mass spectrometry, immunoassay, electrochemical luminescent assay, electrochemical voltametry, electrochemical amperometry, atomic force microscopy, radio frequency multipolar resonance spectroscopy, confocal microscopy, non-confocal microscopy, fluorescence optical detection, luminescence optical detection, chemiluminescence optical detection, absorbance optical detection, reflectance optical detection, transmittance optical detection, birefringence optical detection, refractive index detection, surface plasmon resonance, ellipsometry, resonant mirror detection, grating coupler waveguide detection, or interferometry; thereby detecting citrullinated brain injury biomarker proteins in the subject's sample.

2. The method of claim 1, wherein the citrullinated GFAP is citrullinated human GFAP, which is citrullinated at one or more arginine (R) amino acid residues selected from R30, R36, R88, R105, R124, R126, R136, R173, R217, R258, R270, R276, R286, R287, R367, R406, and R416 of the human GFAP polypeptide of SEQ ID NO: 3, and the citrullinated MBP is citrullinated human MBP, which is citrullinated at one or more arginine (R) amino acid residues selected from R26, R32, R34, R44, R50, R92, R106, R124 R157, R186, R189, R196, and R197 in the human MBP polypeptide of SEQ ID NO: 163.

3. The method of claim 1, further comprising detecting citrullinated brain injury biomarker protein neurogranin (NRGN).

4. The method of claim 3, wherein the citrullinated NRGN is citrullinated human NRGN which is citrullinated at one or more arginine (R) amino acid residues selected from R38, R43, R51, R53, and R68 in the human NRGN polypeptide of SEQ ID NO: 1.

5. The method of claim 1, further comprising detecting in the subject's sample one or more citrullinated brain injury biomarker proteins selected from the group consisting of citrullinated tubulin beta-4B chain, tubulin alpha-1B chain, CNPase, PPIA, Septin-7, Elongation factor1-alpha2, TPPP, TPPP3, Ermin Isoform 2, NDRG2 Isoform 2, astrotactin 1 (ASTN1), brain angiogenesis inhibitor 3 (BAI3), carnosine dipeptidase 1 (CNDP1), ERMIN, glutamate receptor metabotropic 3 (GRM3), kelch-like protein 32 (KLH32), melanoma antigen family E,2 (MAGE2), neuregulin 3 (NRG3), oligodendrocyte myelin glycoprotein (OMG), solute carrier family 39 (zinc transporter), reticulon 1 (RTN1), MT3, and peptidylarginine deiminase types 1-4 and 6 (PAD1-4 and PAD6).

6. The method of claim 1, wherein the subject's sample is selected from the group consisting of blood, peripheral blood, serum, plasma, cerebrospinal fluid (CSF), urine, saliva, stool and synovial fluid.

7. The method of claim 1, wherein the detecting by mass spectrometry is accomplished using multiple reaction monitoring mass spectrometry (MRM-MS).

8. The method of claim 1, wherein the subject has or is suspected of having a neurodegenerative disease.

9. The method of claim 8, wherein the neurodegenerative disease is selected from hemorrhagic stroke, ischemic stroke, chronic traumatic encephalopathy, Alzheimer's disease, or Parkinson's Disease.

10. A method for detecting autoantibodies against a citrullinated brain injury biomarker protein in a sample from a subject, the method comprising the steps of:
   (a) contacting a biological sample obtained from the subject with citrullinated brain injury biomarker protein glial fibrillary acidic protein (GFAP) and/or citrullinated brain injury biomarker protein myelin basic protein (MBP); and
   (b) detecting the binding of the citrullinated GFAP and/or citrullinated MBP brain injury biomarker proteins to autoantibodies in the sample which are specific for the citrullinated brain injury biomarker proteins, said detection of binding being indicative of the presence of citrullinated brain injury biomarker protein autoantibodies.

11. The method of claim 10, wherein the citrullinated GFAP is citrullinated human GFAP, which is citrullinated at one or more arginine (R) amino acid residues selected from R30, R36, R88, R105, R124, R126, R136, R173, R217, R258, R270, R276, R286, R287, R367, R406, and R416 in the human GFAP polypeptide of SEQ ID NO: 3, and the citrullinated MBP is citrullinated human MBP, which is citrullinated at one or more arginine (R) amino acid residues selected from R26, R32, R34, R44, R50, R92, R106, R124 R157, R186, R189, R196, and R197 in the human MBP polypeptide of SEQ ID NO: 163.

12. The method of claim 10, further comprising contacting the sample with one or more citrullinated brain injury biomarker proteins selected from the group consisting of tubulin beta-4B chain, tubulin alpha-1B chain, CNPase, PPIA, Septin-7, Elongation factor1-alpha2, TPPP, TPPP3, Ermin Isoform 2, NDRG2 Isoform 2, astrotactin 1 (ASTN1), brain angiogenesis inhibitor 3 (BAI3); carnosine dipeptidase 1 (CNDP1); ERMIN; glutamate receptor metabotropic 3 (GRM3); kelch-like protein 32 (KLH32); melanoma antigen family E,2 (MAGE2); neuregulin 3 (NRG3); oligodendrocyte myelin glycoprotein (OMG); solute carrier family 39 (zinc transporter); reticulon 1 (RTN1); MT3, and peptidylarginine deiminase, types 1-4 and 6 (PAD1-4 or PAD6).

13. The method of claim 10, wherein the binding is detected by immunosorbent assay, by immunoprecipitation, or by immunoblotting.

14. The method of claim 10, further comprising contacting the biological sample obtained from the subject with citrullinated brain injury biomarker protein neurogranin (NRGN).

15. The method of claim 14, wherein the citrullinated NRGN is citrullinated human NRGN which is citrullinated at one or more arginine (R) amino acid residues selected from R38, R43, R51, R53, or R68 in the human NRGN polypeptide of SEQ ID NO: 1.

16. The method of claim 10, wherein the biological sample is blood, serum, plasma, cerebrospinal fluid (CSF), urine, saliva, stool and synovial fluid.

* * * * *

UNITED STATES PATENT AND TRADEMARK OFFICE
CERTIFICATE OF CORRECTION

PATENT NO. : 10,365,288 B2  
APPLICATION NO. : 15/636076  
DATED : July 30, 2019  
INVENTOR(S) : Jennifer Eileen Van Eyk, Allen Everett and Zhicheng Jin Page 1 of 1

It is certified that error appears in the above-identified patent and that said Letters Patent is hereby corrected as shown below:

In the Specification

Column 1, Lines 19-24, should read:
STATEMENT OF GOVERNMENTAL INTEREST
This invention was made with government support under HL091759, HL090515, and HHSN268201000032C awarded by the National Institutes of Health. The government has certain rights in the invention.

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 169

<210> SEQ ID NO 1
<211> LENGTH: 78
<212> TYPE: PRT
<213> ORGANISM: Homo sapiens
<220> FEATURE:
<223> OTHER INFORMATION: Neurogranin (NRGN) amino acid sequence

<400> SEQUENCE: 1

Met Asp Cys Cys Thr Glu Asn Ala Cys Ser Lys Pro Asp Asp Asp Ile
1               5                   10                  15

Leu Asp Ile Pro Leu Asp Asp Pro Gly Ala Asn Ala Ala Ala Ala Lys
            20                  25                  30

Ile Gln Ala Ser Phe Arg Gly His Met Ala Arg Lys Lys Ile Lys Ser
        35                  40                  45

Gly Glu Arg Gly Arg Lys Gly Pro Gly Pro Gly Gly Pro Gly Gly Ala
    50                  55                  60

Gly Val Ala Arg Gly Gly Ala Gly Gly Gly Pro Ser Gly Asp
65                  70                  75

<210> SEQ ID NO 2
<211> LENGTH: 304
<212> TYPE: PRT
<213> ORGANISM: Homo sapiens
<220> FEATURE:
<223> OTHER INFORMATION: Myelin Basic Protein (MBP) amino acid sequence

<400> SEQUENCE: 2

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
        35                  40                  45

Ala Asp Ala Asn Gln Asn Asn Gly Thr Ser Ser Gln Asp Thr Ala Val
    50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
            85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
        115                 120                 125

Glu Ser Leu Asp Val Met Ala Ser Gln Lys Arg Pro Ser Gln Arg His
    130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
                180                 185                 190

Asp Ser His His Pro Ala Arg Thr Ala His Tyr Gly Ser Leu Pro Gln
                195                 200                 205

Lys Ser His Gly Arg Thr Gln Asp Glu Asn Pro Val Val His Phe Phe
210                 215                 220

Lys Asn Ile Val Thr Pro Arg Thr Pro Pro Ser Gln Gly Lys Gly
225                 230                 235                 240

Arg Gly Leu Ser Leu Ser Arg Phe Ser Trp Gly Ala Glu Gly Gln Arg
                245                 250                 255

Pro Gly Phe Gly Tyr Gly Gly Arg Ala Ser Asp Tyr Lys Ser Ala His
                260                 265                 270

Lys Gly Phe Lys Gly Val Asp Ala Gln Gly Thr Leu Ser Lys Ile Phe
                275                 280                 285

Lys Leu Gly Gly Arg Asp Ser Arg Ser Gly Ser Pro Met Ala Arg Arg
290                 295                 300

<210> SEQ ID NO 3
<211> LENGTH: 432
<212> TYPE: PRT
<213> ORGANISM: Homo sapiens
<220> FEATURE:
<223> OTHER INFORMATION: Glial Fibrillary Acidic Protein (GFAP) amino
      acid sequence

<400> SEQUENCE: 3

Met Glu Arg Arg Arg Ile Thr Ser Ala Ala Arg Arg Ser Tyr Val Ser
1               5                   10                  15

Ser Gly Glu Met Met Val Gly Gly Leu Ala Pro Gly Arg Arg Leu Gly
                20                  25                  30

Pro Gly Thr Arg Leu Ser Leu Ala Arg Met Pro Pro Pro Leu Pro Thr
            35                  40                  45

Arg Val Asp Phe Ser Leu Ala Gly Ala Leu Asn Ala Gly Phe Lys Glu
    50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu
            100                 105                 110

Ala Asp Val Tyr Gln Ala Glu Leu Arg Glu Leu Arg Leu Arg Leu Asp
        115                 120                 125

Gln Leu Thr Ala Asn Ser Ala Arg Leu Glu Val Glu Arg Asp Asn Leu
    130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser

```
                180                 185                 190
Leu Glu Glu Glu Ile Arg Phe Leu Arg Lys Ile His Glu Glu Val
            195                 200                 205

Arg Glu Leu Gln Glu Gln Leu Ala Arg Gln Gln Val His Val Glu Leu
        210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Trp
                245                 250                 255

Tyr Arg Ser Lys Phe Ala Asp Leu Thr Asp Ala Ala Arg Asn Ala
            260                 265                 270

Glu Leu Leu Arg Gln Ala Lys His Glu Ala Asn Asp Tyr Arg Arg Gln
        275                 280                 285

Leu Gln Ser Leu Thr Cys Asp Leu Glu Ser Leu Arg Gly Thr Asn Glu
            290                 295                 300

Ser Leu Glu Arg Gln Met Arg Glu Gln Glu Arg His Val Arg Glu
305                 310                 315                 320

Ala Ala Ser Tyr Gln Glu Ala Leu Ala Arg Leu Glu Glu Gly Gln
                325                 330                 335

Ser Leu Lys Asp Glu Met Ala Arg His Leu Gln Glu Tyr Gln Asp Leu
            340                 345                 350

Leu Asn Val Lys Leu Ala Leu Asp Ile Glu Ile Ala Thr Tyr Arg Lys
            355                 360                 365

Leu Leu Glu Gly Glu Glu Asn Arg Ile Thr Ile Pro Val Gln Thr Phe
        370                 375                 380

Ser Asn Leu Gln Ile Arg Glu Thr Ser Leu Asp Thr Lys Ser Val Ser
385                 390                 395                 400

Glu Gly His Leu Lys Arg Asn Ile Val Val Lys Thr Val Glu Met Arg
                405                 410                 415

Asp Gly Glu Val Ile Lys Glu Ser Lys Gln Glu His Lys Asp Val Met
            420                 425                 430
```

<210> SEQ ID NO 4
<211> LENGTH: 665
<212> TYPE: PRT
<213> ORGANISM: Homo sapiens
<220> FEATURE:
<223> OTHER INFORMATION: Protein-arginine deiminase type-2 (PAD2) amino
      acid sequence

<400> SEQUENCE: 4

```
Met Leu Arg Glu Arg Thr Val Arg Leu Gln Tyr Gly Ser Arg Val Glu
1               5                   10                  15

Ala Val Tyr Val Leu Gly Thr Tyr Leu Trp Thr Asp Val Tyr Ser Ala
            20                  25                  30

Ala Pro Ala Gly Ala Gln Thr Phe Ser Leu Lys His Ser Glu His Val
        35                  40                  45

Trp Val Glu Val Arg Asp Gly Glu Ala Glu Val Ala Thr Asn
    50                  55                  60

Gly Lys Gln Arg Trp Leu Leu Ser Pro Ser Thr Thr Leu Arg Val Thr
65              70                  75                  80

Met Ser Gln Ala Ser Thr Glu Ala Ser Ser Asp Lys Val Thr Val Asn
                85                  90                  95

Tyr Tyr Asp Glu Glu Gly Ser Ile Pro Ile Asp Gln Ala Gly Leu Phe
            100                 105                 110
```

```
Leu Thr Ala Ile Glu Ile Ser Leu Asp Val Asp Ala Asp Arg Asp Gly
            115                 120                 125
Val Val Glu Lys Asn Asn Pro Lys Lys Ala Ser Trp Thr Trp Gly Pro
        130                 135                 140
Glu Gly Gln Gly Ala Ile Leu Leu Val Asn Cys Asp Arg Glu Thr Pro
145                 150                 155                 160
Trp Leu Pro Lys Glu Asp Cys Arg Asp Glu Lys Val Tyr Ser Lys Glu
                165                 170                 175
Asp Leu Lys Asp Met Ser Gln Met Ile Leu Arg Thr Lys Gly Pro Asp
            180                 185                 190
Arg Leu Pro Ala Gly Tyr Glu Ile Val Leu Tyr Ile Ser Met Ser Asp
        195                 200                 205
Ser Asp Lys Val Gly Val Phe Tyr Val Glu Asn Pro Phe Phe Gly Gln
210                 215                 220
Arg Tyr Ile His Ile Leu Gly Arg Arg Lys Leu Tyr His Val Val Lys
225                 230                 235                 240
Tyr Thr Gly Gly Ser Ala Glu Leu Leu Phe Phe Val Glu Gly Leu Cys
                245                 250                 255
Phe Pro Asp Glu Gly Phe Ser Gly Leu Val Ser Ile His Val Ser Leu
            260                 265                 270
Leu Glu Tyr Met Ala Gln Asp Ile Pro Leu Thr Pro Ile Phe Thr Asp
        275                 280                 285
Thr Val Ile Phe Arg Ile Ala Pro Trp Ile Met Thr Pro Asn Ile Leu
            290                 295                 300
Pro Pro Val Ser Val Phe Val Cys Cys Met Lys Asp Asn Tyr Leu Phe
305                 310                 315                 320
Leu Lys Glu Val Lys Asn Leu Val Glu Lys Thr Asn Cys Glu Leu Lys
                325                 330                 335
Val Cys Phe Gln Tyr Leu Asn Arg Gly Asp Arg Trp Ile Gln Asp Glu
            340                 345                 350
Ile Glu Phe Gly Tyr Ile Glu Ala Pro His Lys Gly Phe Pro Val Val
        355                 360                 365
Leu Asp Ser Pro Arg Asp Gly Asn Leu Lys Asp Phe Pro Val Lys Glu
370                 375                 380
Leu Leu Gly Pro Asp Phe Gly Tyr Val Thr Arg Glu Pro Leu Phe Glu
385                 390                 395                 400
Ser Val Thr Ser Leu Asp Ser Phe Gly Asn Leu Glu Val Ser Pro Pro
                405                 410                 415
Val Thr Val Asn Gly Lys Thr Tyr Pro Leu Gly Arg Ile Leu Ile Gly
            420                 425                 430
Ser Ser Phe Pro Leu Ser Gly Gly Arg Arg Met Thr Lys Val Val Arg
        435                 440                 445
Asp Phe Leu Lys Ala Gln Gln Val Gln Ala Pro Val Glu Leu Tyr Ser
450                 455                 460
Asp Trp Leu Thr Val Gly His Val Asp Glu Phe Met Ser Phe Val Pro
465                 470                 475                 480
Ile Pro Gly Thr Lys Lys Phe Leu Leu Leu Met Ala Ser Thr Ser Ala
                485                 490                 495
Cys Tyr Lys Leu Phe Arg Glu Lys Gln Lys Asp Gly His Gly Glu Ala
            500                 505                 510
Ile Met Phe Lys Gly Leu Gly Gly Met Ser Ser Lys Arg Ile Thr Ile
        515                 520                 525
Asn Lys Ile Leu Ser Asn Glu Ser Leu Val Gln Glu Asn Leu Tyr Phe
```

```
                    530                 535                 540
Gln Arg Cys Leu Asp Trp Asn Arg Asp Ile Leu Lys Lys Glu Leu Gly
545                 550                 555                 560

Leu Thr Glu Gln Asp Ile Ile Asp Leu Pro Ala Leu Phe Lys Met Asp
                565                 570                 575

Glu Asp His Arg Ala Arg Ala Phe Phe Pro Asn Met Val Asn Met Ile
                580                 585                 590

Val Leu Asp Lys Asp Leu Gly Ile Pro Lys Pro Phe Gly Pro Gln Val
            595                 600                 605

Glu Glu Glu Cys Cys Leu Glu Met His Val Arg Gly Leu Leu Glu Pro
        610                 615                 620

Leu Gly Leu Glu Cys Thr Phe Ile Asp Asp Ile Ser Ala Tyr His Lys
625                 630                 635                 640

Phe Leu Gly Glu Val His Cys Gly Thr Asn Val Arg Arg Lys Pro Phe
                645                 650                 655

Thr Phe Lys Trp Trp His Met Val Pro
            660                 665

<210> SEQ ID NO 5
<211> LENGTH: 169
<212> TYPE: PRT
<213> ORGANISM: Bos taurus
<220> FEATURE:
<223> OTHER INFORMATION: Bovine Myelin Basic Protein (MBP) amino acid
      sequence

<400> SEQUENCE: 5

Ala Ala Gln Lys Arg Pro Ser Gln Arg Ser Lys Tyr Leu Ala Ser Ala
1               5                   10                  15

Ser Thr Met Asp His Ala Arg His Gly Phe Leu Pro Arg His Arg Asp
            20                  25                  30

Thr Gly Ile Leu Asp Ser Leu Gly Arg Phe Phe Gly Ser Asp Arg Gly
        35                  40                  45

Ala Pro Lys Arg Gly Ser Gly Lys Asp Gly His His Ala Ala Arg Thr
    50                  55                  60

Thr His Tyr Gly Ser Leu Pro Gln Lys Ala Gln Gly His Arg Pro Gln
65                  70                  75                  80

Asp Glu Asn Pro Val Val His Phe Phe Lys Asn Ile Val Thr Pro Arg
                85                  90                  95

Thr Pro Pro Pro Ser Gln Gly Lys Gly Arg Gly Leu Ser Leu Ser Arg
            100                 105                 110

Phe Ser Trp Gly Ala Glu Gly Gln Lys Pro Gly Phe Gly Tyr Gly Gly
        115                 120                 125

Arg Ala Ser Asp Tyr Lys Ser Ala His Lys Gly Leu Lys Gly His Asp
    130                 135                 140

Ala Gln Gly Thr Leu Ser Lys Ile Phe Lys Leu Gly Gly Arg Asp Ser
145                 150                 155                 160

Arg Ser Gly Ser Pro Met Ala Arg Arg
                165

<210> SEQ ID NO 6
<211> LENGTH: 78
<212> TYPE: PRT
<213> ORGANISM: Bos taurus
<220> FEATURE:
<223> OTHER INFORMATION: Bovine Neurogranin (NRGN) amino acid sequence

<400> SEQUENCE: 6
```

Met Asp Cys Cys Thr Glu Ser Ala Cys Ser Lys Pro Asp Asp Ile
1               5                   10                  15

Leu Asp Ile Pro Leu Asp Asp Pro Gly Ala Asn Ala Ala Ala Lys
            20                  25                  30

Ile Gln Ala Ser Phe Arg Gly His Met Ala Arg Lys Lys Ile Lys Ser
                35                  40                  45

Gly Glu Arg Gly Arg Lys Gly Pro Gly Pro Gly Pro Gly Gly Ala
50                  55                  60

Gly Gly Ala Arg Gly Gly Ala Gly Gly Pro Ser Gly Asp
65                  70                  75

<210> SEQ ID NO 7
<211> LENGTH: 428
<212> TYPE: PRT
<213> ORGANISM: Bos taurus
<220> FEATURE:
<223> OTHER INFORMATION: Bovine Glial Fibrillary Acidic Protein (GFAP)
      amino acid sequence

<400> SEQUENCE: 7

Met Glu Arg Arg Arg Val Thr Ser Ala Thr Arg Arg Ser Tyr Val Ser
1               5                   10                  15

Ser Ser Glu Met Val Val Gly Gly Arg Arg Leu Gly Pro Gly Thr Arg
                20                  25                  30

Leu Ser Leu Ala Arg Met Pro Pro Leu Pro Ala Arg Val Asp Phe
            35                  40                  45

Ser Leu Ala Gly Ala Leu Asn Ser Gly Phe Lys Glu Thr Arg Ala Ser
50                  55                  60

Glu Arg Ala Glu Met Met Glu Leu Asn Asp Arg Phe Ala Ser Tyr Ile
65                  70                  75                  80

Glu Lys Val Arg Phe Leu Glu Gln Gln Asn Lys Ala Leu Ala Ala Glu
                85                  90                  95

Leu Asn Gln Leu Arg Ala Lys Glu Pro Thr Lys Leu Ala Asp Val Tyr
            100                 105                 110

Gln Ala Glu Leu Arg Glu Leu Arg Leu Arg Leu Asp Gln Leu Thr Ala
            115                 120                 125

Asn Ser Ala Arg Leu Glu Val Glu Arg Asp Asn Leu Ala Gln Asp Leu
130                 135                 140

Gly Thr Leu Arg Gln Lys Leu Gln Asp Glu Thr Asn Gln Arg Leu Glu
145                 150                 155                 160

Ala Glu Asn Asn Leu Ala Ala Tyr Arg Gln Glu Ala Asp Glu Ala Thr
                165                 170                 175

Leu Ala Arg Leu Asp Leu Glu Arg Lys Ile Glu Ser Leu Glu Glu Glu
            180                 185                 190

Ile Arg Phe Leu Arg Lys Ile His Glu Glu Val Arg Glu Leu Gln
            195                 200                 205

Glu Gln Leu Ala Gln Gln Val His Val Glu Met Asp Val Ala Lys
    210                 215                 220

Pro Asp Leu Thr Ala Ala Leu Arg Glu Ile Arg Thr Gln Tyr Glu Ala
225                 230                 235                 240

Val Ala Ser Ser Asn Met His Glu Ala Glu Glu Trp Tyr Arg Ser Lys
                245                 250                 255

Phe Ala Asp Leu Asn Asp Ala Ala Ala Arg Asn Ala Glu Leu Leu Arg
            260                 265                 270

Gln Ala Lys His Glu Ala Asn Asp Tyr Arg Arg Gln Leu Gln Ala Leu

```
                275                 280                 285
Thr Cys Asp Leu Glu Ser Leu Arg Gly Thr Asn Glu Ser Leu Glu Arg
    290                 295                 300

Gln Met Arg Glu Gln Glu Arg His Ala Arg Glu Ala Ala Ser Tyr
305                 310                 315                 320

Gln Glu Ala Leu Ala Arg Leu Glu Glu Gly Gln Ser Leu Lys Asp
                325                 330                 335

Glu Met Ala Arg His Leu Gln Glu Tyr Gln Asp Leu Leu Asn Val Lys
        340                 345                 350

Leu Ala Leu Asp Ile Glu Ile Ala Thr Tyr Arg Lys Leu Leu Glu Gly
            355                 360                 365

Glu Glu Asn Arg Ile Thr Ile Pro Val Gln Thr Phe Ser Asn Leu Gln
370                 375                 380

Ile Arg Glu Thr Ser Leu Asp Thr Lys Ser Val Ser Glu Gly His Leu
385                 390                 395                 400

Lys Arg Asn Ile Val Val Lys Thr Val Glu Met Arg Asp Gly Glu Val
                405                 410                 415

Ile Lys Glu Ser Lys Gln Glu His Lys Asp Val Met
            420                 425

<210> SEQ ID NO 8
<211> LENGTH: 14
<212> TYPE: PRT
<213> ORGANISM: Bos taurus
<220> FEATURE:
<223> OTHER INFORMATION: Bovine MBP peptide, amino acids 91-104

<400> SEQUENCE: 8

Asn Ile Val Thr Pro Arg Thr Pro Pro Ser Gln Gly Lys
1               5                   10

<210> SEQ ID NO 9
<211> LENGTH: 14
<212> TYPE: PRT
<213> ORGANISM: Bos taurus
<220> FEATURE:
<223> OTHER INFORMATION: Bovine MBP peptide, amino acids 91-105
<220> FEATURE:
<221> NAME/KEY: MOD_RES
<222> LOCATION: (6)..(6)
<223> OTHER INFORMATION: Citrullinated residue

<400> SEQUENCE: 9

Asn Ile Val Thr Pro Arg Thr Pro Pro Ser Gln Gly Lys
1               5                   10

<210> SEQ ID NO 10
<211> LENGTH: 13
<212> TYPE: PRT
<213> ORGANISM: Bos taurus
<220> FEATURE:
<223> OTHER INFORMATION: Bovine MBP peptide, amino acids 122-134

<400> SEQUENCE: 10

Pro Gly Phe Gly Tyr Gly Gly Arg Ala Ser Asp Tyr Lys
1               5                   10

<210> SEQ ID NO 11
<211> LENGTH: 13
<212> TYPE: PRT
<213> ORGANISM: Bos taurus
<220> FEATURE:
<223> OTHER INFORMATION: Bovine MBP peptide, amino acids 122-134
```

```
<220> FEATURE:
<221> NAME/KEY: MOD_RES
<222> LOCATION: (8)..(8)
<223> OTHER INFORMATION: Citrullinated residue

<400> SEQUENCE: 11

Pro Gly Phe Gly Tyr Gly Gly Arg Ala Ser Asp Tyr Lys
1               5                   10

<210> SEQ ID NO 12
<211> LENGTH: 17
<212> TYPE: PRT
<213> ORGANISM: Bos taurus
<220> FEATURE:
<223> OTHER INFORMATION: Bovine MBP peptide, amino acids 57-73

<400> SEQUENCE: 12

Asp Gly His His Ala Ala Arg Thr Thr His Tyr Gly Ser Leu Pro Gln
1               5                   10                  15

Lys

<210> SEQ ID NO 13
<211> LENGTH: 17
<212> TYPE: PRT
<213> ORGANISM: Bos taurus
<220> FEATURE:
<223> OTHER INFORMATION: Bovine MBP peptide, amino acids 57-73
<220> FEATURE:
<221> NAME/KEY: MOD_RES
<222> LOCATION: (7)..(7)
<223> OTHER INFORMATION: Citrullinated residue

<400> SEQUENCE: 13

Asp Gly His His Ala Ala Arg Thr Thr His Tyr Gly Ser Leu Pro Gln
1               5                   10                  15

Lys

<210> SEQ ID NO 14
<211> LENGTH: 16
<212> TYPE: PRT
<213> ORGANISM: Bos taurus
<220> FEATURE:
<223> OTHER INFORMATION: Bovine MBP peptide, amino acids 32-47
<220> FEATURE:
<221> NAME/KEY: MOD_RES
<222> LOCATION: (10)..(10)
<223> OTHER INFORMATION: Citrullinated residue

<400> SEQUENCE: 14

Asp Thr Gly Ile Leu Asp Ser Leu Gly Arg Phe Phe Gly Ser Asp Arg
1               5                   10                  15

<210> SEQ ID NO 15
<211> LENGTH: 20
<212> TYPE: PRT
<213> ORGANISM: Bos taurus
<220> FEATURE:
<223> OTHER INFORMATION: Bovine MBP peptide, amino acids 32-51
<220> FEATURE:
<221> NAME/KEY: MOD_RES
<222> LOCATION: (10)..(10)
<223> OTHER INFORMATION: Citrullinated residue
<220> FEATURE:
<221> NAME/KEY: MOD_RES
<222> LOCATION: (16)..(16)
<223> OTHER INFORMATION: Citrullinated residue

<400> SEQUENCE: 15
```

```
Asp Thr Gly Ile Leu Asp Ser Leu Gly Arg Phe Phe Gly Ser Asp Arg
1               5                   10                  15

Gly Ala Pro Lys
            20
```

<210> SEQ ID NO 16
<211> LENGTH: 6
<212> TYPE: PRT
<213> ORGANISM: Bos taurus
<220> FEATURE:
<223> OTHER INFORMATION: Bovine MBP peptide, amino acids 91-96

<400> SEQUENCE: 16

```
Asn Ile Val Thr Pro Arg
1               5
```

<210> SEQ ID NO 17
<211> LENGTH: 8
<212> TYPE: PRT
<213> ORGANISM: Bos taurus
<220> FEATURE:
<223> OTHER INFORMATION: Bovine MBP peptide, amino acids 122-129

<400> SEQUENCE: 17

```
Pro Gly Phe Gly Tyr Gly Gly Arg
1               5
```

<210> SEQ ID NO 18
<211> LENGTH: 17
<212> TYPE: PRT
<213> ORGANISM: Bos taurus
<220> FEATURE:
<223> OTHER INFORMATION: Bovine MBP peptide, amino acids 105-121

<400> SEQUENCE: 18

```
Gly Arg Gly Leu Ser Leu Ser Arg Phe Ser Trp Gly Ala Glu Gly Gln
1               5                   10                  15

Lys
```

<210> SEQ ID NO 19
<211> LENGTH: 17
<212> TYPE: PRT
<213> ORGANISM: Bos taurus
<220> FEATURE:
<223> OTHER INFORMATION: Bovine MBP peptide, amino acids 101-121
<220> FEATURE:
<221> NAME/KEY: MOD_RES
<222> LOCATION: (2)..(2)
<223> OTHER INFORMATION: Citrullinated residue
<220> FEATURE:
<221> NAME/KEY: MOD_RES
<222> LOCATION: (8)..(8)
<223> OTHER INFORMATION: Citrullinated residue

<400> SEQUENCE: 19

```
Gly Arg Gly Leu Ser Leu Ser Arg Phe Ser Trp Gly Ala Glu Gly Gln
1               5                   10                  15

Lys
```

<210> SEQ ID NO 20
<211> LENGTH: 17
<212> TYPE: PRT
<213> ORGANISM: Bos taurus
<220> FEATURE:
<223> OTHER INFORMATION: Bovine MBP peptide, amino acids 105-121
<220> FEATURE:
<221> NAME/KEY: MOD_RES

```
<222> LOCATION: (8)..(8)
<223> OTHER INFORMATION: Citrullinated residue

<400> SEQUENCE: 20

Gly Arg Gly Leu Ser Leu Ser Arg Phe Ser Trp Gly Ala Glu Gly Gln
1               5                   10                  15

Lys

<210> SEQ ID NO 21
<211> LENGTH: 24
<212> TYPE: PRT
<213> ORGANISM: Bos taurus
<220> FEATURE:
<223> OTHER INFORMATION: Bovine Neurogranin (NRGN) peptide, amino acids
      55-78

<400> SEQUENCE: 21

Gly Pro Gly Pro Gly Gly Pro Gly Gly Ala Gly Gly Ala Arg Gly Gly
1               5                   10                  15

Ala Gly Gly Pro Ser Gly Asp
            20

<210> SEQ ID NO 22
<211> LENGTH: 24
<212> TYPE: PRT
<213> ORGANISM: Bos taurus
<220> FEATURE:
<223> OTHER INFORMATION: Bovine NRGN peptide, amino acids 55-78
<220> FEATURE:
<221> NAME/KEY: MOD_RES
<222> LOCATION: (14)..(14)
<223> OTHER INFORMATION: Citrullinated residue

<400> SEQUENCE: 22

Gly Pro Gly Pro Gly Gly Pro Gly Gly Ala Gly Gly Ala Arg Gly Gly
1               5                   10                  15

Ala Gly Gly Pro Ser Gly Asp
            20

<210> SEQ ID NO 23
<211> LENGTH: 14
<212> TYPE: PRT
<213> ORGANISM: Bos taurus
<220> FEATURE:
<223> OTHER INFORMATION: Bovine NRGN peptide, amino acids 55-68

<400> SEQUENCE: 23

Gly Pro Gly Pro Gly Gly Pro Gly Gly Ala Gly Gly Ala Arg
1               5                   10

<210> SEQ ID NO 24
<211> LENGTH: 25
<212> TYPE: PRT
<213> ORGANISM: Bos taurus
<220> FEATURE:
<223> OTHER INFORMATION: Bovine NRGN peptide, amino acids 54-78
<220> FEATURE:
<221> NAME/KEY: MOD_RES
<222> LOCATION: (15)..(15)
<223> OTHER INFORMATION: Citrullinated residue

<400> SEQUENCE: 24

Lys Gly Pro Gly Pro Gly Gly Pro Gly Gly Ala Gly Gly Ala Arg Gly
1               5                   10                  15

Gly Ala Gly Gly Pro Ser Gly Asp
            20                  25
```

```
<210> SEQ ID NO 25
<211> LENGTH: 13
<212> TYPE: PRT
<213> ORGANISM: Bos taurus
<220> FEATURE:
<223> OTHER INFORMATION: Bovine GFAP peptide, amino acids 398-410

<400> SEQUENCE: 25

Gly His Leu Lys Arg Asn Ile Val Val Lys Thr Val Glu
1               5                   10

<210> SEQ ID NO 26
<211> LENGTH: 13
<212> TYPE: PRT
<213> ORGANISM: Bos taurus
<220> FEATURE:
<223> OTHER INFORMATION: Bovine GFAP peptide, amino acids 398-410
<220> FEATURE:
<221> NAME/KEY: MOD_RES
<222> LOCATION: (5)..(5)
<223> OTHER INFORMATION: Citrullinated residue

<400> SEQUENCE: 26

Gly His Leu Lys Arg Asn Ile Val Val Lys Thr Val Glu
1               5                   10

<210> SEQ ID NO 27
<211> LENGTH: 19
<212> TYPE: PRT
<213> ORGANISM: Homo sapiens
<220> FEATURE:
<223> OTHER INFORMATION: Human GFAP peptide, amino acids 261-279

<400> SEQUENCE: 27

Phe Ala Asp Leu Thr Asp Ala Ala Ala Arg Asn Ala Glu Leu Leu Arg
1               5                   10                  15

Gln Ala Lys

<210> SEQ ID NO 28
<211> LENGTH: 19
<212> TYPE: PRT
<213> ORGANISM: Homo sapiens
<220> FEATURE:
<223> OTHER INFORMATION: Human GFAP peptide, amino acids 261-279
<220> FEATURE:
<221> NAME/KEY: MOD_RES
<222> LOCATION: (10)..(10)
<223> OTHER INFORMATION: Citrullinated residue

<400> SEQUENCE: 28

Phe Ala Asp Leu Thr Asp Ala Ala Ala Arg Asn Ala Glu Leu Leu Arg
1               5                   10                  15

Gln Ala Lys

<210> SEQ ID NO 29
<211> LENGTH: 13
<212> TYPE: PRT
<213> ORGANISM: Homo sapiens
<220> FEATURE:
<223> OTHER INFORMATION: Human GFAP peptide, amino acids 402-414

<400> SEQUENCE: 29

Gly His Leu Lys Arg Asn Ile Val Val Lys Thr Val Glu
1               5                   10
```

```
<210> SEQ ID NO 30
<211> LENGTH: 13
<212> TYPE: PRT
<213> ORGANISM: Homo sapiens
<220> FEATURE:
<223> OTHER INFORMATION: Human GFAP peptide, amino acids 402-414
<220> FEATURE:
<221> NAME/KEY: MOD_RES
<222> LOCATION: (5)..(5)
<223> OTHER INFORMATION: Citrullinated residue

<400> SEQUENCE: 30

Gly His Leu Lys Arg Asn Ile Val Val Lys Thr Val Glu
1               5                   10

<210> SEQ ID NO 31
<211> LENGTH: 14
<212> TYPE: PRT
<213> ORGANISM: Homo sapiens
<220> FEATURE:
<223> OTHER INFORMATION: Human MBP peptide, amino acids 92-105

<400> SEQUENCE: 31

Asn Ile Val Thr Pro Arg Thr Pro Pro Pro Ser Gln Gly Lys
1               5                   10

<210> SEQ ID NO 32
<211> LENGTH: 14
<212> TYPE: PRT
<213> ORGANISM: Homo sapiens
<220> FEATURE:
<223> OTHER INFORMATION: Human MBP peptide, amino acids 92-105
<220> FEATURE:
<221> NAME/KEY: MOD_RES
<222> LOCATION: (6)..(6)
<223> OTHER INFORMATION: Citrullinated residue

<400> SEQUENCE: 32

Asn Ile Val Thr Pro Arg Thr Pro Pro Pro Ser Gln Gly Lys
1               5                   10

<210> SEQ ID NO 33
<211> LENGTH: 14
<212> TYPE: PRT
<213> ORGANISM: Homo sapiens
<220> FEATURE:
<223> OTHER INFORMATION: Human MBP peptide, amino acids 226-239
<220> FEATURE:
<221> NAME/KEY: MOD_RES
<222> LOCATION: (6)..(6)
<223> OTHER INFORMATION: Citrullinated residue

<400> SEQUENCE: 33

Asn Ile Val Thr Pro Arg Thr Pro Pro Pro Ser Gln Gly Lys
1               5                   10

<210> SEQ ID NO 34
<211> LENGTH: 14
<212> TYPE: PRT
<213> ORGANISM: Homo sapiens
<220> FEATURE:
<223> OTHER INFORMATION: Human MBP peptide, amino acids 226-249

<400> SEQUENCE: 34

Asn Ile Val Thr Pro Arg Thr Pro Pro Pro Ser Gln Gly Lys
1               5                   10

<210> SEQ ID NO 35
<211> LENGTH: 12
```

```
<212> TYPE: PRT
<213> ORGANISM: Homo sapiens
<220> FEATURE:
<223> OTHER INFORMATION: Human NRGN peptide, amino acids 33-44
<220> FEATURE:
<221> NAME/KEY: MOD_RES
<222> LOCATION: (6)..(6)
<223> OTHER INFORMATION: Citrullinated residue
<220> FEATURE:
<221> NAME/KEY: MOD_RES
<222> LOCATION: (11)..(11)
<223> OTHER INFORMATION: Citrullinated residue

<400> SEQUENCE: 35

Ile Gln Ala Ser Phe Arg Gly His Met Ala Arg Lys
1               5                   10

<210> SEQ ID NO 36
<211> LENGTH: 12
<212> TYPE: PRT
<213> ORGANISM: Homo sapiens
<220> FEATURE:
<223> OTHER INFORMATION: Human NRGN peptide, amino acids 33-44

<400> SEQUENCE: 36

Ile Gln Ala Ser Phe Arg Gly His Met Ala Arg Lys
1               5                   10

<210> SEQ ID NO 37
<211> LENGTH: 26
<212> TYPE: PRT
<213> ORGANISM: Homo sapiens
<220> FEATURE:
<223> OTHER INFORMATION: Human NRGN peptide, amino acids 55-80
<220> FEATURE:
<221> NAME/KEY: MOD_RES
<222> LOCATION: (14)..(14)
<223> OTHER INFORMATION: Citrullinated residue
<220> FEATURE:
<221> NAME/KEY: MOD_RES
<222> LOCATION: (26)..(26)
<223> OTHER INFORMATION: Citrullinated residue

<400> SEQUENCE: 37

Gly Pro Gly Pro Gly Gly Pro Gly Gly Ala Gly Val Ala Arg Gly Gly
1               5                   10                  15

Ala Gly Gly Gly Pro Ser Gly Asp Thr Arg
            20                  25

<210> SEQ ID NO 38
<211> LENGTH: 12
<212> TYPE: PRT
<213> ORGANISM: Bos taurus
<220> FEATURE:
<223> OTHER INFORMATION: Bovine NRGN peptide, amino acids 33-44
<220> FEATURE:
<221> NAME/KEY: MOD_RES
<222> LOCATION: (6)..(6)
<223> OTHER INFORMATION: Citrullinated residue
<220> FEATURE:
<221> NAME/KEY: MOD_RES
<222> LOCATION: (11)..(11)
<223> OTHER INFORMATION: Citrullinated residue

<400> SEQUENCE: 38

Ile Gln Ala Ser Phe Arg Gly His Met Ala Arg Lys
1               5                   10

<210> SEQ ID NO 39
<211> LENGTH: 24
```

```
<212> TYPE: PRT
<213> ORGANISM: Bos taurus
<220> FEATURE:
<223> OTHER INFORMATION: Bovine NRGN peptide, amino acids 55-78
<220> FEATURE:
<221> NAME/KEY: MOD_RES
<222> LOCATION: (14)..(14)
<223> OTHER INFORMATION: Citrullinated residue

<400> SEQUENCE: 39

Gly Pro Gly Pro Gly Gly Pro Gly Gly Ala Gly Gly Ala Arg Gly Gly
1               5                   10                  15

Ala Gly Gly Gly Pro Ser Gly Asp
            20

<210> SEQ ID NO 40
<211> LENGTH: 9
<212> TYPE: PRT
<213> ORGANISM: Homo sapiens
<220> FEATURE:
<223> OTHER INFORMATION: Human GFAP peptide, amino acids 87-95
<220> FEATURE:
<221> NAME/KEY: MOD_RES
<222> LOCATION: (2)..(2)
<223> OTHER INFORMATION: Citrullinated residue

<400> SEQUENCE: 40

Val Arg Phe Leu Glu Gln Gln Asn Lys
1               5

<210> SEQ ID NO 41
<211> LENGTH: 9
<212> TYPE: PRT
<213> ORGANISM: Homo sapiens
<220> FEATURE:
<223> OTHER INFORMATION: Human GFAP peptide, amino acids 87-95

<400> SEQUENCE: 41

Val Arg Phe Leu Glu Gln Gln Asn Lys
1               5

<210> SEQ ID NO 42
<211> LENGTH: 12
<212> TYPE: PRT
<213> ORGANISM: Homo sapiens
<220> FEATURE:
<223> OTHER INFORMATION: Human GFAP peptides, amino acids 96-107
<220> FEATURE:
<221> NAME/KEY: MOD_RES
<222> LOCATION: (10)..(10)
<223> OTHER INFORMATION: Citrullinated residue

<400> SEQUENCE: 42

Ala Leu Ala Ala Glu Leu Asn Gln Leu Arg Ala Lys
1               5                   10

<210> SEQ ID NO 43
<211> LENGTH: 12
<212> TYPE: PRT
<213> ORGANISM: Homo sapiens
<220> FEATURE:
<223> OTHER INFORMATION: Human GFAP peptide, amino acids 96-107

<400> SEQUENCE: 43

Ala Leu Ala Ala Glu Leu Asn Gln Leu Arg Ala Lys
1               5                   10

<210> SEQ ID NO 44
```

```
<211> LENGTH: 16
<212> TYPE: PRT
<213> ORGANISM: Homo sapiens
<220> FEATURE:
<223> OTHER INFORMATION: Human GFAP peptide, amino acids 123-138
<220> FEATURE:
<221> NAME/KEY: MOD_RES
<222> LOCATION: (2)..(2)
<223> OTHER INFORMATION: Citrullinated residue
<220> FEATURE:
<221> NAME/KEY: MOD_RES
<222> LOCATION: (4)..(4)
<223> OTHER INFORMATION: Citrullinated residue
<220> FEATURE:
<221> NAME/KEY: MOD_RES
<222> LOCATION: (14)..(14)
<223> OTHER INFORMATION: Citrullinated residue

<400> SEQUENCE: 44

Leu Arg Leu Arg Leu Asp Gln Leu Thr Ala Asn Ser Ala Arg Leu Glu
1               5                   10                  15

<210> SEQ ID NO 45
<211> LENGTH: 16
<212> TYPE: PRT
<213> ORGANISM: Homo sapiens
<220> FEATURE:
<223> OTHER INFORMATION: Human GFAP peptide, amino acids 123-138

<400> SEQUENCE: 45

Leu Arg Leu Arg Leu Asp Gln Leu Thr Ala Asn Ser Ala Arg Leu Glu
1               5                   10                  15

<210> SEQ ID NO 46
<211> LENGTH: 14
<212> TYPE: PRT
<213> ORGANISM: Homo sapiens
<220> FEATURE:
<223> OTHER INFORMATION: Human GFAP peptide, amino acids 165-178
<220> FEATURE:
<221> NAME/KEY: MOD_RES
<222> LOCATION: (9)..(9)
<223> OTHER INFORMATION: Citrullinated residue

<400> SEQUENCE: 46

Ala Glu Asn Asn Leu Ala Ala Tyr Arg Gln Glu Ala Asp Glu
1               5                   10

<210> SEQ ID NO 47
<211> LENGTH: 14
<212> TYPE: PRT
<213> ORGANISM: Homo sapiens
<220> FEATURE:
<223> OTHER INFORMATION: Human GFAP peptide, amino acids 165-178

<400> SEQUENCE: 47

Ala Glu Asn Asn Leu Ala Ala Tyr Arg Gln Glu Ala Asp Glu
1               5                   10

<210> SEQ ID NO 48
<211> LENGTH: 13
<212> TYPE: PRT
<213> ORGANISM: Homo sapiens
<220> FEATURE:
<223> OTHER INFORMATION: Human GFAP peptide, amino acids 211-223
<220> FEATURE:
<221> NAME/KEY: MOD_RES
<222> LOCATION: (7)..(7)
<223> OTHER INFORMATION: Citrullinated residue

<400> SEQUENCE: 48
```

```
Leu Gln Glu Gln Leu Ala Arg Gln Gln Val His Val Glu
1               5                   10
```

<210> SEQ ID NO 49
<211> LENGTH: 13
<212> TYPE: PRT
<213> ORGANISM: Homo sapiens
<220> FEATURE:
<223> OTHER INFORMATION: Human GFAP peptide, amino acids 211-223

<400> SEQUENCE: 49

```
Leu Gln Glu Gln Leu Ala Arg Gln Gln Val His Val Glu
1               5                   10
```

<210> SEQ ID NO 50
<211> LENGTH: 18
<212> TYPE: PRT
<213> ORGANISM: Homo sapiens
<220> FEATURE:
<223> OTHER INFORMATION: Human GFAP peptide, amino acids 256-273
<220> FEATURE:
<221> NAME/KEY: MOD_RES
<222> LOCATION: (3)..(3)
<223> OTHER INFORMATION: Citrullinated residue
<220> FEATURE:
<221> NAME/KEY: MOD_RES
<222> LOCATION: (15)..(15)
<223> OTHER INFORMATION: Citrullinated residue

<400> SEQUENCE: 50

```
Trp Tyr Arg Ser Lys Phe Ala Asp Leu Thr Asp Ala Ala Ala Arg Asn
1               5                   10                  15

Ala Glu
```

<210> SEQ ID NO 51
<211> LENGTH: 18
<212> TYPE: PRT
<213> ORGANISM: Homo sapiens
<220> FEATURE:
<223> OTHER INFORMATION: Human GFAP peptide, amino acids 256-273

<400> SEQUENCE: 51

```
Trp Tyr Arg Ser Lys Phe Ala Asp Leu Thr Asp Ala Ala Ala Arg Asn
1               5                   10                  15

Ala Glu
```

<210> SEQ ID NO 52
<211> LENGTH: 16
<212> TYPE: PRT
<213> ORGANISM: Homo sapiens
<220> FEATURE:
<223> OTHER INFORMATION: Human GFAP peptide, amino acids 282-297
<220> FEATURE:
<221> NAME/KEY: MOD_RES
<222> LOCATION: (5)..(6)
<223> OTHER INFORMATION: Citrullinated residue

<400> SEQUENCE: 52

```
Ala Asn Asp Tyr Arg Arg Gln Leu Gln Ser Leu Thr Cys Asp Leu Glu
1               5                   10                  15
```

<210> SEQ ID NO 53
<211> LENGTH: 16
<212> TYPE: PRT
<213> ORGANISM: Homo sapiens
<220> FEATURE:
<223> OTHER INFORMATION: Human GFAP peptide, amino acids 282-297

<400> SEQUENCE: 53

Ala Asn Asp Tyr Arg Arg Gln Leu Gln Ser Leu Thr Cys Asp Leu Glu
1               5                   10                  15

<210> SEQ ID NO 54
<211> LENGTH: 12
<212> TYPE: PRT
<213> ORGANISM: Homo sapiens
<220> FEATURE:
<223> OTHER INFORMATION: Human GFAP peptide, amino acids 357-368
<220> FEATURE:
<221> NAME/KEY: MOD_RES
<222> LOCATION: (11)..(11)
<223> OTHER INFORMATION: Citrullinated residue

<400> SEQUENCE: 54

Leu Ala Leu Asp Ile Glu Ile Ala Thr Tyr Arg Lys
1               5                   10

<210> SEQ ID NO 55
<211> LENGTH: 12
<212> TYPE: PRT
<213> ORGANISM: Homo sapiens
<220> FEATURE:
<223> OTHER INFORMATION: Human GFAP peptide, amino acids 357-368

<400> SEQUENCE: 55

Leu Ala Leu Asp Ile Glu Ile Ala Thr Tyr Arg Lys
1               5                   10

<210> SEQ ID NO 56
<211> LENGTH: 13
<212> TYPE: PRT
<213> ORGANISM: Homo sapiens
<220> FEATURE:
<223> OTHER INFORMATION: Human GFAP peptide, amino acids 402-414
<220> FEATURE:
<221> NAME/KEY: MOD_RES
<222> LOCATION: (5)..(5)
<223> OTHER INFORMATION: Citrullinated residue

<400> SEQUENCE: 56

Gly His Leu Lys Arg Asn Ile Val Val Lys Thr Val Glu
1               5                   10

<210> SEQ ID NO 57
<211> LENGTH: 13
<212> TYPE: PRT
<213> ORGANISM: Homo sapiens
<220> FEATURE:
<223> OTHER INFORMATION: Human GFAP peptide, amino acids 402-414

<400> SEQUENCE: 57

Gly His Leu Lys Arg Asn Ile Val Val Lys Thr Val Glu
1               5                   10

<210> SEQ ID NO 58
<211> LENGTH: 20
<212> TYPE: PRT
<213> ORGANISM: Bos taurus
<220> FEATURE:
<221> NAME/KEY: MOD_RES
<222> LOCATION: (12)..(12)
<223> OTHER INFORMATION: Citrullinated residue
<220> FEATURE:
<221> NAME/KEY: MOD_RES
<222> LOCATION: (18)..(18)
<223> OTHER INFORMATION: Citrullinated residue

```
<400> SEQUENCE: 58

Tyr Leu Ala Ser Ala Ser Thr Met Asp His Ala Arg His Gly Phe Leu
1               5                   10                  15

Pro Arg His Arg
            20

<210> SEQ ID NO 59
<211> LENGTH: 20
<212> TYPE: PRT
<213> ORGANISM: Homo sapiens
<220> FEATURE:
<223> OTHER INFORMATION: Human MBP peptide, amino acids 12-31

<400> SEQUENCE: 59

Tyr Leu Ala Ser Ala Ser Thr Met Asp His Ala Arg His Gly Phe Leu
1               5                   10                  15

Pro Arg His Arg
            20

<210> SEQ ID NO 60
<211> LENGTH: 20
<212> TYPE: PRT
<213> ORGANISM: Bos taurus
<220> FEATURE:
<221> NAME/KEY: MOD_RES
<222> LOCATION: (12)..(12)
<223> OTHER INFORMATION: Citrullinated residue
<220> FEATURE:
<221> NAME/KEY: MOD_RES
<222> LOCATION: (18)..(18)
<223> OTHER INFORMATION: Citrullinated residue
<220> FEATURE:
<221> NAME/KEY: MOD_RES
<222> LOCATION: (20)..(20)
<223> OTHER INFORMATION: Citrullinated residue

<400> SEQUENCE: 60

Tyr Leu Ala Ser Ala Ser Thr Met Asp His Ala Arg His Gly Phe Leu
1               5                   10                  15

Pro Arg His Arg
            20

<210> SEQ ID NO 61
<211> LENGTH: 20
<212> TYPE: PRT
<213> ORGANISM: Bos taurus
<220> FEATURE:
<221> NAME/KEY: MOD_RES
<222> LOCATION: (10)..(10)
<223> OTHER INFORMATION: Citrullinated residue
<220> FEATURE:
<221> NAME/KEY: MOD_RES
<222> LOCATION: (16)..(16)
<223> OTHER INFORMATION: Citrullinated residue

<400> SEQUENCE: 61

Asp Thr Gly Ile Leu Asp Ser Leu Gly Arg Phe Phe Gly Ser Asp Arg
1               5                   10                  15

Gly Ala Pro Lys
            20

<210> SEQ ID NO 62
<211> LENGTH: 20
<212> TYPE: PRT
<213> ORGANISM: Homo sapiens
<220> FEATURE:
```

<223> OTHER INFORMATION: Human MBP peptide, amino acids 32-51

<400> SEQUENCE: 62

Asp Thr Gly Ile Leu Asp Ser Leu Gly Arg Phe Phe Gly Ser Asp Arg
1               5                   10                  15

Gly Ala Pro Lys
            20

<210> SEQ ID NO 63
<211> LENGTH: 22
<212> TYPE: PRT
<213> ORGANISM: Bos taurus
<220> FEATURE:
<221> NAME/KEY: MOD_RES
<222> LOCATION: (1)..(1)
<223> OTHER INFORMATION: Citrullinated residue
<220> FEATURE:
<221> NAME/KEY: MOD_RES
<222> LOCATION: (12)..(12)
<223> OTHER INFORMATION: Citrullinated residue

<400> SEQUENCE: 63

Arg Gly Ser Gly Lys Asp Gly His His Ala Ala Arg Thr Thr His Tyr
1               5                   10                  15

Gly Ser Leu Pro Gln Lys
            20

<210> SEQ ID NO 64
<211> LENGTH: 22
<212> TYPE: PRT
<213> ORGANISM: Homo sapiens
<220> FEATURE:
<223> OTHER INFORMATION: Human MBP peptide, amino acids 52-73

<400> SEQUENCE: 64

Arg Gly Ser Gly Lys Asp Gly His His Ala Ala Arg Thr Thr His Tyr
1               5                   10                  15

Gly Ser Leu Pro Gln Lys
            20

<210> SEQ ID NO 65
<211> LENGTH: 17
<212> TYPE: PRT
<213> ORGANISM: Bos taurus
<220> FEATURE:
<221> NAME/KEY: MOD_RES
<222> LOCATION: (5)..(5)
<223> OTHER INFORMATION: Citrullinated residue

<400> SEQUENCE: 65

Ala Gln Gly His Arg Pro Gln Asp Glu Asn Pro Val Val His Phe Phe
1               5                   10                  15

Lys

<210> SEQ ID NO 66
<211> LENGTH: 17
<212> TYPE: PRT
<213> ORGANISM: Bos taurus
<220> FEATURE:
<221> NAME/KEY: MOD_RES
<222> LOCATION: (2)..(2)
<223> OTHER INFORMATION: Citrullinated residue
<220> FEATURE:
<221> NAME/KEY: MOD_RES
<222> LOCATION: (8)..(8)
<223> OTHER INFORMATION: Citrullinated residue

<400> SEQUENCE: 66

Gly Arg Gly Leu Ser Leu Ser Arg Phe Ser Trp Gly Ala Glu Gly Gln
1               5                   10                  15
Lys

<210> SEQ ID NO 67
<211> LENGTH: 17
<212> TYPE: PRT
<213> ORGANISM: Homo sapiens
<220> FEATURE:
<223> OTHER INFORMATION: Human MBP peptide, amino acids 105-121

<400> SEQUENCE: 67

Gly Arg Gly Leu Ser Leu Ser Arg Phe Ser Trp Gly Ala Glu Gly Gln
1               5                   10                  15
Lys

<210> SEQ ID NO 68
<211> LENGTH: 15
<212> TYPE: PRT
<213> ORGANISM: Homo sapiens
<220> FEATURE:
<223> OTHER INFORMATION: Human MBP peptide, amino acids 155-169
<220> FEATURE:
<221> NAME/KEY: MOD_RES
<222> LOCATION: (4)..(4)
<223> OTHER INFORMATION: Citrullinated residue
<220> FEATURE:
<221> NAME/KEY: MOD_RES
<222> LOCATION: (7)..(7)
<223> OTHER INFORMATION: Citrullinated residue
<220> FEATURE:
<221> NAME/KEY: MOD_RES
<222> LOCATION: (14)..(15)
<223> OTHER INFORMATION: Citrullinated residue

<400> SEQUENCE: 68

Leu Gly Gly Arg Asp Ser Arg Ser Gly Ser Pro Met Ala Arg Arg
1               5                   10                  15

<210> SEQ ID NO 69
<211> LENGTH: 15
<212> TYPE: PRT
<213> ORGANISM: Homo sapiens
<220> FEATURE:
<223> OTHER INFORMATION: Human MBP peptide, amino acids 155-169

<400> SEQUENCE: 69

Leu Gly Gly Arg Asp Ser Arg Ser Gly Ser Pro Met Ala Arg Arg
1               5                   10                  15

<210> SEQ ID NO 70
<211> LENGTH: 14
<212> TYPE: PRT
<213> ORGANISM: Homo sapiens
<220> FEATURE:
<223> OTHER INFORMATION: Human NRGN peptide

<400> SEQUENCE: 70

Gly Pro Gly Pro Gly Gly Pro Gly Gly Ala Gly Val Ala Arg
1               5                   10

<210> SEQ ID NO 71
<211> LENGTH: 24
<212> TYPE: PRT
<213> ORGANISM: Homo sapiens
<220> FEATURE:

<223> OTHER INFORMATION: Human NRGN peptide
<220> FEATURE:
<221> NAME/KEY: MOD_RES
<222> LOCATION: (14)..(14)
<223> OTHER INFORMATION: Citrullinated residue

<400> SEQUENCE: 71

Gly Pro Gly Pro Gly Gly Pro Gly Gly Ala Gly Val Ala Arg Gly Gly
1               5                   10                  15

Ala Gly Gly Gly Pro Ser Gly Asp
            20

<210> SEQ ID NO 72
<211> LENGTH: 25
<212> TYPE: PRT
<213> ORGANISM: Homo sapiens
<220> FEATURE:
<223> OTHER INFORMATION: Human NRGN peptide
<220> FEATURE:
<221> NAME/KEY: MOD_RES
<222> LOCATION: (15)..(15)
<223> OTHER INFORMATION: Citrullinated residue

<400> SEQUENCE: 72

Lys Gly Pro Gly Pro Gly Gly Pro Gly Gly Ala Gly Val Ala Arg Gly
1               5                   10                  15

Gly Ala Gly Gly Gly Pro Ser Gly Asp
            20                  25

<210> SEQ ID NO 73
<211> LENGTH: 24
<212> TYPE: PRT
<213> ORGANISM: Homo sapiens
<220> FEATURE:
<223> OTHER INFORMATION: Human NRGN peptide

<400> SEQUENCE: 73

Gly Pro Gly Pro Gly Gly Pro Gly Gly Ala Gly Val Ala Arg Gly Gly
1               5                   10                  15

Ala Gly Gly Gly Pro Ser Gly Asp
            20

<210> SEQ ID NO 74
<211> LENGTH: 16
<212> TYPE: PRT
<213> ORGANISM: Homo sapiens
<220> FEATURE:
<223> OTHER INFORMATION: Human MBP peptide

<400> SEQUENCE: 74

Ser His Gly Arg Thr Gln Asp Glu Asn Pro Val Val His Phe Phe Lys
1               5                   10                  15

<210> SEQ ID NO 75
<211> LENGTH: 16
<212> TYPE: PRT
<213> ORGANISM: Homo sapiens
<220> FEATURE:
<223> OTHER INFORMATION: Human MBP peptide
<220> FEATURE:
<221> NAME/KEY: MOD_RES
<222> LOCATION: (4)..(4)
<223> OTHER INFORMATION: Citrullinated residue

<400> SEQUENCE: 75

Ser His Gly Arg Thr Gln Asp Glu Asn Pro Val Val His Phe Phe Lys
1               5                   10                  15

```
<210> SEQ ID NO 76
<211> LENGTH: 17
<212> TYPE: PRT
<213> ORGANISM: Homo sapiens
<220> FEATURE:
<223> OTHER INFORMATION: Human MBP peptide

<400> SEQUENCE: 76

Asp Ser His His Pro Ala Arg Thr Ala His Tyr Gly Ser Leu Pro Gln
1               5                   10                  15

Lys

<210> SEQ ID NO 77
<211> LENGTH: 17
<212> TYPE: PRT
<213> ORGANISM: Homo sapiens
<220> FEATURE:
<223> OTHER INFORMATION: Human MBP peptide
<220> FEATURE:
<221> NAME/KEY: MOD_RES
<222> LOCATION: (7)..(7)
<223> OTHER INFORMATION: Citrullinated residue

<400> SEQUENCE: 77

Asp Ser His His Pro Ala Arg Thr Ala His Tyr Gly Ser Leu Pro Gln
1               5                   10                  15

Lys

<210> SEQ ID NO 78
<211> LENGTH: 30
<212> TYPE: PRT
<213> ORGANISM: Homo sapiens
<220> FEATURE:
<223> OTHER INFORMATION: Human MBP peptide

<400> SEQUENCE: 78

Gly Arg Gly Leu Ser Leu Ser Arg Phe Ser Trp Gly Ala Glu Gly Gln
1               5                   10                  15

Arg Pro Gly Phe Gly Tyr Gly Gly Arg Ala Ser Asp Tyr Lys
            20                  25                  30

<210> SEQ ID NO 79
<211> LENGTH: 30
<212> TYPE: PRT
<213> ORGANISM: Homo sapiens
<220> FEATURE:
<223> OTHER INFORMATION: Human MBP peptide
<220> FEATURE:
<221> NAME/KEY: MOD_RES
<222> LOCATION: (25)..(25)
<223> OTHER INFORMATION: Citrullinated residue

<400> SEQUENCE: 79

Gly Arg Gly Leu Ser Leu Ser Arg Phe Ser Trp Gly Ala Glu Gly Gln
1               5                   10                  15

Arg Pro Gly Phe Gly Tyr Gly Gly Arg Ala Ser Asp Tyr Lys
            20                  25                  30

<210> SEQ ID NO 80
<211> LENGTH: 30
<212> TYPE: PRT
<213> ORGANISM: Homo sapiens
<220> FEATURE:
<223> OTHER INFORMATION: Human MBP peptide
<220> FEATURE:
```

```
<221> NAME/KEY: MOD_RES
<222> LOCATION: (2)..(2)
<223> OTHER INFORMATION: Citrullinated residue
<220> FEATURE:
<221> NAME/KEY: MOD_RES
<222> LOCATION: (8)..(8)
<223> OTHER INFORMATION: Citrullinated residue
<220> FEATURE:
<221> NAME/KEY: MOD_RES
<222> LOCATION: (25)..(25)
<223> OTHER INFORMATION: Citrullinated residue

<400> SEQUENCE: 80

Gly Arg Gly Leu Ser Leu Ser Arg Phe Ser Trp Gly Ala Glu Gly Gln
1               5                   10                  15

Arg Pro Gly Phe Gly Tyr Gly Gly Arg Ala Ser Asp Tyr Lys
            20                  25                  30

<210> SEQ ID NO 81
<211> LENGTH: 10
<212> TYPE: PRT
<213> ORGANISM: Homo sapiens
<220> FEATURE:
<223> OTHER INFORMATION: Human PAD2 peptide

<400> SEQUENCE: 81

Gly Phe Pro Val Val Leu Asp Ser Pro Arg
1               5                   10

<210> SEQ ID NO 82
<211> LENGTH: 16
<212> TYPE: PRT
<213> ORGANISM: Homo sapiens
<220> FEATURE:
<223> OTHER INFORMATION: Human PAD2 peptide

<400> SEQUENCE: 82

Trp Ile Gln Asp Glu Ile Glu Phe Gly Tyr Ile Glu Ala Pro His Lys
1               5                   10                  15

<210> SEQ ID NO 83
<211> LENGTH: 15
<212> TYPE: PRT
<213> ORGANISM: Bos taurus
<220> FEATURE:
<223> OTHER INFORMATION: Bovine MBP peptide
<220> FEATURE:
<221> NAME/KEY: MOD_RES
<222> LOCATION: (4)..(4)
<223> OTHER INFORMATION: Citrullinated residue
<220> FEATURE:
<221> NAME/KEY: MOD_RES
<222> LOCATION: (7)..(7)
<223> OTHER INFORMATION: Citrullinated residue
<220> FEATURE:
<221> NAME/KEY: MOD_RES
<222> LOCATION: (14)..(15)
<223> OTHER INFORMATION: Citrullinated residue

<400> SEQUENCE: 83

Leu Gly Gly Arg Asp Ser Arg Ser Gly Ser Pro Met Ala Arg Arg
1               5                   10                  15

<210> SEQ ID NO 84
<211> LENGTH: 18
<212> TYPE: PRT
<213> ORGANISM: Bos taurus
<220> FEATURE:
<223> OTHER INFORMATION: Bovine MBP peptide, amino acids 12-29
<220> FEATURE:
```

```
<221> NAME/KEY: MOD_RES
<222> LOCATION: (12)..(12)
<223> OTHER INFORMATION: Citrullinated residue

<400> SEQUENCE: 84

Tyr Leu Ala Ser Ala Ser Thr Met Asp His Ala Arg His Gly Phe Leu
1               5                   10                  15

Pro Arg

<210> SEQ ID NO 85
<211> LENGTH: 10
<212> TYPE: PRT
<213> ORGANISM: Bos taurus
<220> FEATURE:
<223> OTHER INFORMATION: Bovine MBP peptide, amino acids 42-51
<220> FEATURE:
<221> NAME/KEY: MOD_RES
<222> LOCATION: (6)..(6)
<223> OTHER INFORMATION: Citrullinated residue

<400> SEQUENCE: 85

Phe Phe Gly Ser Asp Arg Gly Ala Pro Lys
1               5                   10

<210> SEQ ID NO 86
<211> LENGTH: 10
<212> TYPE: PRT
<213> ORGANISM: Bos taurus
<220> FEATURE:
<223> OTHER INFORMATION: Bovine MBP peptide, amino acids 42-51

<400> SEQUENCE: 86

Phe Phe Gly Ser Asp Arg Gly Ala Pro Lys
1               5                   10

<210> SEQ ID NO 87
<211> LENGTH: 13
<212> TYPE: PRT
<213> ORGANISM: Bos taurus
<220> FEATURE:
<223> OTHER INFORMATION: Bovine MBP, amino acids 155-167
<220> FEATURE:
<221> NAME/KEY: MOD_RES
<222> LOCATION: (4)..(4)
<223> OTHER INFORMATION: Citrullinated residue
<220> FEATURE:
<221> NAME/KEY: MOD_RES
<222> LOCATION: (7)..(7)
<223> OTHER INFORMATION: Citrullinated residue

<400> SEQUENCE: 87

Leu Gly Gly Arg Asp Ser Arg Ser Gly Ser Pro Met Ala
1               5                   10

<210> SEQ ID NO 88
<211> LENGTH: 13
<212> TYPE: PRT
<213> ORGANISM: Bos taurus
<220> FEATURE:
<223> OTHER INFORMATION: Bovine MBP peptides, amino acids 155-167

<400> SEQUENCE: 88

Leu Gly Gly Arg Asp Ser Arg Ser Gly Ser Pro Met Ala
1               5                   10

<210> SEQ ID NO 89
<211> LENGTH: 14
<212> TYPE: PRT
```

```
<213> ORGANISM: Bos taurus
<220> FEATURE:
<223> OTHER INFORMATION: Bovine MBP peptide, amino acids 155-168
<220> FEATURE:
<221> NAME/KEY: MOD_RES
<222> LOCATION: (4)..(4)
<223> OTHER INFORMATION: Citrullinated residue
<220> FEATURE:
<221> NAME/KEY: MOD_RES
<222> LOCATION: (7)..(7)
<223> OTHER INFORMATION: Citrullinated residue
<220> FEATURE:
<221> NAME/KEY: MOD_RES
<222> LOCATION: (14)..(14)
<223> OTHER INFORMATION: Citrullinated residue

<400> SEQUENCE: 89

Leu Gly Gly Arg Asp Ser Arg Ser Gly Ser Pro Met Ala Arg
1               5                   10

<210> SEQ ID NO 90
<211> LENGTH: 14
<212> TYPE: PRT
<213> ORGANISM: Bos taurus
<220> FEATURE:
<223> OTHER INFORMATION: Bovine MBP peptide, amino acids 155-168

<400> SEQUENCE: 90

Leu Gly Gly Arg Asp Ser Arg Ser Gly Ser Pro Met Ala Arg
1               5                   10

<210> SEQ ID NO 91
<211> LENGTH: 15
<212> TYPE: PRT
<213> ORGANISM: Bos taurus
<220> FEATURE:
<223> OTHER INFORMATION: Bovine MBP peptide, amino acids 155-169

<400> SEQUENCE: 91

Leu Gly Gly Arg Asp Ser Arg Ser Gly Ser Pro Met Ala Arg Arg
1               5                   10                  15

<210> SEQ ID NO 92
<211> LENGTH: 12
<212> TYPE: PRT
<213> ORGANISM: Homo sapiens
<220> FEATURE:
<223> OTHER INFORMATION: Human GFAP peptide, amino acids 30-41

<400> SEQUENCE: 92

Arg Leu Gly Pro Gly Thr Arg Leu Ser Leu Ala Arg
1               5                   10

<210> SEQ ID NO 93
<211> LENGTH: 11
<212> TYPE: PRT
<213> ORGANISM: Homo sapiens
<220> FEATURE:
<223> OTHER INFORMATION: Human GFAP peptide, amino acids 31-41
<220> FEATURE:
<221> NAME/KEY: MOD_RES
<222> LOCATION: (6)..(6)
<223> OTHER INFORMATION: Citrullinated residue

<400> SEQUENCE: 93

Leu Gly Pro Gly Thr Arg Leu Ser Leu Ala Arg
1               5                   10

<210> SEQ ID NO 94
```

```
<211> LENGTH: 11
<212> TYPE: PRT
<213> ORGANISM: Homo sapiens
<220> FEATURE:
<223> OTHER INFORMATION: Human GFAP peptide, amino acids 31-41

<400> SEQUENCE: 94

Leu Gly Pro Gly Thr Arg Leu Ser Leu Ala Arg
1               5                   10

<210> SEQ ID NO 95
<211> LENGTH: 16
<212> TYPE: PRT
<213> ORGANISM: Homo sapiens
<220> FEATURE:
<223> OTHER INFORMATION: Human GFAP peptide, amino acids 261-276
<220> FEATURE:
<221> NAME/KEY: MOD_RES
<222> LOCATION: (10)..(10)
<223> OTHER INFORMATION: Citrullinated residue

<400> SEQUENCE: 95

Phe Ala Asp Leu Thr Asp Ala Ala Ala Arg Asn Ala Glu Leu Leu Arg
1               5                   10                  15

<210> SEQ ID NO 96
<211> LENGTH: 16
<212> TYPE: PRT
<213> ORGANISM: Homo sapiens
<220> FEATURE:
<223> OTHER INFORMATION: Human GFAP peptide, amino acids 261-276

<400> SEQUENCE: 96

Phe Ala Asp Leu Thr Asp Ala Ala Ala Arg Asn Ala Glu Leu Leu Arg
1               5                   10                  15

<210> SEQ ID NO 97
<211> LENGTH: 19
<212> TYPE: PRT
<213> ORGANISM: Homo sapiens
<220> FEATURE:
<223> OTHER INFORMATION: Human GFAP peptide, amino acids 261-279
<220> FEATURE:
<221> NAME/KEY: MOD_RES
<222> LOCATION: (10)..(10)
<223> OTHER INFORMATION: Citrullinated residue
<220> FEATURE:
<221> NAME/KEY: MOD_RES
<222> LOCATION: (16)..(16)
<223> OTHER INFORMATION: Citrullinated residue

<400> SEQUENCE: 97

Phe Ala Asp Leu Thr Asp Ala Ala Ala Arg Asn Ala Glu Leu Leu Arg
1               5                   10                  15

Gln Ala Lys

<210> SEQ ID NO 98
<211> LENGTH: 11
<212> TYPE: PRT
<213> ORGANISM: Homo sapiens
<220> FEATURE:
<223> OTHER INFORMATION: Human GFAP peptide, amino acids 412-422
<220> FEATURE:
<221> NAME/KEY: MOD_RES
<222> LOCATION: (5)..(5)
<223> OTHER INFORMATION: Citrullinated residue

<400> SEQUENCE: 98

Thr Val Glu Met Arg Asp Gly Glu Val Ile Lys
```

<210> SEQ ID NO 99
<211> LENGTH: 28
<212> TYPE: PRT
<213> ORGANISM: Homo sapiens
<220> FEATURE:
<223> OTHER INFORMATION: Human NRGN peptide, amino acids 51-78
<220> FEATURE:
<221> NAME/KEY: MOD_RES
<222> LOCATION: (18)..(18)
<223> OTHER INFORMATION: Citrullinated residue

<400> SEQUENCE: 99

Arg Gly Arg Lys Gly Pro Gly Pro Gly Gly Pro Gly Gly Ala Gly Val
1               5                   10                  15
Ala Arg Gly Gly Ala Gly Gly Gly Pro Ser Gly Asp
            20                  25

<210> SEQ ID NO 100
<211> LENGTH: 28
<212> TYPE: PRT
<213> ORGANISM: Homo sapiens
<220> FEATURE:
<223> OTHER INFORMATION: Human NRGN peptide, amino acids 51-78

<400> SEQUENCE: 100

Arg Gly Arg Lys Gly Pro Gly Pro Gly Gly Pro Gly Gly Ala Gly Val
1               5                   10                  15
Ala Arg Gly Gly Ala Gly Gly Gly Pro Ser Gly Asp
            20                  25

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      Recombinant NRGN peptide, amino acids 33-44
<220> FEATURE:
<221> NAME/KEY: MOD_RES
<222> LOCATION: (6)..(6)
<223> OTHER INFORMATION: Citrullinated residue
<220> FEATURE:
<221> NAME/KEY: MOD_RES
<222> LOCATION: (11)..(11)
<223> OTHER INFORMATION: Citrullinated residue

<400> SEQUENCE: 101

Ile Gln Ala Ser Phe Arg Gly His Met Ala Arg Lys
1               5                   10

<210> SEQ ID NO 102
<211> LENGTH: 26
<212> TYPE: PRT
<213> ORGANISM: Artificial Sequence
<220> FEATURE:
<223> OTHER INFORMATION: Description of Artificial Sequence: Synthetic
      Recombinant NRGN peptide, amino acids 55-80
<220> FEATURE:
<221> NAME/KEY: MOD_RES
<222> LOCATION: (14)..(14)
<223> OTHER INFORMATION: Citrullinated residue
<220> FEATURE:
<221> NAME/KEY: MOD_RES
<222> LOCATION: (26)..(26)
<223> OTHER INFORMATION: Citrullinated residue

<400> SEQUENCE: 102

Gly Pro Gly Pro Gly Gly Pro Gly Gly Ala Gly Val Ala Arg Gly Gly
1               5                   10                  15

Ala Gly Gly Gly Pro Ser Gly Asp Thr Arg
            20                  25

<210> SEQ ID NO 103
<211> LENGTH: 30
<212> TYPE: PRT
<213> ORGANISM: Artificial Sequence
<220> FEATURE:
<223> OTHER INFORMATION: Description of Artificial Sequence: Synthetic
      Recombinant NRGN peptide, amino acids 51-80
<220> FEATURE:
<221> NAME/KEY: MOD_RES
<222> LOCATION: (1)..(1)
<223> OTHER INFORMATION: Citrullinated residue
<220> FEATURE:
<221> NAME/KEY: MOD_RES
<222> LOCATION: (3)..(3)
<223> OTHER INFORMATION: Citrullinated residue
<220> FEATURE:
<221> NAME/KEY: MOD_RES
<222> LOCATION: (18)..(18)
<223> OTHER INFORMATION: Citrullinated residue
<220> FEATURE:
<221> NAME/KEY: MOD_RES
<222> LOCATION: (30)..(30)
<223> OTHER INFORMATION: Citrullinated residue

<400> SEQUENCE: 103

Arg Gly Arg Lys Gly Pro Gly Pro Gly Gly Pro Gly Gly Ala Gly Val
1               5                   10                  15

Ala Arg Gly Gly Ala Gly Gly Gly Pro Ser Gly Asp Thr Arg
            20                  25                  30

<210> SEQ ID NO 104
<211> LENGTH: 18
<212> TYPE: PRT
<213> ORGANISM: Homo sapiens
<220> FEATURE:
<223> OTHER INFORMATION: Human MBP peptide
<220> FEATURE:
<221> NAME/KEY: MOD_RES
<222> LOCATION: (12)..(12)
<223> OTHER INFORMATION: Citrullinated residue

<400> SEQUENCE: 104

Tyr Leu Ala Thr Ala Ser Thr Met Asp His Ala Arg His Gly Phe Leu
1               5                   10                  15

Pro Arg

<210> SEQ ID NO 105
<211> LENGTH: 18
<212> TYPE: PRT
<213> ORGANISM: Homo sapiens
<220> FEATURE:
<223> OTHER INFORMATION: Human MBP peptide

<400> SEQUENCE: 105

Tyr Leu Ala Thr Ala Ser Thr Met Asp His Ala Arg His Gly Phe Leu
1               5                   10                  15

Pro Arg

<210> SEQ ID NO 106
<211> LENGTH: 20
<212> TYPE: PRT
<213> ORGANISM: Homo sapiens
<220> FEATURE:

```
<223> OTHER INFORMATION: Human MBP peptide
<220> FEATURE:
<221> NAME/KEY: MOD_RES
<222> LOCATION: (12)..(12)
<223> OTHER INFORMATION: Citrullinated residue
<220> FEATURE:
<221> NAME/KEY: MOD_RES
<222> LOCATION: (18)..(18)
<223> OTHER INFORMATION: Citrullinated residue

<400> SEQUENCE: 106

Tyr Leu Ala Thr Ala Ser Thr Met Asp His Ala Arg His Gly Phe Leu
1               5                   10                  15
Pro Arg His Arg
            20

<210> SEQ ID NO 107
<211> LENGTH: 20
<212> TYPE: PRT
<213> ORGANISM: Homo sapiens
<220> FEATURE:
<223> OTHER INFORMATION: Human MBP peptide

<400> SEQUENCE: 107

Tyr Leu Ala Thr Ala Ser Thr Met Asp His Ala Arg His Gly Phe Leu
1               5                   10                  15
Pro Arg His Arg
            20

<210> SEQ ID NO 108
<211> LENGTH: 12
<212> TYPE: PRT
<213> ORGANISM: Homo sapiens
<220> FEATURE:
<223> OTHER INFORMATION: Human MBP peptide
<220> FEATURE:
<221> NAME/KEY: MOD_RES
<222> LOCATION: (2)..(2)
<223> OTHER INFORMATION: Citrullinated residue

<400> SEQUENCE: 108

His Arg Asp Thr Gly Ile Leu Asp Ser Ile Gly Arg
1               5                   10

<210> SEQ ID NO 109
<211> LENGTH: 12
<212> TYPE: PRT
<213> ORGANISM: Homo sapiens
<220> FEATURE:
<223> OTHER INFORMATION: Human MBP peptide

<400> SEQUENCE: 109

His Arg Asp Thr Gly Ile Leu Asp Ser Ile Gly Arg
1               5                   10

<210> SEQ ID NO 110
<211> LENGTH: 16
<212> TYPE: PRT
<213> ORGANISM: Homo sapiens
<220> FEATURE:
<223> OTHER INFORMATION: Human MBP peptide
<220> FEATURE:
<221> NAME/KEY: MOD_RES
<222> LOCATION: (10)..(10)
<223> OTHER INFORMATION: Citrullinated residue

<400> SEQUENCE: 110

Asp Thr Gly Ile Leu Asp Ser Ile Gly Arg Phe Phe Gly Gly Asp Arg
```

```
<210> SEQ ID NO 111
<211> LENGTH: 16
<212> TYPE: PRT
<213> ORGANISM: Homo sapiens
<220> FEATURE:
<223> OTHER INFORMATION: Human MBP peptide

<400> SEQUENCE: 111

Asp Thr Gly Ile Leu Asp Ser Ile Gly Arg Phe Phe Gly Gly Asp Arg
1               5                   10                  15

<210> SEQ ID NO 112
<211> LENGTH: 10
<212> TYPE: PRT
<213> ORGANISM: Homo sapiens
<220> FEATURE:
<223> OTHER INFORMATION: Human MBP peptide
<220> FEATURE:
<221> NAME/KEY: MOD_RES
<222> LOCATION: (6)..(6)
<223> OTHER INFORMATION: Citrullinated residue

<400> SEQUENCE: 112

Phe Phe Gly Gly Asp Arg Gly Ala Pro Lys
1               5                   10

<210> SEQ ID NO 113
<211> LENGTH: 10
<212> TYPE: PRT
<213> ORGANISM: Homo sapiens
<220> FEATURE:
<223> OTHER INFORMATION: Human MBP peptide

<400> SEQUENCE: 113

Phe Phe Gly Gly Asp Arg Gly Ala Pro Lys
1               5                   10

<210> SEQ ID NO 114
<211> LENGTH: 17
<212> TYPE: PRT
<213> ORGANISM: Homo sapiens
<220> FEATURE:
<223> OTHER INFORMATION: Human MBP peptide
<220> FEATURE:
<221> NAME/KEY: MOD_RES
<222> LOCATION: (9)..(9)
<223> OTHER INFORMATION: Citrullinated residue

<400> SEQUENCE: 114

Phe Ser Trp Gly Ala Glu Gly Gln Arg Pro Gly Phe Gly Tyr Gly Gly
1               5                   10                  15

Arg

<210> SEQ ID NO 115
<211> LENGTH: 17
<212> TYPE: PRT
<213> ORGANISM: Homo sapiens
<220> FEATURE:
<223> OTHER INFORMATION: Human MBP peptide

<400> SEQUENCE: 115

Phe Ser Trp Gly Ala Glu Gly Gln Arg Pro Gly Phe Gly Tyr Gly Gly
1               5                   10                  15

Arg
```

<210> SEQ ID NO 116
<211> LENGTH: 13
<212> TYPE: PRT
<213> ORGANISM: Homo sapiens
<220> FEATURE:
<223> OTHER INFORMATION: Human MBP peptide
<220> FEATURE:
<221> NAME/KEY: MOD_RES
<222> LOCATION: (8)..(8)
<223> OTHER INFORMATION: Citrullinated residue

<400> SEQUENCE: 116

Pro Gly Phe Gly Tyr Gly Gly Arg Ala Ser Asp Tyr Lys
1               5                   10

<210> SEQ ID NO 117
<211> LENGTH: 13
<212> TYPE: PRT
<213> ORGANISM: Homo sapiens
<220> FEATURE:
<223> OTHER INFORMATION: Human MBP peptide

<400> SEQUENCE: 117

Pro Gly Phe Gly Tyr Gly Gly Arg Ala Ser Asp Tyr Lys
1               5                   10

<210> SEQ ID NO 118
<211> LENGTH: 12
<212> TYPE: PRT
<213> ORGANISM: Homo sapiens
<220> FEATURE:
<223> OTHER INFORMATION: Human GFAP peptide
<220> FEATURE:
<221> NAME/KEY: MOD_RES
<222> LOCATION: (1)..(1)
<223> OTHER INFORMATION: Citrullinated residue
<220> FEATURE:
<221> NAME/KEY: MOD_RES
<222> LOCATION: (7)..(7)
<223> OTHER INFORMATION: Citrullinated residue

<400> SEQUENCE: 118

Arg Leu Gly Pro Gly Thr Arg Leu Ser Leu Ala Arg
1               5                   10

<210> SEQ ID NO 119
<211> LENGTH: 12
<212> TYPE: PRT
<213> ORGANISM: Homo sapiens
<220> FEATURE:
<223> OTHER INFORMATION: Human GFAP peptide

<400> SEQUENCE: 119

Arg Leu Gly Pro Gly Thr Arg Leu Ser Leu Ala Arg
1               5                   10

<210> SEQ ID NO 120
<211> LENGTH: 11
<212> TYPE: PRT
<213> ORGANISM: Homo sapiens
<220> FEATURE:
<223> OTHER INFORMATION: Human GFAP peptide
<220> FEATURE:
<221> NAME/KEY: MOD_RES
<222> LOCATION: (6)..(6)
<223> OTHER INFORMATION: Citrullinated residue

<400> SEQUENCE: 120

Leu Gly Pro Gly Thr Arg Leu Ser Leu Ala Arg

```
1               5                   10

<210> SEQ ID NO 121
<211> LENGTH: 11
<212> TYPE: PRT
<213> ORGANISM: Homo sapiens
<220> FEATURE:
<223> OTHER INFORMATION: Human GFAP peptide

<400> SEQUENCE: 121

Leu Gly Pro Gly Thr Arg Leu Ser Leu Ala Arg
1               5                   10

<210> SEQ ID NO 122
<211> LENGTH: 16
<212> TYPE: PRT
<213> ORGANISM: Homo sapiens
<220> FEATURE:
<223> OTHER INFORMATION: Human GFAP peptide
<220> FEATURE:
<221> NAME/KEY: MOD_RES
<222> LOCATION: (10)..(10)
<223> OTHER INFORMATION: Citrullinated residue

<400> SEQUENCE: 122

Phe Ala Asp Leu Thr Asp Ala Ala Ala Arg Asn Ala Glu Leu Leu Arg
1               5                   10                  15

<210> SEQ ID NO 123
<211> LENGTH: 16
<212> TYPE: PRT
<213> ORGANISM: Homo sapiens
<220> FEATURE:
<223> OTHER INFORMATION: Human GFAP peptide

<400> SEQUENCE: 123

Phe Ala Asp Leu Thr Asp Ala Ala Ala Arg Asn Ala Glu Leu Leu Arg
1               5                   10                  15

<210> SEQ ID NO 124
<211> LENGTH: 11
<212> TYPE: PRT
<213> ORGANISM: Homo sapiens
<220> FEATURE:
<223> OTHER INFORMATION: Human GFAP peptide
<220> FEATURE:
<221> NAME/KEY: MOD_RES
<222> LOCATION: (5)..(5)
<223> OTHER INFORMATION: Citrullinated residue

<400> SEQUENCE: 124

Thr Val Glu Met Arg Asp Gly Glu Val Ile Lys
1               5                   10

<210> SEQ ID NO 125
<211> LENGTH: 11
<212> TYPE: PRT
<213> ORGANISM: Homo sapiens
<220> FEATURE:
<223> OTHER INFORMATION: Human GFAP peptide

<400> SEQUENCE: 125

Thr Val Glu Met Arg Asp Gly Glu Val Ile Lys
1               5                   10

<210> SEQ ID NO 126
<211> LENGTH: 6
<212> TYPE: PRT
```

```
<213> ORGANISM: Homo sapiens
<220> FEATURE:
<223> OTHER INFORMATION: Human NRGN peptide

<400> SEQUENCE: 126

Ile Gln Ala Ser Phe Arg
1               5

<210> SEQ ID NO 127
<211> LENGTH: 15
<212> TYPE: PRT
<213> ORGANISM: Homo sapiens
<220> FEATURE:
<223> OTHER INFORMATION: Human NRGN peptide

<400> SEQUENCE: 127

Lys Gly Pro Gly Pro Gly Gly Pro Gly Gly Ala Gly Val Ala Arg
1               5                   10                  15

<210> SEQ ID NO 128
<211> LENGTH: 13
<212> TYPE: PRT
<213> ORGANISM: Homo sapiens
<220> FEATURE:
<223> OTHER INFORMATION: Human Tubulin beta-4B chain peptide
<220> FEATURE:
<221> NAME/KEY: MOD_RES
<222> LOCATION: (8)..(8)
<223> OTHER INFORMATION: Citrullinated residue

<400> SEQUENCE: 128

Ile Arg Glu Glu Tyr Pro Asp Arg Ile Met Asn Thr Phe
1               5                   10

<210> SEQ ID NO 129
<211> LENGTH: 13
<212> TYPE: PRT
<213> ORGANISM: Homo sapiens
<220> FEATURE:
<223> OTHER INFORMATION: Human Tubulin beta-4B chain peptide

<400> SEQUENCE: 129

Ile Arg Glu Glu Tyr Pro Asp Arg Ile Met Asn Thr Phe
1               5                   10

<210> SEQ ID NO 130
<211> LENGTH: 15
<212> TYPE: PRT
<213> ORGANISM: Homo sapiens
<220> FEATURE:
<223> OTHER INFORMATION: Human Tubulin alpha-1B chain peptide
<220> FEATURE:
<221> NAME/KEY: MOD_RES
<222> LOCATION: (9)..(9)
<223> OTHER INFORMATION: Citrullinated residue

<400> SEQUENCE: 130

Tyr Met Ala Cys Cys Leu Leu Tyr Arg Gly Asp Val Val Pro Lys
1               5                   10                  15

<210> SEQ ID NO 131
<211> LENGTH: 15
<212> TYPE: PRT
<213> ORGANISM: Homo sapiens
<220> FEATURE:
<223> OTHER INFORMATION: Human tubulin alpha-1B chain peptide

<400> SEQUENCE: 131
```

Tyr Met Ala Cys Cys Leu Leu Tyr Arg Gly Asp Val Val Pro Lys
1               5                   10                  15

<210> SEQ ID NO 132
<211> LENGTH: 13
<212> TYPE: PRT
<213> ORGANISM: Homo sapiens
<220> FEATURE:
<223> OTHER INFORMATION: Human tubulin alpha-1B chain peptide
<220> FEATURE:
<221> NAME/KEY: MOD_RES
<222> LOCATION: (2)..(2)
<223> OTHER INFORMATION: Citrullinated residue
<220> FEATURE:
<221> NAME/KEY: MOD_RES
<222> LOCATION: (7)..(7)
<223> OTHER INFORMATION: Citrullinated residue

<400> SEQUENCE: 132

Val Arg Thr Gly Thr Tyr Arg Gln Leu Phe His Pro Glu
1               5                   10

<210> SEQ ID NO 133
<211> LENGTH: 13
<212> TYPE: PRT
<213> ORGANISM: Homo sapiens
<220> FEATURE:
<223> OTHER INFORMATION: Human tubulin alpha-1B chain

<400> SEQUENCE: 133

Val Arg Thr Gly Thr Tyr Arg Gln Leu Phe His Pro Glu
1               5                   10

<210> SEQ ID NO 134
<211> LENGTH: 10
<212> TYPE: PRT
<213> ORGANISM: Homo sapiens
<220> FEATURE:
<223> OTHER INFORMATION: Human CNPase peptide
<220> FEATURE:
<221> NAME/KEY: MOD_RES
<222> LOCATION: (5)..(5)
<223> OTHER INFORMATION: Citrullinated residue

<400> SEQUENCE: 134

Ser Thr Leu Ala Arg Val Ile Val Asp Lys
1               5                   10

<210> SEQ ID NO 135
<211> LENGTH: 10
<212> TYPE: PRT
<213> ORGANISM: Homo sapiens
<220> FEATURE:
<223> OTHER INFORMATION: Human CNPase peptide

<400> SEQUENCE: 135

Ser Thr Leu Ala Arg Val Ile Val Asp Lys
1               5                   10

<210> SEQ ID NO 136
<211> LENGTH: 14
<212> TYPE: PRT
<213> ORGANISM: Homo sapiens
<220> FEATURE:
<223> OTHER INFORMATION: Human CNPase peptide
<220> FEATURE:
<221> NAME/KEY: MOD_RES
<222> LOCATION: (6)..(6)
<223> OTHER INFORMATION: Citrullinated residue

```
<400> SEQUENCE: 136

Ile Thr Pro Gly Ala Arg Gly Ala Phe Ser Glu Glu Tyr Lys
1               5                   10

<210> SEQ ID NO 137
<211> LENGTH: 14
<212> TYPE: PRT
<213> ORGANISM: Homo sapiens
<220> FEATURE:
<223> OTHER INFORMATION: Human CNPase peptide

<400> SEQUENCE: 137

Ile Thr Pro Gly Ala Arg Gly Ala Phe Ser Glu Glu Tyr Lys
1               5                   10

<210> SEQ ID NO 138
<211> LENGTH: 13
<212> TYPE: PRT
<213> ORGANISM: Homo sapiens
<220> FEATURE:
<223> OTHER INFORMATION: Human PPIA peptide
<220> FEATURE:
<221> NAME/KEY: MOD_RES
<222> LOCATION: (6)..(6)
<223> OTHER INFORMATION: Citrullinated residue

<400> SEQUENCE: 138

Thr Ala Glu Asn Phe Arg Ala Leu Ser Thr Gly Glu Lys
1               5                   10

<210> SEQ ID NO 139
<211> LENGTH: 13
<212> TYPE: PRT
<213> ORGANISM: Homo sapiens
<220> FEATURE:
<223> OTHER INFORMATION: Human PPIA peptide

<400> SEQUENCE: 139

Thr Ala Glu Asn Phe Arg Ala Leu Ser Thr Gly Glu Lys
1               5                   10

<210> SEQ ID NO 140
<211> LENGTH: 13
<212> TYPE: PRT
<213> ORGANISM: Homo sapiens
<220> FEATURE:
<223> OTHER INFORMATION: Human Septin-7 peptide
<220> FEATURE:
<221> NAME/KEY: MOD_RES
<222> LOCATION: (9)..(9)
<223> OTHER INFORMATION: Citrullinated residue

<400> SEQUENCE: 140

Ile Leu Glu Gln Gln Asn Ser Ser Arg Thr Leu Glu Lys
1               5                   10

<210> SEQ ID NO 141
<211> LENGTH: 13
<212> TYPE: PRT
<213> ORGANISM: Homo sapiens
<220> FEATURE:
<223> OTHER INFORMATION: Human Septin-7 peptide

<400> SEQUENCE: 141

Ile Leu Glu Gln Gln Asn Ser Ser Arg Thr Leu Glu Lys
1               5                   10
```

```
<210> SEQ ID NO 142
<211> LENGTH: 11
<212> TYPE: PRT
<213> ORGANISM: Homo sapiens
<220> FEATURE:
<223> OTHER INFORMATION: Human Elongation factor 1-alpha 2 peptide
<220> FEATURE:
<221> NAME/KEY: MOD_RES
<222> LOCATION: (3)..(3)
<223> OTHER INFORMATION: Citrullinated residue

<400> SEQUENCE: 142

Pro Leu Arg Leu Pro Leu Gln Asp Val Tyr Lys
1               5                   10

<210> SEQ ID NO 143
<211> LENGTH: 11
<212> TYPE: PRT
<213> ORGANISM: Homo sapiens
<220> FEATURE:
<223> OTHER INFORMATION: Human elongation factor1-alpha 2

<400> SEQUENCE: 143

Pro Leu Arg Leu Pro Leu Gln Asp Val Tyr Lys
1               5                   10

<210> SEQ ID NO 144
<211> LENGTH: 16
<212> TYPE: PRT
<213> ORGANISM: Homo sapiens
<220> FEATURE:
<223> OTHER INFORMATION: Human elongation factor 1-alpha 2 peptide
<220> FEATURE:
<221> NAME/KEY: MOD_RES
<222> LOCATION: (14)..(14)
<223> OTHER INFORMATION: Citrullinated residue

<400> SEQUENCE: 144

Val Tyr Lys Ile Gly Gly Ile Gly Thr Val Pro Val Gly Arg Val Glu
1               5                   10                  15

<210> SEQ ID NO 145
<211> LENGTH: 16
<212> TYPE: PRT
<213> ORGANISM: Homo sapiens
<220> FEATURE:
<223> OTHER INFORMATION: Human elongation factor 1-alpha 2 peptide

<400> SEQUENCE: 145

Val Tyr Lys Ile Gly Gly Ile Gly Thr Val Pro Val Gly Arg Val Glu
1               5                   10                  15

<210> SEQ ID NO 146
<211> LENGTH: 15
<212> TYPE: PRT
<213> ORGANISM: Homo sapiens
<220> FEATURE:
<223> OTHER INFORMATION: Human TPPP peptide
<220> FEATURE:
<221> NAME/KEY: MOD_RES
<222> LOCATION: (9)..(9)
<223> OTHER INFORMATION: Citrullinated residue

<400> SEQUENCE: 146

Ala Ile Ser Ser Pro Thr Val Ser Arg Leu Thr Asp Thr Thr Lys
1               5                   10                  15

<210> SEQ ID NO 147
<211> LENGTH: 15
```

```
<212> TYPE: PRT
<213> ORGANISM: Homo sapiens
<220> FEATURE:
<223> OTHER INFORMATION: Human TPPP peptide

<400> SEQUENCE: 147

Ala Ile Ser Ser Pro Thr Val Ser Arg Leu Thr Asp Thr Thr Lys
1               5                   10                  15

<210> SEQ ID NO 148
<211> LENGTH: 19
<212> TYPE: PRT
<213> ORGANISM: Homo sapiens
<220> FEATURE:
<223> OTHER INFORMATION: Human TPPP3 peptide
<220> FEATURE:
<221> NAME/KEY: MOD_RES
<222> LOCATION: (13)..(13)
<223> OTHER INFORMATION: Citrullinated residue

<400> SEQUENCE: 148

Thr Gly Gly Ala Val Asp Arg Leu Thr Asp Thr Ser Arg Tyr Thr Gly
1               5                   10                  15

Ser His Lys

<210> SEQ ID NO 149
<211> LENGTH: 19
<212> TYPE: PRT
<213> ORGANISM: Homo sapiens
<220> FEATURE:
<223> OTHER INFORMATION: Human TPPP3 petpide

<400> SEQUENCE: 149

Thr Gly Gly Ala Val Asp Arg Leu Thr Asp Thr Ser Arg Tyr Thr Gly
1               5                   10                  15

Ser His Lys

<210> SEQ ID NO 150
<211> LENGTH: 19
<212> TYPE: PRT
<213> ORGANISM: Homo sapiens
<220> FEATURE:
<223> OTHER INFORMATION: Human TPPP3 peptide
<220> FEATURE:
<221> NAME/KEY: MOD_RES
<222> LOCATION: (5)..(5)
<223> OTHER INFORMATION: Citrullinated residue

<400> SEQUENCE: 150

Gly Ile Ala Gly Arg Gln Asp Ile Leu Asp Asp Ser Gly Tyr Val Ser
1               5                   10                  15

Ala Tyr Lys

<210> SEQ ID NO 151
<211> LENGTH: 19
<212> TYPE: PRT
<213> ORGANISM: Homo sapiens
<220> FEATURE:
<223> OTHER INFORMATION: Human TPPP3 peptide

<400> SEQUENCE: 151

Gly Ile Ala Gly Arg Gln Asp Ile Leu Asp Asp Ser Gly Tyr Val Ser
1               5                   10                  15

Ala Tyr Lys
```

```
<210> SEQ ID NO 152
<211> LENGTH: 18
<212> TYPE: PRT
<213> ORGANISM: Homo sapiens
<220> FEATURE:
<223> OTHER INFORMATION: Human Ermin, Isoform 2
<220> FEATURE:
<221> NAME/KEY: MOD_RES
<222> LOCATION: (12)..(12)
<223> OTHER INFORMATION: Citrullinated residue

<400> SEQUENCE: 152

Leu Thr Asp Val Asp Ser Pro Leu Pro His Tyr Arg Val Glu Pro Ser
1               5                   10                  15

Leu Glu

<210> SEQ ID NO 153
<211> LENGTH: 18
<212> TYPE: PRT
<213> ORGANISM: Homo sapiens
<220> FEATURE:
<223> OTHER INFORMATION: Human Ermin, Isoform2

<400> SEQUENCE: 153

Leu Thr Asp Val Asp Ser Pro Leu Pro His Tyr Arg Val Glu Pro Ser
1               5                   10                  15

Leu Glu

<210> SEQ ID NO 154
<211> LENGTH: 16
<212> TYPE: PRT
<213> ORGANISM: Homo sapiens
<220> FEATURE:
<223> OTHER INFORMATION: Human NDRG2, Isoform2 peptide
<220> FEATURE:
<221> NAME/KEY: MOD_RES
<222> LOCATION: (14)..(14)
<223> OTHER INFORMATION: Citrullinated residue

<400> SEQUENCE: 154

Thr Ala Ser Leu Thr Ser Ala Ala Ser Val Asp Gly Asn Arg Ser Arg
1               5                   10                  15

<210> SEQ ID NO 155
<211> LENGTH: 16
<212> TYPE: PRT
<213> ORGANISM: Homo sapiens
<220> FEATURE:
<223> OTHER INFORMATION: Human NDRG2, Isoform 2

<400> SEQUENCE: 155

Thr Ala Ser Leu Thr Ser Ala Ala Ser Val Asp Gly Asn Arg Ser Arg
1               5                   10                  15

<210> SEQ ID NO 156
<211> LENGTH: 17
<212> TYPE: PRT
<213> ORGANISM: Homo sapiens
<220> FEATURE:
<223> OTHER INFORMATION: Human MBP peptide, amino acids 74-90

<400> SEQUENCE: 156

Ala Gln Gly His Arg Pro Gln Asp Glu Asn Pro Val Val His Phe Phe
1               5                   10                  15

Lys
```

```
<210> SEQ ID NO 157
<211> LENGTH: 26
<212> TYPE: PRT
<213> ORGANISM: Homo sapiens
<220> FEATURE:
<223> OTHER INFORMATION: Human NRGN peptide, amino acids 55-80

<400> SEQUENCE: 157

Gly Pro Gly Pro Gly Gly Pro Gly Gly Ala Gly Val Ala Arg Gly Gly
1               5                   10                  15

Ala Gly Gly Gly Pro Ser Gly Asp Thr Arg
            20                  25

<210> SEQ ID NO 158
<211> LENGTH: 12
<212> TYPE: PRT
<213> ORGANISM: Homo sapiens
<220> FEATURE:
<223> OTHER INFORMATION: Human GFAP peptide, amino acids 30-41
<220> FEATURE:
<221> NAME/KEY: MOD_RES
<222> LOCATION: (1)..(1)
<223> OTHER INFORMATION: Citrullinated residue
<220> FEATURE:
<221> NAME/KEY: MOD_RES
<222> LOCATION: (7)..(7)
<223> OTHER INFORMATION: Citrullinated residue

<400> SEQUENCE: 158

Arg Leu Gly Pro Gly Thr Arg Leu Ser Leu Ala Arg
1               5                   10

<210> SEQ ID NO 159
<211> LENGTH: 25
<212> TYPE: PRT
<213> ORGANISM: Homo sapiens
<220> FEATURE:
<223> OTHER INFORMATION: Human NRGN peptide

<400> SEQUENCE: 159

Lys Gly Pro Gly Pro Gly Gly Pro Gly Gly Ala Gly Val Ala Arg Gly
1               5                   10                  15

Gly Ala Gly Gly Gly Pro Ser Gly Asp
            20                  25

<210> SEQ ID NO 160
<211> LENGTH: 11
<212> TYPE: PRT
<213> ORGANISM: Homo sapiens
<220> FEATURE:
<223> OTHER INFORMATION: Human GFAP peptide, amino acids 412-422

<400> SEQUENCE: 160

Thr Val Glu Met Arg Asp Gly Glu Val Ile Lys
1               5                   10

<210> SEQ ID NO 161
<211> LENGTH: 97
<212> TYPE: PRT
<213> ORGANISM: Artificial Sequence
<220> FEATURE:
<223> OTHER INFORMATION: Description of Artificial Sequence: Synthetic
      Recombinant human NRGN protein

<400> SEQUENCE: 161

Met His His His His His His Glu Asn Leu Tyr Phe Gln Gly Ala Ile
1               5                   10                  15
```

```
Ala Met Asp Cys Cys Thr Glu Asn Ala Cys Ser Lys Pro Asp Asp
            20                  25                  30
Ile Leu Asp Ile Pro Leu Asp Asp Pro Gly Ala Asn Ala Ala Ala
            35                  40                  45
Lys Ile Gln Ala Ser Phe Arg Gly His Met Ala Arg Lys Ile Lys
50                  55                  60
Ser Gly Glu Arg Gly Arg Lys Gly Pro Gly Pro Gly Pro Gly Gly
65                  70                  75                  80
Ala Gly Val Ala Arg Gly Gly Ala Gly Gly Pro Ser Gly Asp Thr
            85                  90                  95
Arg

<210> SEQ ID NO 162
<211> LENGTH: 170
<212> TYPE: PRT
<213> ORGANISM: Homo sapiens

<400> SEQUENCE: 162

Ala Ser Gln Lys Arg Pro Ser Gln Arg His Gly Ser Lys Tyr Leu Ala
1               5                   10                  15
Thr Ala Ser Thr Met Asp His Ala Arg His Gly Phe Leu Pro Arg His
            20                  25                  30
Arg Asp Thr Gly Ile Leu Asp Ser Ile Gly Arg Phe Phe Gly Gly Asp
        35                  40                  45
Arg Gly Ala Pro Lys Arg Gly Ser Gly Lys Asp Ser His His Pro Ala
    50                  55                  60
Arg Thr Ala His Tyr Gly Ser Leu Pro Gln Lys Ser His Gly Arg Thr
65                  70                  75                  80
Gln Asp Glu Asn Pro Val Val His Phe Phe Lys Asn Ile Val Thr Pro
                85                  90                  95
Arg Thr Pro Pro Pro Ser Gln Gly Lys Gly Arg Gly Leu Ser Leu Ser
            100                 105                 110
Arg Phe Ser Trp Gly Ala Glu Gly Gln Arg Pro Gly Phe Gly Tyr Gly
        115                 120                 125
Gly Arg Ala Ser Asp Tyr Lys Ser Ala His Lys Gly Phe Lys Gly Val
    130                 135                 140
Asp Ala Gln Gly Thr Leu Ser Lys Ile Phe Lys Leu Gly Gly Arg Asp
145                 150                 155                 160
Ser Arg Ser Gly Ser Pro Met Ala Arg Arg
                165                 170

<210> SEQ ID NO 163
<211> LENGTH: 171
<212> TYPE: PRT
<213> ORGANISM: Homo sapiens
<220> FEATURE:
<223> OTHER INFORMATION: Human MBP Isoform 5

<400> SEQUENCE: 163

Met Ala Ser Gln Lys Arg Pro Ser Gln Arg His Gly Ser Lys Tyr Leu
1               5                   10                  15
Ala Thr Ala Ser Thr Met Asp His Ala Arg His Gly Phe Leu Pro Arg
            20                  25                  30
His Arg Asp Thr Gly Ile Leu Asp Ser Ile Gly Arg Phe Phe Gly Gly
        35                  40                  45
Asp Arg Gly Ala Pro Lys Arg Gly Ser Gly Lys Asp Ser His His Pro
    50                  55                  60
```

-continued

```
Ala Arg Thr Ala His Tyr Gly Ser Leu Pro Gln Lys Ser His Gly Arg
 65                  70                  75                  80

Thr Gln Asp Glu Asn Pro Val Val His Phe Phe Lys Asn Ile Val Thr
                 85                  90                  95

Pro Arg Thr Pro Pro Pro Ser Gln Gly Lys Gly Arg Gly Leu Ser Leu
                100                 105                 110

Ser Arg Phe Ser Trp Gly Ala Glu Gly Gln Arg Pro Gly Phe Gly Tyr
            115                 120                 125

Gly Gly Arg Ala Ser Asp Tyr Lys Ser Ala His Lys Gly Phe Lys Gly
        130                 135                 140

Val Asp Ala Gln Gly Thr Leu Ser Lys Ile Phe Lys Leu Gly Gly Arg
145                 150                 155                 160

Asp Ser Arg Ser Gly Ser Pro Met Ala Arg Arg
                165                 170

<210> SEQ ID NO 164
<211> LENGTH: 20
<212> TYPE: PRT
<213> ORGANISM: Homo sapiens
<220> FEATURE:
<223> OTHER INFORMATION: Human MBP peptide, amino acids 12-31
<220> FEATURE:
<221> NAME/KEY: MOD_RES
<222> LOCATION: (12)..(12)
<223> OTHER INFORMATION: Citrullinated residue
<220> FEATURE:
<221> NAME/KEY: MOD_RES
<222> LOCATION: (18)..(18)
<223> OTHER INFORMATION: Citrullinated residue

<400> SEQUENCE: 164

Tyr Leu Ala Ser Ala Ser Thr Met Asp His Ala Arg His Gly Phe Leu
 1               5                  10                  15

Pro Arg His Arg
            20

<210> SEQ ID NO 165
<211> LENGTH: 20
<212> TYPE: PRT
<213> ORGANISM: Homo sapiens
<220> FEATURE:
<223> OTHER INFORMATION: Human MBP peptide, amino acids 12-29
<220> FEATURE:
<221> NAME/KEY: MOD_RES
<222> LOCATION: (12)..(12)
<223> OTHER INFORMATION: Citrullinated residue
<220> FEATURE:
<221> NAME/KEY: MOD_RES
<222> LOCATION: (18)..(18)
<223> OTHER INFORMATION: Citrullinated residue
<220> FEATURE:
<221> NAME/KEY: MOD_RES
<222> LOCATION: (20)..(20)
<223> OTHER INFORMATION: Citrullinated residue

<400> SEQUENCE: 165

Tyr Leu Ala Ser Ala Ser Thr Met Asp His Ala Arg His Gly Phe Leu
 1               5                  10                  15

Pro Arg His Arg
            20

<210> SEQ ID NO 166
<211> LENGTH: 20
<212> TYPE: PRT
<213> ORGANISM: Homo sapiens
```

```
<220> FEATURE:
<223> OTHER INFORMATION: Human MBP peptide, amino acids 32-51
<220> FEATURE:
<221> NAME/KEY: MOD_RES
<222> LOCATION: (10)..(10)
<223> OTHER INFORMATION: Citrullinated residue
<220> FEATURE:
<221> NAME/KEY: MOD_RES
<222> LOCATION: (16)..(16)
<223> OTHER INFORMATION: Citrullinated residue

<400> SEQUENCE: 166

Asp Thr Gly Ile Leu Asp Ser Leu Gly Arg Phe Phe Gly Ser Asp Arg
1               5                   10                  15

Gly Ala Pro Lys
            20

<210> SEQ ID NO 167
<211> LENGTH: 22
<212> TYPE: PRT
<213> ORGANISM: Homo sapiens
<220> FEATURE:
<223> OTHER INFORMATION: Human MBP peptide, amino acids 52-73
<220> FEATURE:
<221> NAME/KEY: MOD_RES
<222> LOCATION: (1)..(1)
<223> OTHER INFORMATION: Citrullinated residue
<220> FEATURE:
<221> NAME/KEY: MOD_RES
<222> LOCATION: (12)..(12)
<223> OTHER INFORMATION: Citrullinated residue

<400> SEQUENCE: 167

Arg Gly Ser Gly Lys Asp Gly His His Ala Ala Arg Thr Thr His Tyr
1               5                   10                  15

Gly Ser Leu Pro Gln Lys
            20

<210> SEQ ID NO 168
<211> LENGTH: 17
<212> TYPE: PRT
<213> ORGANISM: Homo sapiens
<220> FEATURE:
<223> OTHER INFORMATION: Human MBP peptide, amino acids 74-90
<220> FEATURE:
<221> NAME/KEY: MOD_RES
<222> LOCATION: (5)..(5)
<223> OTHER INFORMATION: Citrullinated residue

<400> SEQUENCE: 168

Ala Gln Gly His Arg Pro Gln Asp Glu Asn Pro Val Val His Phe Phe
1               5                   10                  15

Lys

<210> SEQ ID NO 169
<211> LENGTH: 17
<212> TYPE: PRT
<213> ORGANISM: Homo sapiens
<220> FEATURE:
<223> OTHER INFORMATION: Human MBP peptide, amino acids 105-121
<220> FEATURE:
<221> NAME/KEY: MOD_RES
<222> LOCATION: (2)..(2)
<223> OTHER INFORMATION: Citrullinated residue
<220> FEATURE:
<221> NAME/KEY: MOD_RES
<222> LOCATION: (8)..(8)
<223> OTHER INFORMATION: Citrullinated residue
```

```
<400> SEQUENCE: 169

Gly Arg Gly Leu Ser Leu Ser Arg Phe Ser Trp Gly Ala Glu Gly Gln
1               5                   10                  15

Lys
```